(12) United States Patent
Suzuki et al.

(10) Patent No.: US 10,119,030 B2
(45) Date of Patent: Nov. 6, 2018

(54) RHODAMINE-BASED COLORING COMPOSITION

(71) Applicant: WAKO PURE CHEMICAL INDUSTRIES, LTD., Osaka-shi, Osaka (JP)

(72) Inventors: Katsufumi Suzuki, Kawagoe (JP); Tomoaki Horie, Kawagoe (JP); Yukihiko Shida, Kawagoe (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 0 days.

(21) Appl. No.: 15/129,607

(22) PCT Filed: Mar. 27, 2015

(86) PCT No.: PCT/JP2015/059695
§ 371 (c)(1),
(2) Date: Sep. 27, 2016

(87) PCT Pub. No.: WO2015/147285
PCT Pub. Date: Oct. 1, 2015

(65) Prior Publication Data
US 2017/0145216 A1    May 25, 2017

(30) Foreign Application Priority Data
Mar. 28, 2014  (JP) .................. 2014-070527

(51) Int. Cl.
*C09B 69/10*  (2006.01)
*C08F 220/18*  (2006.01)
(Continued)

(52) U.S. Cl.
CPC .......... *C09B 69/103* (2013.01); *C07D 311/80* (2013.01); *C08F 20/36* (2013.01);
(Continued)

(58) Field of Classification Search
None
See application file for complete search history.

(56) References Cited

U.S. PATENT DOCUMENTS 9,389,347 B2*  7/2016  Fujie ..................... C09B 69/101
9,645,492 B2*  5/2017  Itou .......................... C08F 20/34
(Continued)

FOREIGN PATENT DOCUMENTS

| EP | 2 957 578 A1 | 12/2015 |
| JP | 2000-103975 A | 4/2000 |

(Continued)

OTHER PUBLICATIONS

Supplementary European Search Report dated Dec. 16, 2016, in counterpart European Application No. 15768174. (8 pages).
Office Action dated May 4, 2017, in counterpart Chinese Application No. 201580016758.7, with English translation. (11 pages).
International Search Report dated Jun. 23, 2015, issued in counterpart International Application No. PCT/JP2015/059695 (2 pages).
Madsen et al., "Synthesis of Rhodamine 6G-Based Compounds for the ATRP Synthesis of Fluorescently Labeled Biocompatible Polymers", Biomacromolecules, (2011), pp. 2225-2234. Cited in ISR. (10 pages).

*Primary Examiner* — Nicole M. Buie-Hatcher
(74) *Attorney, Agent, or Firm* — Westerman, Hattori, Daniels & Adrian, LLP

(57) ABSTRACT

A coloring composition having higher heat resistance as compared with the conventional coloring composition, including a compound represented by general formula (1), and a polymer having a monomer unit derived from the compound.

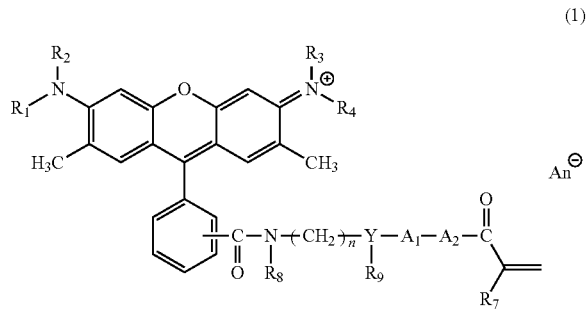

(wherein $R_1$ to $R_4$ each independently represent a hydrogen atom, an alkyl group; $R_7$ represents a hydrogen atom or a methyl group; $R_8$ and $R_9$ each independently represent a hydrogen atom or an alkyl group; Y represents a nitrogen atom or a group represented by formula (1-1):

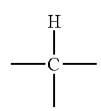

(1-1)

$A_1$ represents an alkylene group having at least one group selected from —O—, —OCO—, —COO—, —NHCO—, —CONH—, —NHCONH— and an arylene group in the chain; $A_2$ represents —NH— or —O—; An⁻ represents an anion containing an aryl group having an electron-withdrawing substituent; n represents an integer of 0 to 3; $R_8$ and $R_9$ may form a cyclic structure of a 5 to 6 membered ring together with —N—$(CH_2)_n$—Y— bonding thereto.)

20 Claims, No Drawings

(51) Int. Cl.
    *C08F 220/56* (2006.01)
    *C09B 11/24* (2006.01)
    *C07D 311/80* (2006.01)
    *C08F 20/36* (2006.01)

(52) U.S. Cl.
    CPC .......... *C08F 220/18* (2013.01); *C08F 220/56* (2013.01); *C09B 11/24* (2013.01)

(56) References Cited

U.S. PATENT DOCUMENTS

2001/0018503 A1    8/2001  Whipple et al.
2004/0051781 A1*   3/2004  Kawaguchi ............ C09K 11/06
                                                        348/34
2015/0322265 A1   11/2015  Park et al.
2016/0040013 A1    2/2016  Shida et al.

FOREIGN PATENT DOCUMENTS

| JP | 2011213925 A    | * 10/2011 | ........... C09B 69/101 |
| JP | 2012-46712 A    | 3/2012    | |
| JP | 2012-83651 A    | 4/2012    | |
| JP | 2013-178478 A   | 9/2013    | |
| WO | 01/07430 A1     | 2/2001    | |
| WO | 2013/147422 A1  | 10/2013   | |
| WO | 2014/126167 A1  | 8/2014    | |
| WO | WO-2014181834 A1 | * 11/2014 | ............ C08F 20/34 |

* cited by examiner

RHODAMINE-BASED COLORING COMPOSITION

TECHNICAL FIELD

The present invention relates to a rhodamine-based coloring compound which is used in an application of color pixel formation such as a color filter, or in applications of printing ink, inkjet ink, paint, and the like; a polymer having a monomer unit derived from the compound; and a coloring composition comprising the polymer.

BACKGROUND ART

As a method for forming a color pixel in manufacturing a color filter of a liquid crystal display element, a solid-state image sensing element, and the like, a dyeing method or a dye-dispersion method employing a dye for a colorant, a pigment-dispersion method using a pigment, an electrodeposition method, a printing method, and the like, has been known. In recent years, as characteristics of the color filter, enhancement of brightness and contrast is particularly required. According to the pigment-dispersion method using a pigment, because of higher heat resistance and light resistance as compared with a dye, a color pixel having less deterioration at heating process in manufacturing a panel, and also having high long-term reliability can be obtained. Therefore, at present, the pigment-dispersion method has become the mainstream. However, when a pigment was used, because the pigment itself has relatively large particle size, there was a problem that contrast may be decreased by light scattering. Although an attempt has also been made to micronize the pigment, there is a limit in micronization, and it has also been a problem to secure dispersion stability of the micronized pigment.

On the other hand, as a method that is capable of resolving these problems, a method for forming the color pixel using a dye has been studied at present. When the dye is used, contrast is enhanced because light scattering is suppressed. However, because the dye has lower heat resistance as compared with a pigment, and has sublimation depending on the type, there were problems, such as reduction in brightness, fading and hue change. Therefore, in the method using the dye, it has been required to resolve these problems. Regarding the color filter using the dye, various reports have been made, for example, in JP-A-2012-83651, a colored resin composition using a rhodamine derivative as the dye has been reported.

CITATION LIST

Patent Literature

[PATENT LITERATURE 1] JP-A-2012-83651

SUMMARY OF INVENTION

Technical Problem

Although we have studied the colored resin composition using the rhodamine derivative reported by JP-A-2012-83651, heat resistance in a practical range was not obtained. Therefore, an object of the present invention is to provide a coloring composition having higher heat resistance as compared with a conventional coloring composition.

Solution to Problem

In view of the above-situation, the present inventors, as a result of intensive study, have discovered that a coloring composition has excellent heat resistance and less dye elution, by using a compound which has a cationic rhodamine derivative having a specific anion, as a counter anion, and an ethylenically unsaturated bond, or a polymer having a monomer unit derived from the compound, as a dye; and have completed the present invention.

That is, the present invention relates to "a compound represented by the following general formula (1) (hereinafter, it may be abbreviated as the compound of the present invention):

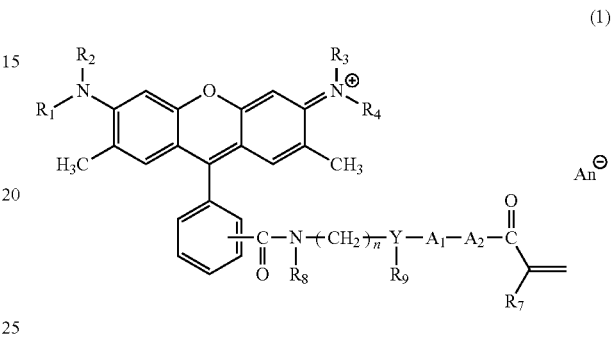

(1)

(wherein $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenated alkyl group having 1 to 6 carbon atoms, a phenyl group having a substituent or not having a substituent, or a benzyl group having a substituent or not having a substituent; $R_7$ represents a hydrogen atom or a methyl group; $R_8$ represents a hydrogen atom or an alkyl group having 1 to 30 carbon atoms; $R_9$ represents a hydrogen atom or an alkyl group having 1 to 6 carbon atoms; Y represents a nitrogen atom or the group represented by the following formula (1-1):

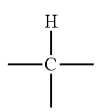

(1-1)

$A_1$ represents an alkylene group having 1 to 21 carbon atoms which has at least one group selected from —O—, —OCO—, —COO—, —NHCO—, —CONH—, —NHCONH— and an arylene group in the chain; an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent; an alkylene group having 1 to 21 carbon atoms which has a hydroxy group as a substituent; or an alkylene group having 1 to 21 carbon atoms; $A_2$ represents —NH— or —O—; $An^-$ represents an anion containing an aryl group having an electron-withdrawing substituent, a sulfonyl group having an electron-withdrawing substituent, or a halogenated alkyl group; n represents an integer of 0 to 3; $R_8$ and $R_9$ may form a cyclic structure of a 5 to 6 membered ring together with —N—$(CH_2)_n$—Y— bonding thereto", "a polymer having the monomer unit derived from the compound represented by the above-described general formula (1) (hereinafter, it may be abbreviated as the polymer of the present invention)", "a coloring composition comprising the above-described compound or the above-described polymer", and "a coloring composition for a color filter comprising the above-described compound or the above-described polymer".

Advantageous Effects of Invention

When the compound or the polymer of the present invention is used as a colorant, even if heating is carried out at 230° C. for 30 minutes, fading caused by heating is less, and high heat resistance effect is exerted. That is, the coloring composition containing the compound or the polymer of the present invention, has superior heat resistance effect as compared with the conventional coloring composition, thus it is capable of forming a superior colored cured film. Therefore, the coloring composition of the present invention can be used in an application of color pixel formation, such as a color filter used in a liquid crystal display (LCD) or a solid-state imaging element (CCD, CMOS, and the like), or in applications of printing ink, inkjet ink, paint, and the like; and particularly, it can be suitably used for the color filter of the liquid crystal display. Still more, the coloring composition of the present invention can also be used as a colored resin molded articles by molding to a sheet, a film, a bottle, a cup, and the like, using a conventionally known molding method. Accordingly, it can also be used in applications of spectacles, color contact lens, and the like; and it can be used in similar applications also by making a multi-layered structure with a known resin. In addition, it can also be used in applications of, for example, an optical film, a hair coloring agent, a labeling material for a compound or a biomaterial, a material of an organic solar battery, and the like.

In addition, when the compound or the polymer of the present invention is used by mixing into a resist material as a colorant, it exerts the effect that dye (colorant) elution is less. Therefore, as compared with the conventional coloring composition, it is capable of providing an excellent coloring composition not having problems of deterioration of color concentration, color mixture, and the like.

DESCRIPTION OF EMBODIMENTS

[Anion Containing the Aryl Group having the Electron-withdrawing Substituent, the Sulfonyl Group having the Electron-withdrawing Substituent, or the Halogenated Alkyl Group]

An anion moiety in the anion containing the aryl group having the electron-withdrawing substituent, the sulfonyl group having the electron-withdrawing substituent, or the halogenated alkyl group, represented by An⁻ of the general formula (1) (hereinafter, it may be abbreviated as the anion of the present invention), includes, for example, a sulfonate anion, a nitrogen anion (N⁻), a quaternary boron anion, a nitrate ion, a phosphate ion, and the like, and a sulfonate anion, a nitrogen anion and a quaternary boron anion are preferable, and a quaternary boron anion is more preferable.

The electron-withdrawing substituent in the aryl group having the electron-withdrawing substituent or the sulfonyl group having the electron-withdrawing substituent, in the anion of the present invention, includes, for example, a halogenated alkyl group having 1 to 3 carbon atoms, a halogeno group, a nitro group, and the like, and among them, a halogenated alkyl group having 1 to 3 carbon atoms, and a halogeno group are preferable, and a halogeno group is particularly preferable.

The halogenated alkyl group having 1 to 3 carbon atoms, as the electron-withdrawing substituent, includes, for example, a chloroalkyl group such as a chloromethyl group, a trichloromethyl group, a 2-chloroethyl group, a 2,2,2-trichloroethyl group, a pentachloroethyl group, a 2-chloropropyl group, a 3-chloropropyl group, a 2-chloro-2-propyl group and a heptachloropropyl group; a bromoalkyl group such as a bromomethyl group, a tribromomethyl group, a 2-bromoethyl group, a 2,2,2-tribromoethyl group, a pentabromoethyl group, a 2-bromopropyl group, a 3-bromopropyl group, a 2-bromo-2-propyl group and a heptabromopropyl group; an iodoalkyl group such as an iodomethyl group, a triiodomethyl group, a 2-iodoethyl group, a 2,2,2-triiodoethyl group, a pentaiodoethyl group, a 2-iodopropyl group, a 3-iodopropyl group, a 2-iodo-2-propyl group and a heptaiodopropyl group; and a fluoroalkyl group such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group and a heptafluoropropyl group. Among them, a perhalogeno alkyl group such as a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, a trifluoromethyl group, a pentafluoroethyl group and a heptafluoropropyl group, are preferable, and a perfluoroalkyl group such as a trifluoromethyl group, a pentafluoroethyl group and a heptafluoropropyl group, are more preferable, and a trifluoromethyl group is particularly preferable.

The halogeno group as the electron-withdrawing substituent includes a fluoro group, a chloro group, a bromo group and an iodo group, and a fluoro group is preferable.

As the electron-withdrawing substituent in the aryl group having the electron-withdrawing substituent in the anion of the present invention, among the above-described specific examples, the one having strong electron-withdrawing ability is preferable; and a trifluoromethyl group, a fluoro group and a nitro group are preferable, and a fluoro group is more preferable.

As the electron-withdrawing substituent in the sulfonyl group having the electron-withdrawing substituent in the anion of the present invention, among the above-described specific examples, a trifluoromethyl group, a pentafluoroethyl group, a heptafluoropropyl group and a fluoro group are preferable.

The aryl group in the aryl group having the electron-withdrawing substituent in the anion of the present invention includes, for example, a phenyl group, a naphthyl group, and the like, and a phenyl group is preferable.

Specific examples of the aryl group having the electron-withdrawing substituent, in the anion of the present invention, include, for example, those represented by the following general formulae (11) and (12).

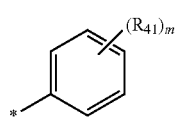

(11)

(wherein m represents an integer of 1 to 5; m pieces of $R_{41}$ each independently represent a halogenated alkyl group having 1 to 3 carbon atoms, a halogen atom or a nitro group; * represents an atomic bonding.)

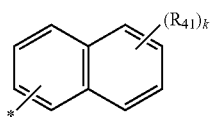

(12)

(wherein k represents an integer of 1 to 7; $R_{41}$ and * are the same as described above; k pieces of $R_{41}$ may be the same or different.)

As for m, it is usually an integer of 1 to 5, and, in the case where $R_{41}$ is a halogen atom, 2 to 5 is preferable, and 3 to 5 is more preferable, and 5 is still more preferable. In the case where $R_{41}$ is a nitro group, 1 to 3 is preferable, and 1 is more preferable. In the case where $R_{41}$ is a halogenated alkyl group, 1 to 5 is preferable, and 1 to 3 is more preferable.

As for k, it is usually an integer of 1 to 7, and, in the case where $R_{41}$ is a halogen atom, 2 to 7 is preferable. In the case where $R_{41}$ is a nitro group, 1 to 3 is preferable, and 1 is more preferable. In the case where $R_{41}$ is a halogenated alkyl group, 1 to 7 is preferable, and 1 to 3 is more preferable.

The halogenated alkyl group having 1 to 3 carbon atoms, in $R_{41}$ of the general formula (11) and the general formula (12), includes the same one as the halogenated alkyl group having 1 to 3 carbon atoms in the electron-withdrawing substituent in the anion of the present invention, and the preferable ones are also the same.

The halogen atom in $R_{41}$ of the general formula (11) and the general formula (12) includes a fluorine atom, a chlorine atom, a bromine atom, an iodine atom, and the like, and among them, a fluorine atom is preferable.

Preferable specific examples in $R_{41}$ of the general formula (11) and the general formula (12) are the same as the preferable ones of the electron-withdrawing substituent in the anion of the present invention.

The group represented by the general formula (11) specifically includes, for example, a trifluoromethylphenyl group, a di(trifluoromethyl)phenyl group, a tri(trifluoromethyl)phenyl group, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a peri-odophenyl group, a nitrophenyl group, a dinitrophenyl group, a trinitrophenyl group, and the like, and a difluorophenyl group, a trifluorophenyl group, a perfluorophenyl group, and the like, are preferable, and a perfluorophenyl group is more preferable.

The group represented by the general formula (12) specifically includes, for example, a trifluoromethylnaphthyl group, a di(trifluoromethyl)naphthyl group, a tri(trifluoromethyl)naphthyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthyl group, a perbromonaphthyl group, a monoiodonaphthyl group, a diiodonaphthyl group, a triiodonaphthyl group, a peri-odonaphthyl group, a nitronaphthyl group, a dinitronaphthyl group, a trinitronaphthyl group, and the like.

As the aryl group having the electron-withdrawing substituent in the anion of the present invention, among the above-described specific examples, the group represented by the general formula (11) is preferable, and specifically, a trifluoromethylphenyl group, a nitrophenyl group, a dinitrophenyl group, a trinitrophenyl group, a monofluorophenyl group, a difluorophenyl group, a trifluorophenyl group and a perfluorophenyl group are preferable, and a difluorophenyl group, a trifluorophenyl group, a nitrophenyl group and a perfluorophenyl group are more preferable, and a perfluorophenyl group is further preferable.

The sulfonyl group having the electron-withdrawing substituent in the anion of the present invention includes, for example, $-SO_2-CF_3$, $-SO_2-C_2F_5$, $-SO_2-C_3F_7$, $-SO_2-F$, $-SO_2-Cl$, $-SO_2-Br$, $-SO_2-I$, and the like.

The halogenated alkyl group in the anion of the present invention includes a halogenated alkyl group having 1 to 3 carbon atoms, and among them, a perhalogenated alkyl group is preferable, specifically including, for example, a trifluoromethyl group, a pentafluoroethyl group, a heptafluoropropyl group, a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, and the like, and a trifluoromethyl group, a pentafluoroethyl group and a heptafluoropropyl group are preferable.

The anion containing the aryl group having the electron-withdrawing substituent, the sulfonyl group having the electron-withdrawing substituent, or the halogenated alkyl group, pertaining to the present invention, specifically includes, for example, those represented by the following general formulae (13) to (18).

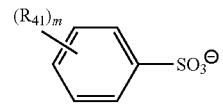

(13)

(wherein $R_{41}$ and m are the same as described above; m pieces of $R_{41}$ may be the same or different.)

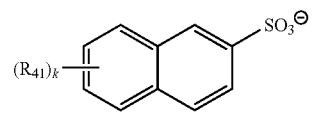

(14)

(wherein $R_{41}$ and k are the same as described above; k pieces of $R_{41}$ may be the same or different.)

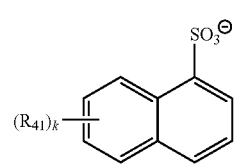

(15)

(wherein $R_{41}$ and k are the same as described above; k pieces of $R_{41}$ may be the same or different.)

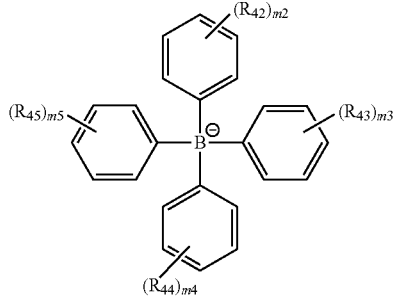
(16)

(wherein $R_{42}$ to $R_{45}$ each independently represent a halogenated alkyl group having 1 to 3 carbon atoms, a halogen atom or a nitro group; $m_2$ to $m_5$ each independently represent an integer of 1 to 5; $m_2$ pieces of $R_{42}$, $m_3$ pieces of $R_{43}$, $m_4$ pieces of $R_{44}$, and $m_5$ pieces of $R_{45}$ each may be the same or different.)

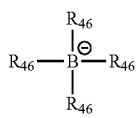
(17)

(wherein $R_{46}$ each independently represent a halogenated alkyl group having 1 to 3 carbon atoms, or a halogen atom, and at least one of four $R_{46}$ represents a halogenated alkyl group having 1 to 3 carbon atoms.)

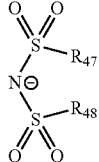
(18)

(wherein $R_{47}$ and $R_{48}$ each independently represent a halogenated alkyl group having 1 to 3 carbon atoms, or a halogen atom; $R_{47}$ together with $R_{48}$ may form a halogenated alkylene group having 2 to 3 carbon atoms.)

Combinations of $R_{41}$ and m in the general formula (13) include, for example, those described in the following table. In addition, it is preferable that the m pieces of $R_{41}$ are all the same.

| $R_{41}$ | m |
|---|---|
| trifluoromethyl group (—CF₃) | 1 to 3 |
| pentafluoroethyl group (—C₂F₅) | 1 to 3 |
| heptafluoropropyl group (—C₃F₇) | 1 to 3 |
| nitro group | 1 to 3 |
| fluorine atom | 1 to 5 |
| chlorine atom | 1 to 5 |
| bromine atom | 1 to 5 |
| iodine atom | 1 to 5 |

Preferable specific examples of the anion represented by the general formula (13) include, for example, the following ones.

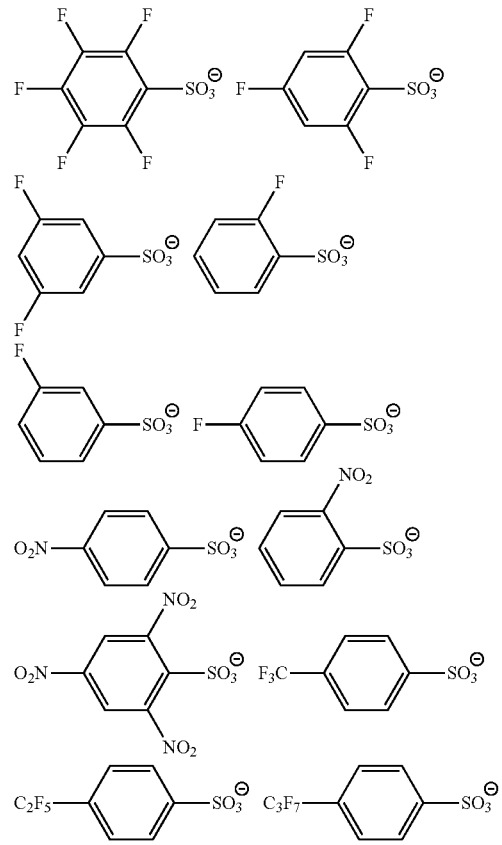

Combinations of $R_{41}$ and k in the general formulae (14) and (15) include, for example, those described in the following table. In addition, it is preferable that the k pieces of the $R_{41}$ are all the same.

| $R_{41}$ | k |
|---|---|
| trifluoromethyl group (—CF₃) | 1 to 3 |
| pentafluoroethyl group (—C₂F₅) | 1 to 3 |
| heptafluoropropyl group (—C₃F₇) | 1 to 3 |
| nitro group | 1 to 3 |
| fluorine atom | 1 to 7 |
| chlorine atom | 1 to 7 |
| bromine atom | 1 to 7 |
| iodine atom | 1 to 7 |

Preferable specific examples of the anion represented by the general formulae (14) and (15) include, for example, the following ones.

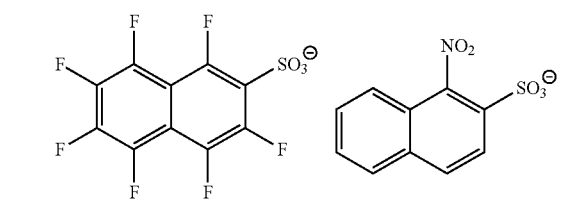

-continued

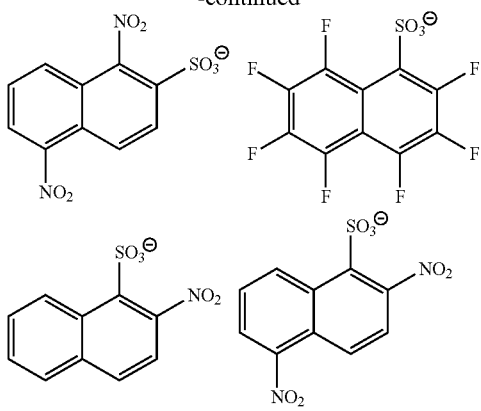

The halogenated alkyl group having 1 to 3 carbon atoms, in $R_{42}$ to $R_{45}$ of the general formula (16) includes the same one as the halogenated alkyl group having 1 to 3 carbon atoms in the anion of the present invention, and the preferable ones are also the same.

The halogen atom in $R_{42}$ to $R_{45}$ of the general formula (16) includes a fluorine atom, a chlorine atom, a bromine atom, an iodine atom, and the like, and among them, a fluorine atom is preferable.

Combinations of $R_{42}$ to $R_{45}$ and $m_2$ to $m_5$ in the general formula (16) include, for example, those described in the following table.

| $R_{42}$ | $m_2$ | $R_{43}$ | $m_3$ | $R_{44}$ | $m_4$ | $R_{45}$ | $m_5$ |
|---|---|---|---|---|---|---|---|
| —CF$_3$ | 1 to 3 | —CF$_3$ | 1 to 3 | —CF$_3$ | 1 to 3 | —CF$_3$ | 1 to 3 |
| —C$_2$F$_5$ | 1 to 3 | —C$_2$F$_5$ | 1 to 3 | —C$_2$F$_5$ | 1 to 3 | —C$_2$F$_5$ | 1 to 3 |
| —C$_3$F$_7$ | 1 to 3 | —C$_3$F$_7$ | 1 to 3 | —C$_3$F$_7$ | 1 to 3 | —C$_3$F$_7$ | 1 to 3 |
| nitro group | 1 to 3 | nitro group | 1 to 3 | nitro group | 1 to 3 | nitro group | 1 to 3 |
| fluorine | 1 to 5 | fluorine | 1 to 5 | fluorine | 1 to 5 | fluorine | 1 to 5 |
| chlorine | 1 to 5 | chlorine | 1 to 5 | chlorine | 1 to 5 | chlorine | 1 to 5 |
| bromine | 1 to 5 | bromine | 1 to 5 | bromine | 1 to 5 | bromine | 1 to 5 |
| iodine | 1 to 5 | iodine | 1 to 5 | iodine | 1 to 5 | iodine | 1 to 5 |
| nitro group | 1 to 3 | fluorine | 1 to 5 | fluorine | 1 to 5 | fluorine | 1 to 5 |
| nitro group | 1 to 3 | nitro group | 1 to 5 | fluorine | 1 to 5 | fluorine | 1 to 5 |
| nitro group | 1 to 3 | nitro group | 1 to 5 | nitro group | 1 to 5 | fluorine | 1 to 5 |

Preferable specific examples of the anion represented by the general formula (16) include, for example, the following ones.

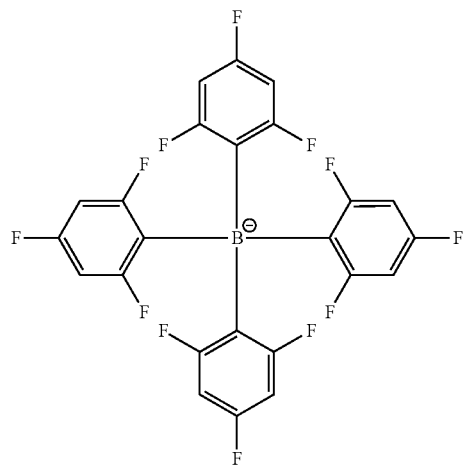

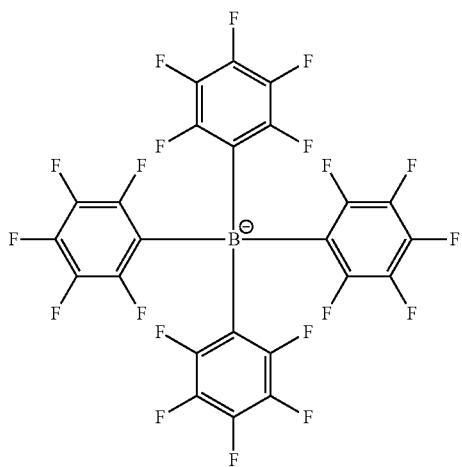

-continued

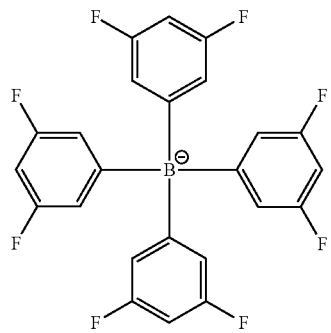

-continued
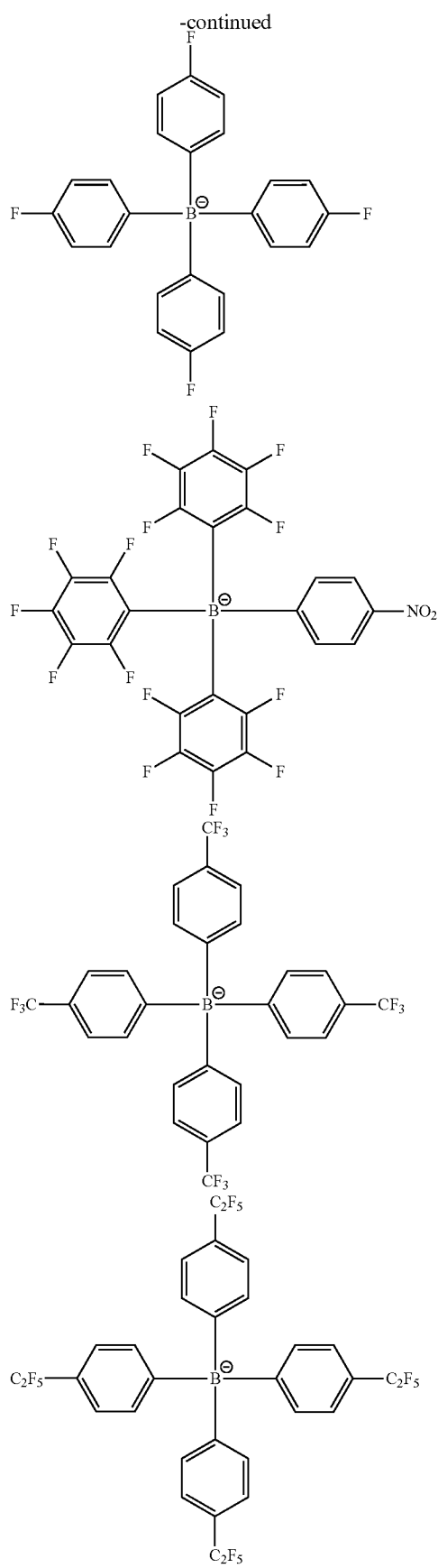
Among the above-described specific examples, the following ones are more preferable.
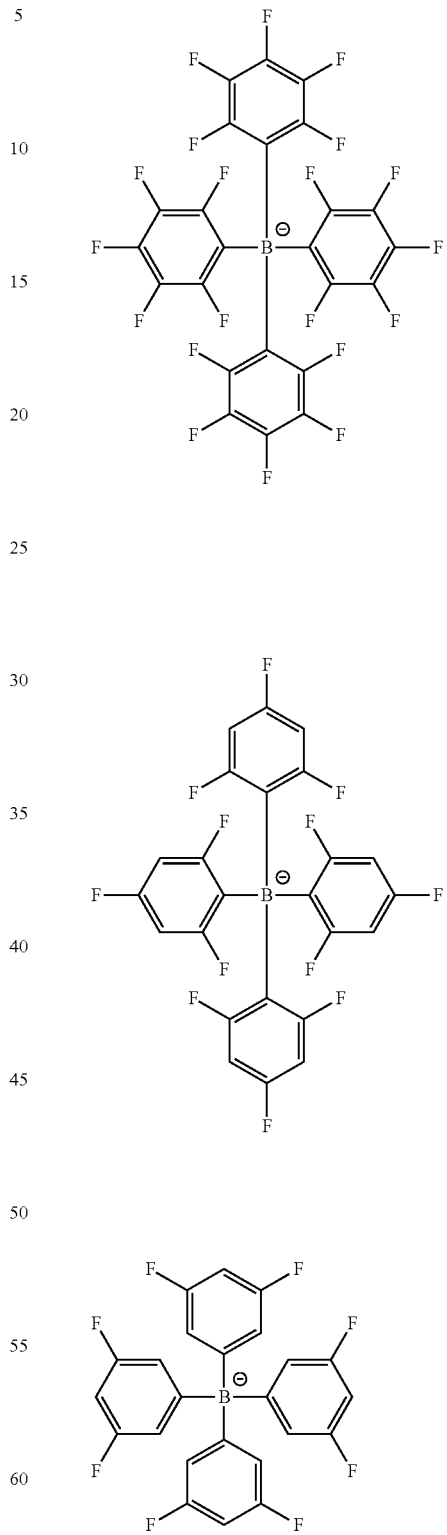
Among the above-described specific examples, the following one is particularly preferable.

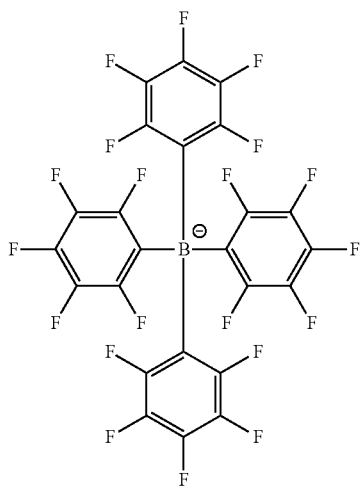 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

The halogenated alkyl group having 1 to 3 carbon atoms, in $R_{46}$ of the general formula (17), includes the same one as the halogenated alkyl group having 1 to 3 carbon atoms, in the anion of the present invention, and the preferable ones are also the same.

The halogen atom in $R_{46}$ of the general formula (17) includes a fluorine atom, a chlorine atom, a bromine atom, an iodine atom, and the like, and among them, a fluorine atom is preferable.

Preferable specific examples of the anion represented by the general formula (17) include, for example, $CF_3BF_3$, $C_2F_5BF_3$, $C_3F_7BF_3$, $(CF_3)_4B$, $(C_2F_5)_4B$, $(C_3F_7)_4B$, and the like.

The halogenated alkyl group having 1 to 3 carbon atoms, in $R_{47}$ and $R_{48}$ of the general formula (18), includes the same one as the halogenated alkyl group having 1 to 3 carbon atoms, in the anion of the present invention, and the preferable ones are also the same.

The halogen atom in $R_{47}$ and $R_{48}$ of the general formula (18) includes a fluorine atom, a chlorine atom, a bromine atom, an iodine atom, and the like, and among them, a fluorine atom is preferable.

The halogenated alkylene group having 2 to 3 carbon atoms formed with $R_{47}$ and $R_{48}$ of the general formula (18) includes, for example, a tetrafluoroethylene group, a hexafluoropropylene group, and the like, and a hexafluoropropylene group is preferable.

Preferable specific examples of the anion represented by the general formula (18) include, for example, the following ones.

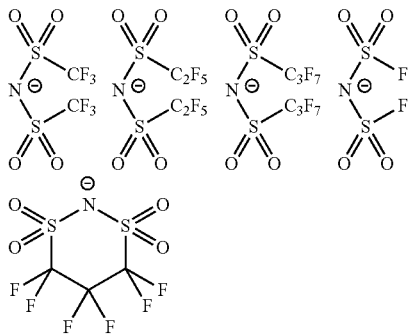

As the anion of the present invention, the one represented by the general formula (16), the general formula (17) or the general formula (18) is preferable, and the one represented by the general formula (16) or the general formula (18) is more preferable, and the one represented by the general formula (16) is particularly preferable.

As the anion of the present invention, among the above-described specific examples, the following ones are preferable.

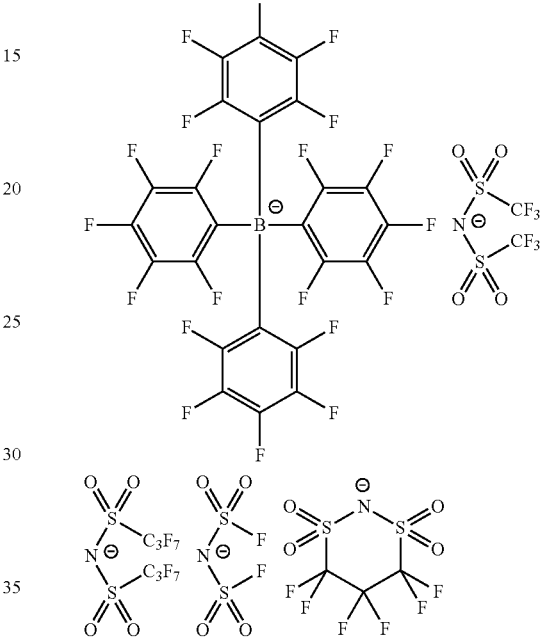

Among the above-described specific examples, the following one is particularly preferable.

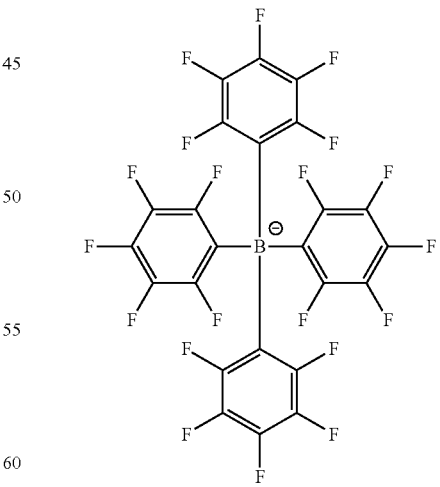

[Compound of the Present Invention]

The compound of the present invention is a compound represented by the general formula (1).

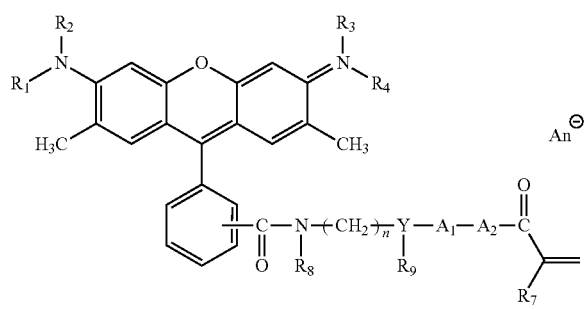

(wherein $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenated alkyl group having 1 to 6 carbon atoms, a phenyl group having a substituent or not having a substituent, or a benzyl group having a substituent or not having a substituent; $R_7$ represents a hydrogen atom or a methyl group; $R_8$ represents a hydrogen atom or an alkyl group having 1 to 30 carbon atoms; $R_9$ represents a hydrogen atom or an alkyl group having 1 to 6 carbon atoms; Y represents a nitrogen atom or the group represented by the following formula (1-1):

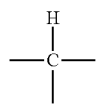

(1-1)

$A_1$ represents an alkylene group having 1 to 21 carbon atoms which has at least one group selected from —O—, —OCO—, —COO—, —NHCO—, —CONH—, —NHCONH— and an arylene group in the chain; an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent; an alkylene group having 1 to 21 carbon atoms which has a hydroxy group as a substituent; or an alkylene group having 1 to 21 carbon atoms; $A_2$ represents —NH— or —O—; An represents an anion containing an aryl group having an electron-withdrawing substituent, a sulfonyl group having an electron-withdrawing substituent, or a halogenated alkyl group; n represents an integer of 0 to 3; $R_8$ and $R_9$ may form a cyclic structure of a 5 to 6 membered ring together with —N—$(CH_2)_n$—Y— bonding thereto.)

The alkyl group having 1 to 30 carbon atoms, in $R_1$ to $R_4$ of the general formula (1), may be any of the linear, branched, or cyclic one, and the one having 1 to 12 carbon atoms is preferable, and the one having 1 to 6 carbon atoms is more preferable, and the one having 1 to 3 carbon atoms is further preferable. Specifically it includes, for example, a methyl group, an ethyl group, a propyl group, an isopropyl group, a butyl group, a 1-methylpropyl group, an isobutyl group, a tert-butyl group, a pentyl group, a 1-ethylpropyl group, a 1-methylbutyl group, a cyclopentyl group, a hexyl group, a 1-methylpentyl group, a 1-ethylbutyl group, a cyclohexyl group, a 2-heptyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, a tetracosyl group, a pentacosyl group, a hexacosyl group, a heptacosyl group, an octacosyl group, a nonacosyl group, a triacontyl group, an isopentyl group, an isohexyl group, an isoheptyl group, an isooctyl group, an isononyl group, an isodecyl group, an isoundecyl group, an isododecyl group, an isotridecyl group, an isotetradecyl group, an isopentadecyl group, an isohexadecyl group, an isoheptadecyl group, an isooctadecyl group, an isononadecyl group, an isoicosyl group, an isohenicosyl group, an isodocosyl group, an isotricosyl group, an isotetracosyl group, an isopentacosyl group, an isohexacosyl group, an isoheptacosyl group, an isooctacosyl group, an isononacosyl group, an isotriacontyl group, a 1-methylhexyl group, a 2-ethylhexyl group, a 1-methylheptyl group, a 1-cyclohexylethyl group, a 1-ethylheptyl group, a 1-heptyloctyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-tert-butylcyclohexyl group, a 1-adamantyl group, a 2-adamantyl group, and the like; a methyl group, an ethyl group, a propyl group, an isopropyl group, a butyl group, a pentyl group and a hexyl group are preferable; a methyl group, an ethyl group and a propyl group are more preferable; and a methyl group and an ethyl group are particularly preferable.

As the hydroxyalkyl group having 1 to 6 carbon atoms in $R_1$ to $R_4$ of the general formula (1), the one having 1 to 3 carbon atoms is preferable, specifically including, for example, a hydroxymethyl group, a hydroxyethyl group, a hydroxypropyl group, a hydroxybutyl group, a hydroxypentyl group, a hydroxyhexyl group, and the like.

As the sulfoalkyl group having 1 to 6 carbon atoms in $R_1$ to $R_4$ of the general formula (1), the one having 1 to 3 carbon atoms is preferable, specifically including, for example, a sulfomethyl group, a sulfoethyl group, a sulfopropyl group, a sulfobutyl group, a sulfopentyl group, a sulfohexyl group, and the like.

As the carboxyalkyl group having 2 to 7 carbon atoms in $R_1$ to $R_4$ of the general formula (1), the one having 3 to 6 carbon atoms is preferable, specifically including, for example, a carboxymethyl group, a carboxyethyl group, a carboxypropyl group, a carboxybutyl group, a carboxypentyl group, a carboxyhexyl group, and the like, and a carboxyethyl group is preferable.

As the cyanoalkyl group having 2 to 7 carbon atoms in $R_1$ to $R_4$ of the general formula (1), the one having 2 to 4 carbon atoms is preferable, specifically including, for example, a cyanomethyl group, a cyanoethyl group, a cyanopropyl group, a cyanobutyl group, a cyanopentyl group, a cyanohexyl group, and the like, and a cyanoethyl group is preferable.

As the alkoxyalkyl group having 2 to 6 carbon atoms in $R_1$ to $R_4$ of the general formula (1), the one having 3 to 5 carbon atoms is preferable, specifically including, for example, a methoxymethyl group, a methoxyethyl group, an ethoxymethyl group, an ethoxyethyl group, a propoxymethyl group, a propoxyethyl group, a butoxymethyl group, a butoxyethyl group, and the like.

As the halogenated alkyl group having 1 to 6 carbon atoms in $R_1$ to $R_4$ of the general formula (1), the one having 1 to 3 carbon atoms is preferable, specifically including, for example, a trifluoromethyl group, a pentafluoroethyl group, a heptafluoropropyl group, a trichloromethyl group, a tribromomethyl group, a triiodomethyl group, and the like.

The phenyl group having a substituent, or the benzyl group having a substituent, in $R_1$ to $R_4$ of the general formula (1), has one to five substituents, and preferably one to three substituents. The substituent includes, for example, an alkyl group having 1 to 6 carbon atoms such as a methyl group, an ethyl group, a propyl group, an isopropyl group, a butyl group, an isobutyl group, a tert-butyl group, a pentyl group and a hexyl group; a halogen atom such as a fluorine atom, a chlorine atom, a bromine atom and an iodine atom; an alkoxy group having 1 to 6 carbon atoms such as a methoxy group, an ethoxy group, a propoxy group, a butoxy group, a tert-butoxy group, a propoxy group and a hexyloxy group; a hydroxyalkyl group having 1 to 6 carbon atoms such as a hydroxyethyl group and a hydroxypropyl group; an alkoxyalkyl group having 2 to 7 carbon atoms such as a methoxyethyl group, an ethoxyethyl group, an ethoxypropyl group and a butoxyethyl group; a hydroxyalkoxy group having 1 to 6 carbon atoms such as a 2-hydroxyethoxy group; an alkoxyalkoxy group having 2 to 7 carbon atoms such as a 2-methoxyethoxy group and a 2-ethoxyethoxy group; a sulfoalkyl group having 1 to 6 carbon atoms such as 2-sulfoethyl group; a carboxyalkyl group having 2 to 7 carbon atoms such as a carboxymethyl group, a carboxyethyl group, a carboxypropyl group, a carboxybutyl group, a carboxypentyl group and a carboxyhexyl group; a cyanoalkyl group having 2 to 7 carbon atoms such as a cyanomethyl group, a cyanoethyl group, a cyanopropyl group, a cyanobutyl group, a cyanopentyl group and a cyanohexyl group; a sulfo group; and the like.

As $R_1$ and $R_4$ in the general formula (1), a hydrogen atom, or an alkyl group having 1 to 30 carbon atoms is preferable, and a hydrogen atom, or an alkyl group having 1 to 6 carbon atoms is more preferable. Specifically, a hydrogen atom, a methyl group, an ethyl group, a propyl group, an isopropyl group, a butyl group, a pentyl group, a hexyl group, and the like, are preferable, and a hydrogen atom, a methyl group, an ethyl group, a propyl group, and the like, are more preferable, and a hydrogen atom is particularly preferable.

As $R_2$ and $R_3$ in the general formula (1), a hydrogen atom, or an alkyl group having 1 to 30 carbon atoms is preferable, and a hydrogen atom, or an alkyl group having 1 to 6 carbon atoms is more preferable, and an alkyl group having 1 to 6 carbon atoms is particularly preferable. Specifically, a hydrogen atom, a methyl group, an ethyl group, a propyl group, an isopropyl group, a butyl group, a pentyl group, a hexyl group, and the like, are preferable, and a methyl group, an ethyl group, a propyl group, and the like, are more preferable, and an ethyl group is particularly preferable.

$R_7$ of the general formula (1) represents a hydrogen atom or a methyl group, and a methyl group is preferable.

The alkyl group having 1 to 30 carbon atoms in $R_8$ of the general formula (1) includes the same one as the alkyl group having 1 to 30 carbon atoms in $R_1$ to $R_4$ of the general formula (1), and the preferable ones are also the same.

As $R_8$ in the general formula (1), a hydrogen atom, an alkyl group having 1 to 6 carbon atoms, or the case where $R_8$ and $R_9$ form a cyclic structure of a 5 to 6 membered ring together with —N—$(CH_2)_n$—Y— bonding thereto is preferable, and a hydrogen atom is more preferable. Specifically, a hydrogen atom, a methyl group, an ethyl group, a propyl group, an isopropyl group, a butyl group, a pentyl group, a hexyl group, or the case where a cyclic structure represented by the general formula (1-2) as described below is formed, is preferable; a hydrogen atom, a methyl group, an ethyl group, a propyl group, or the case where a structure included as a specific example of the cyclic structure represented by the general formula (1-2) as described below is formed, is more preferable; a hydrogen atom, or the case where a structure included as a preferable specific example of the cyclic structure represented by the general formula (1-2) as described below is formed, is further preferable; and a hydrogen atom is particularly preferable.

The alkyl group having 1 to 6 carbon atoms in $R_9$ of the general formula (1) may be any of the linear, branched, or cyclic one, and the one having 1 to 3 carbon atoms is preferable. Specifically it includes, for example, a methyl group, an ethyl group, a propyl group, an isopropyl group, a butyl group, a 1-methylpropyl group, an isobutyl group, a pentyl group, a 1-ethylpropyl group, a 1-methylbutyl group, a cyclopentyl group, a hexyl group, a 1-methylpentyl group, a 1-ethylbutyl group, a cyclohexyl group, and the like; a methyl group, an ethyl group, a propyl group, an isopropyl group, a butyl group, a pentyl group, a hexyl group, and the like, are preferable; and a methyl group, an ethyl group, a propyl group, and the like, are more preferable.

As $R_9$ in the general formula (1), a hydrogen atom, or the case where $R_8$ and $R_9$ form a cyclic structure of a 5 to 6 membered ring together with —N—$(CH_2)_n$—Y— bonding thereto is preferable, and a hydrogen atom is more preferable. Specifically it includes, a hydrogen atom, a methyl group, an ethyl group, a propyl group, an isopropyl group, a butyl group, a pentyl group, a hexyl group, the case where a cyclic structure represented by the general formula (1-2) as described below is formed, and the like; a hydrogen atom, a methyl group, an ethyl group, a propyl group, or the case where a structure included as a specific example of the cyclic structure represented by the general formula (1-2) as described below is formed, is preferable; a hydrogen atom, or the case where a structure included as a preferable specific example of the cyclic structure represented by the general formula (1-2) as described below is formed, is more preferable; and a hydrogen atom is particularly preferable.

In the case where $R_8$ and $R_9$ form a cyclic structure of a 5 to 6 membered ring together with —N—$(CH_2)_n$—Y— bonding thereto, Y of the general formula (1) is preferably a nitrogen atom; and in the case where the cyclic structure is not formed, it is preferably the group represented by the formula (1-1).

In the case where $R_8$ and $R_9$ form a cyclic structure of a 5 to 6 membered ring together with —N—$(CH_2)_n$—Y— bonding thereto, the cyclic structure is the one represented by the general formula (1-2):

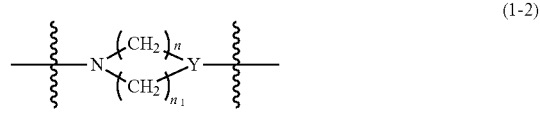

(1-2)

(wherein $n_1$ represents an integer of 0 to 4; Y and n are the same as described above, and $n+n_1$ is an integer of 3 to 4.)

In the case where the cyclic structure represented by the general formula (1-2) is formed, n of the general formula (1) is preferably 2; and in the case where the cyclic structure represented by the general formula (1-2) is not formed, n is preferably 1.

As for $n_1$ of the general formula (1-2), 2 is preferable.

The cyclic structure represented by the general formula (1-2) represents a 5 to 6 membered ring, and a 6 membered ring is preferable.

Specific examples of the cyclic structures represented by the general formula (1-2) include, for example, the following ones.

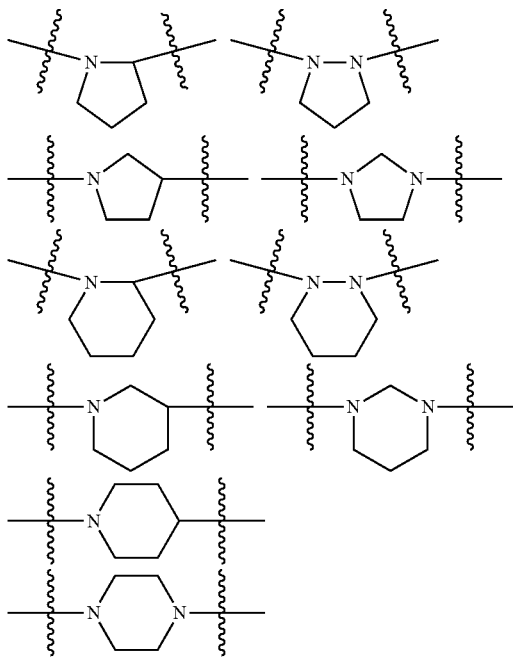

Among specific examples of the cyclic structures, the following ones are preferable:

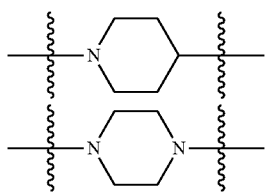

The alkylene group having 1 to 21 carbon atoms in "an alkylene group having 1 to 21 carbon atoms which has at least one group selected from —O—, —OCO—, —COO—, —NHCO—, —CONH—, —NHCONH— and an arylene group in the chain", "an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", "an alkylene group having 1 to 21 carbon atoms which has a hydroxy group as a substituent" and "an alkylene group having 1 to 21 carbon atoms", in $A_1$ of the general formula (1), may be any of the linear, branched, or cyclic one, and the one having 1 to 12 carbon atoms is preferable, and the one having 1 to 6 carbon atoms is more preferable, and the one having 1 to 3 carbon atoms is further preferable. Specifically it includes, for example, a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group, an n-heptylene group, an n-octylene group, an n-nonylene group, an n-decylene group, an n-undecylene group, an n-dodecylene group, an n-tridecylene group, an n-tetradecylene group, an n-pentadecylene group, an n-hexadecylene group, an n-heptadecylene group, an n-octadecylene group, an n-nonadecylene group, an n-icosylene group, an n-henicosylene group, —$C_4H_6$—$CH_2$— group, —$C_5H_8CH_2$— group, —$C_6H_{10}$—$CH_2$— group, —$C_6H_{10}$—$C_2H_4$— group, —$C_6H_{10}$—$C_3H_6$— group, —$C_7H_{12}$—$CH_2$— group, and the like, and a methylene group, an ethylene group, a propylene group, a butylene group, a pentylene group, a hexylene group, —$C_6H_{10}$—$CH_2$— group, —$C_6H_{10}$—$C_2H_4$— group, —$C_6H_{10}$—$C_3H_6$— group, and the like, are preferable, and a methylene group, an ethylene group and a propylene group are more preferable, and an ethylene group is particularly preferable.

The arylene group in "an alkylene group having 1 to 21 carbon atoms which has at least one group selected from —O—, —OCO—, —COO—, —NHCO—, —CONH—, —NHCONH— and an arylene group in the chain" and "an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", in $A_1$ of the general formula (1), includes the one having 6 to 10 carbon atoms, and specifically includes a phenylene group, a naphthylene group, and the like.

"An alkylene group having 1 to 21 carbon atoms which has at least one group selected from —O—, —OCO—, —COO—, —NHCO—, —CONH—, —NHCONH— and an arylene group in the chain", in $A_1$ of the general formula (1), includes, for example, the groups represented by the following general formulae (21-1) to (21-5), and the like.

   (21-1)

(wherein $R_{51}$ represents a linear or branched alkylene group having 1 to 4 carbon atoms, $h_1$ represents an integer of 1 to 10, and total number of carbon atoms in the formula is 1 to 21.)

   (21-2)

(wherein $h_2$ represents an integer of 1 to 10, $h_3$ represents an integer of 0 to 10.)

   (21-3)

(wherein $R_{52}$ represents a phenylene group, or an alkylene group having 1 to 7 carbon atoms, $h_4$ represents an integer of 1 to 3.)

   (21-4)

(wherein $Y_1$ represents —NHCO—, —CONH— or —NHCONH—; $h_5$ represents an integer of 1 to 10.)

   (21-5)

(wherein $h_6$ represents an integer of 1 to 10.)

The linear or branched alkylene group having 1 to 4 carbon atoms, in $R_{51}$ of the general formula (21-1), specifically includes, for example, a methylene group, an ethylene group, a methylmethylene group, a propylene group, a methylethylene group, a butylene group, a methylpropylene group, and the like, and an ethylene group and a methylethylene group are preferable.

The alkylene group having 1 to 7 carbon atoms, in $R_{52}$ of the general formula (21-3), specifically includes, for example, a methylene group, an ethylene group, a propylene group, a butylene group, a pentylene group, a hexylene group, a heptylene group, a cyclobutylene group, a cyclopentylene group, a cyclohexylene group, a cycloheptylene group, and the like.

As $Y_1$ in the general formula (21-4), —NHCONH— is preferable.

The group represented by the general formula (21-1) specifically includes, for example,
—O—$CH_2CH_2$—, —(O—$CH_2CH_2)_2$—,
—(O—$CH_2CH_2)_3$—, —(O—$CH_2CH_2)_4$—,
—(O—$CH_2CH_2)_5$—, —(O—$CH_2CH_2)_6$—,
—(O—$CH_2CH_2)_7$—, —(O—$CH_2CH_2)_8$—,
—(O—$CH_2CH_2)_9$—, —(O—$CH_2CH_2)_{10}$—,
—O—$CH_2CH(CH_3)$—,
—(O—$CH_2CH(CH_3))_2$—, —(O—$CH_2CH(CH_3))_3$—,
—(O—$CH_2CH(CH_3))_4$—, —(O—$CH_2CH(CH_3))_5$—,
—(O—$CH_2CH(CH_3))_6$—, —(O—$CH_2CH(CH_3))_7$—,
—O—$CH(CH_3)CH_2$—,
—(O—$CH(CH_3)CH_2)_2$—, —(O—$CH(CH_3)CH_2)_3$—,
—(O—$CH(CH_3)CH_2)_4$—, —(O—$CH(CH_3)CH_2)_5$—,
—(O—$CH(CH_3)CH_2)_6$—, —(O—$CH(CH_3)CH_2)_7$—, and the like.

The group represented by the general formula (21-2) specifically includes, for example,
—$CH_2$—O—CO—,
—$CH_2$—O—CO—$(CH_2)_2$—,
—$(CH_2)_2$—O—CO—,
—$(CH_2)_2$—O—CO—$(CH_2)_2$—,
—$(CH_2)_3$—O—CO—,
—$(CH_2)_3$—O—CO—$(CH_2)_2$—, and the like The group represented by the general formulae (21-3) specifically includes, for example,
—O—CO—$CH_2$—CO—O—$CH_2$—,
—O—CO—$(CH_2)_2$—CO—O—$CH_2$—,
—O—CO—$(CH_2)_3$—CO—O—$CH_2$—,
—O—CO—$(CH_2)_4$—CO—O—$CH_2$—,
—O—CO—$(CH_2)_5$—CO—O—$CH_2$—,
—O—CO—$(CH_2)_6$—CO—O—$CH_2$—,
—O—CO—$(CH_2)_7$—CO—O—$CH_2$—,
—O—CO—$(CH_2)$—CO—O—$(CH_2)_2$—,
—O—CO—$(CH_2)_2$—CO—O—$(CH_2)_2$—,
—O—CO—$(CH_2)_3$—CO—O—$(CH_2)_2$—,
—O—CO—$(CH_2)_4$—CO—O—$(CH_2)_2$—,
—O—CO—$(CH_2)_5$—CO—O—$(CH_2)_2$—,
—O—CO—$(CH_2)_6$—CO—O—$(CH_2)_2$—,
—O—CO—$(CH_2)_7$—CO—O—$(CH_2)_2$—,
—O—CO—$CH_2$—CO—O—$(CH_2)_3$—,
—O—CO—$(CH_2)_2$—CO—O—$(CH_2)_3$—,
—O—CO—$(CH_2)_3$—CO—O—$(CH_2)_3$—,
—O—CO—$(CH_2)_4$—CO—O—$(CH_2)_3$—,
—O—CO—$(CH_2)_5$—CO—O—$(CH)_3$—,
—O—CO—$(CH_2)_6$—CO—O—$(CH_2)_3$—,
—O—CO—$(CH_2)_7$—CO—O—$(CH_2)_3$—,
—O—CO—$C_6H_4$—CO—O—$CH_2$—,
—O—CO—$C_6H_4$—CO—O—$(CH_2)_2$—,
—O—CO—$C_6H_{10}$—CO—O—$(CH_2)_3$—,
—O—CO—$C_6H_{10}$—CO—O—$CH_2$—,
—O—CO—$C_6H_{10}$—CO—O—$(CH_2)_2$—,
—O—CO—$C_6H_{10}$—CO—O—$(CH_2)$—, and the like, and among them,
—O—CO—$CH_2$—CO—O—$CH_2$—,
—O—CO—$(CH_2)_2$—CO—O—$CH_2$—,
—O—CO—$(CH_2)_3$—CO—O—$CH_2$—,
—O—CO—$(CH_2)_4$—CO—O—$CH_2$—,
—O—CO—$(CH_2)_5$—CO—O—$CH_2$—,
—O—CO—$(CH_2)_6$—CO—O—$CH_2$—,
—O—CO—$(CH_2)_7$—CO—O—$CH_2$—,
—O—CO—$CH_2$—CO—O—$(CH_2)_2$—,
—O—CO—$(CH_2)_2$—CO—O—$(CH_2)_2$—,
—O—CO—$(CH_2)_3$—CO—O—$(CH_2)_2$—,
—O—CO—$(CH_2)_4$—CO—O—$(CH_2)_2$—,
—O—CO—$(CH_2)_5$—CO—O—$(CH_2)_2$—,
—O—CO—$(CH_2)_6$—CO—O—$(CH_2)_2$—,
—O—CO—$(CH_2)_7$—CO—O—$(CH_2)_2$—,
—O—CO—$CH_2$—CO—O—$(CH_2)_3$—,
—O—CO—$(CH_2)_2$—CO—O$(CH_2)_3$—,
—O—CO—$(CH_2)_3$—CO—O—$(CH_2)_3$—,
—O—CO—$(CH_2)_4$—CO—O—$(CH_2)_3$—,
—O—CO—$(CH_2)_5$—CO—O—$(CH_2)_3$—,
—O—CO—$(CH_2)_6$—CO—O—$(CH_2)_3$— and
—O—CO—$(CH_2)_7$—CO—O—$(CH_2)_3$— are preferable, and
—O—CO—$CH_2$—CO—O—$(CH_2)_2$—,
—O—CO—$(CH_2)_2$—CO—O—$(CH_2)_2$—,
—O—CO—$(CH_2)_3$—CO—O—$(CH_2)_2$—,
—O—CO—$(CH_2)_4$—CO—O—$(CH_2)_2$—,
—O—CO—$(CH_2)_5$—CO—O—$(CH_2)_2$—,
—O—CO—$(CH_2)_6$—CO—O—$(CH_2)_2$— and
—O—CO—$(CH_2)_7$—CO—O—$(CH_2)_2$— are more preferable, and
—O—CO—$(CH_2)_2$—CO—O—$(CH_2)_2$— is particularly preferable.

The group represented by the general formula (21-4) specifically includes, for example,
—NHCO—$CH_2$—, —NHCO—$(CH_2)_2$—,
—NHCO—$(CH_2)_3$—, —NHCO—$(CH_2)_4$—,
—CONH—CH—, —CONH—$(CH_2)_2$—,
—CONH—$(CH_2)_3$—, —CONH—$(CH_2)_4$—,
—NHCONH—$CH_2$—, —NHCONH—$(CH_2)_2$—,
—NHCONH—$(CH_2)_3$—, —NHCONH—$(CH_2)_4$—,
—NHCONH—$(CH_2)_5$—, —NHCONH—$(CH_2)_6$—,
—NHCONH—$(CH_2)_7$—, —NHCONH—$(CH_2)_8$—,
—NHCONH—$(CH_2)_9$—, —NHCONH—$(CH_2)_{10}$—, and the like, and among them,
—NHCONH—$CH_2$—, —NHCONH—$(CH_2)_2$—,
—NHCONH—$(CH_2)_3$—, —NHCONH—$(CH_2)_4$—,
—NHCONH—$(CH_2)_5$—, —NHCONH—$(CH_3)_6$—,
—NHCONH—$(CH_2)_7$—, —NHCONH—$(CH_2)_8$— and
—NHCONH—$(CH_2)_9$—, —NHCONH—$(CH_2)_{10}$— are preferable, and
—NHCONH—$(CH_2)_2$— is more preferable.

The group represented by the general formula (21-5) specifically includes, for example,
—O—CONH—$CH_2$—, —O—CONH—$(CH_2)_2$—,
—O—CONH—$(CH_2)_3$—, —O—CONH—$(CH_2)_4$—, and the like.

"An alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", in $A_1$ of the general formula (1), includes, for example, the groups represented by the following general formulae (22-1) to (22-2), and the like.

$$—R_{53}—(CH_2)_{h7}— \qquad (22\text{-}1)$$

(wherein $R_{53}$ represents an arylene group having 6 to 10 carbon atoms which has a hydroxy group as a substituent, $h_7$ represents an integer of 1 to 4.)

$$—R_{54}—Y_2—(CH_2)_{h8}— \qquad (22\text{-}2)$$

(wherein $R_{54}$ represents an alkylene group having 1 to 7 carbon atoms which has a hydroxy group as a substituent, or an arylene group having 6 to 10 carbon atoms which has a hydroxy group as a substituent; $Y_2$ represents —O—, —OCO—, —COO—, —NHCO—, —CONH— or —NHCONH—; $h_8$ represents an integer of 2 to 4.)

The arylene group having 6 to 10 carbon atoms which has a hydroxy group as a substituent, in $R_{53}$ of the general formula (22-1), includes, a hydroxyphenylene group, a dihydroxyphenylene group, a hydroxynaphthylene group, a dihydroxynaphthylene group, and the like.

The alkylene group having 1 to 7 carbon atoms which has a hydroxy group as a substituent, in $R_{54}$ of the general formula (22-2), includes, a hydroxymethylene group, a hydroxyethylene group, a hydroxypropylene group, a hydroxybutylene group, a hydroxypentylene group, a hydroxyhexylene group, a hydroxyheptylene group, a hydroxycyclobutylene group, a hydroxycyclopentylene group, a hydroxycyclohexylene group, a hydroxycycloheptylene group, and the like.

The arylene group having 6 to 10 carbon atoms which has a hydroxy group as a substituent, in $R_{54}$ of the general formula (22-2), includes the same one as the arylene group having 6 to 10 carbon atoms which has a hydroxy group as a substituent, in $R_{53}$ of the general formula (22-1).

Preferable specific examples of the group represented by the general formula (22-1) include, for example,
—$C_6H_3(OH)$—$CH_2$—, —$C_6H_3(OH)$—$(CH_2)_2$—,
—$C_6H_3(OH)$—$(CH_2)_3$—, —$C_6H_3(OH)$—$(CH_2)_4$—,
—$C_6H_3(OH)_2$—$CH_2$—, —$C_6H_3(OH)_2$—$(CH_2)_2$—,
—$CH_3(OH)_2$—$(CH_2)_3$—, —$C_6H_3(OH)_2$—$(CH_2)_4$—, and the like.

Preferable specific examples of the group represented by the general formulae (22-2) include, for example,
—CH(OH)—$CH_2$—O—$(CH_2)_2$—,
—CH(OH)—$CH_2$—O—$(CH_2)_3$—,
—CH(OH)—$CH_2$—O—$(CH_2)_4$—,
—CH(OH)—$CH_2$—OCO—$(CH_2)_2$—,
—CH(OH)—$CH_2$—OCO—$(CH_2)_3$—,
—CH(OH)—$CH_2$—OCO—$(CH_2)_4$—,
—CH(OH)—$CH_2$—COO—$(CH_2)_2$—,
—CH(OH)—$CH_2$—COO—$(CH_2)_3$—,
—CH(OH)—$CH_2$—COO—$(CH_2)_4$—,
—CH(OH)—$CH_2$—NHCO—$(CH_2)_2$—,
—CH(OH)—$CH_2$—NHCO—$(CH_2)_3$—,
—CH(OH)—$CH_2$—NHCO—$(CH_2)_4$—,
—CH(OH)—$CH_2$—CONH—$(CH_2)_2$—,
—CH(OH)—$CH_2$—CONH—$(CH_2)_3$—,
—CH(OH)—$CH_2$—CONH—$(CH_2)_4$—,
—CH(OH)—$CH_2$—NHCONH—$(CH_2)_2$—,
—CH(OH)—$CH_2$—NHCONH—$(CH_2)_3$—,
—CH(OH)—$CH_2$—NHCONH—$(CH_2)_4$—, and the like.

"An alkylene group having 1 to 21 carbon atoms which has a hydroxy group as a substituent" in $A_1$ of the general formula (1) includes, for example, the group represented by the following general formula (23-1), and the like.

—$R_{55}$—$(CH_2)_{h9}$— (23-1)

(wherein $R_{55}$ represents an alkylene group having 1 to 7 carbon atoms which has a hydroxy group as a substituent, $h_9$ represents an integer of 1 to 4.)

The alkylene group having 1 to 7 carbon atoms which has a hydroxy group as a substituent, in $R_{55}$ of the general formula (23-1), includes the same one as the alkylene group having 1 to 7 carbon atoms which has a hydroxy group as a substituent, in $R_{54}$ of the general formula (22-2).

The group represented by the general formulae (23-1) specifically includes, for example,
—$C_6H_9(OH)$—$CH_2$—, —$C_6H_9(OH)$—$(CH_2)_2$—,
—$C_6H_9(OH)$—$(CH_2)_3$—, —$C_6H_9(OH)$—$(CH_2)_4$—,
—CH(OH)—$CH_2$—, —CH(OH)—$(CH_2)_2$—,
—CH(OH)—$(CH_2)_3$—, —CH(OH)—$(CH_2)_4$—, and the like.

As $A_1$ in the general formula (1), the alkylene group having 1 to 21 carbon atoms which has at least one group selected from —O—, —OCO—, —COO—, —NHCO—, —CONH—, —NHCONH— and an arylene group in the chain; and the alkylene group having 1 to 21 carbon atoms are preferable. Among them, the groups represented by the general formulae (21-3) and (21-4), as well as the alkylene group having 1 to 6 carbon atoms are preferable; and more specifically,
—O—CO—$CH_2$—CO—O—$CH_2$—,
—O—CO—$(CH_2)_2$—CO—O—$CH_2$—,
—O—CO—$(CH_2)_3$—CO—O—$CH_2$—,
—O—CO—$(CH_2)_4$—CO—O—$CH_2$—,
—O—CO—$(CH_2)_5$—CO—O—$CH_2$—,
—O—CO—$(CH_2)_6$—CO—O—$CH_2$—,
—O—CO—$(CH_2)_7$—CO—O—$CH_2$—,
—O—CO—$CH_2$—CO—O—$(CH_2)_2$—,
—O—CO—$(CH_2)_2$—CO—O—$(CH_2)_2$—,
—O—CO—$(CH_2)_3$—CO—O—$(CH_2)_2$—,
—O—CO—$(CH_2)_4$—CO—O—$(CH_2)_2$—,
—O—CO—$(CH_2)_5$—CO—O—$(CH_2)_2$—,
—O—CO—$(CH_2)_6$—CO—O—$(CH_2)_2$—,
—O—CO—$(CH_2)_7$—CO—O—$(CH_2)_2$—,
—O—CO—$CH_2$—CO—O—$(CH_2)_3$—,
—O—CO—$(CH_2)_2$—CO—O—$(CH_2)_3$—,
—O—CO—$(CH_2)_3$—CO—O—$(CH_2)_3$—,
—O—CO—$(CH_2)_4$—CO—O—$(CH_2)_3$—,
—O—CO—$(CH_2)_5$—CO—O—$(CH_2)_3$—,
—O—CO—$(CH_2)_6$—CO—O—$(CH_2)_3$—,
—O—CO—$(CH_2)_7$—CO—O—$(CH_2)_3$—,
—NHCONH—$CH_2$—, —NHCONH—$(CH_2)_2$—,
—NHCONH—$(CH_2)_3$—, —NHCONH—$(CH_2)_4$—,
—NHCONH—$(CH_2)_5$—, —NHCONH—$(CH_2)_6$—,
—NHCONH—$(CH_2)_7$—, —NHCONH—$(CH_2)_8$—,
—NHCONH—$(CH_2)_9$—, —NHCONH—$(CH_2)_{10}$—,
a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group and a methylpentylene group are preferable;
—O—CO—$CH_2$—CO—O—$(CH_2)_2$—,
—O—CO—$(CH_2)_2$—CO—O—$(CH_2)_2$—,
—O—CO—(CH)—CO—O—$(CH_2)_2$—,
—O—CO—$(CH_2)_4$—CO—O—$(CH_2)_2$—,
—O—CO—$(CH_2)_5$—CO—O—$(CH_2)_2$—,
—O—CO—$(CH_2)_6$—CO—O—$(CH_2)_2$—,
—O—CO—$(CH_2)_7$—CO—O—$(CH_2)_2$—,
—NHCONH—$CH_2$—, —NHCONH—$(CH_2)_2$—,
—NHCONH—$(CH_2)_3$—, —NHCONH—$(CH_2)_4$—,
—NHCONH—$(CH_2)_5$—, —NHCONH—$(CH_2)_6$—,
—NHCONH—$(CH_2)_7$—, —NHCONH—$(CH_2)_8$—,
—NHCONH—$(CH_2)_9$—, —NHCONH—$(CH_2)_{10}$—,
a methylene group, an ethylene group and a propylene group are more preferable; and
—O—CO—$(CH_2)_2$—CO—O—$(CH_2)_2$—,
—NHCONH—$(CH_2)_2$—,
and an ethylene group are particularly preferable.

As $A_2$ in the general formula (1), —O— is preferable.

The group represented by the following general formula (1-5) bonding to a phenyl group in a fundamental skeleton of a rhodamine, in the general formula (1), may be located at any of ortho position, meta position or para position of the phenyl group, and ortho position is preferable. Specifically, the group represented by the general formula (1-5) is preferably the one bonding to the phenyl group in the fundamental skeleton of the rhodamine, as the compound represented by the following general formula (1-6).

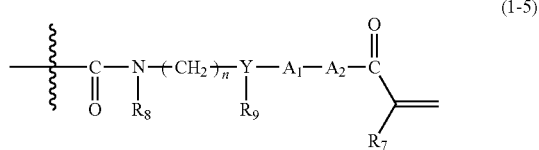
(1-5)

(wherein $R_7$ to $R_9$, Y, n, $A_1$ and $A_2$ are the same as described above.)

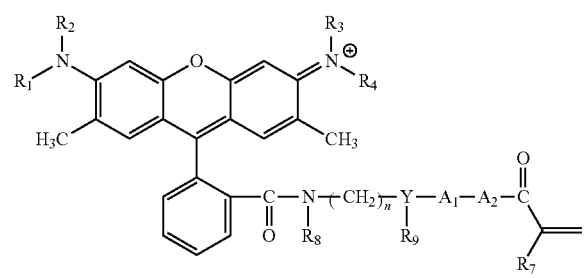
(1-6)

(wherein $R_1$ to $R_4$, $R_7$ to $R_9$, Y, n, $A_1$ and $A_2$ are the same as described above.)

Preferable specific examples of the compound of the present invention include the compound represented by the following general formula (1').

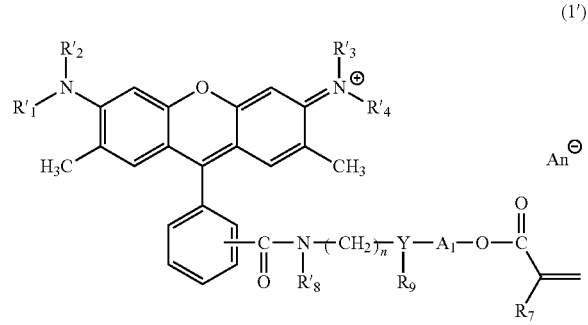
(1')

(wherein $R'_1$ to $R'_4$ and $R'_8$ each independently represent a hydrogen atom or an alkyl group having 1 to 6 carbon atoms; $R_7$, $R_9$, Y, n, $A_1$ and $An^-$ are the same as described above; $R'_8$ and $R_9$ may form a cyclic structure of a 5 to 6 membered ring together with —N—$(CH_2)_n$—Y— bonding thereto.)

The alkyl group having 1 to 6 carbon atoms, in $R'_1$ to $R'_4$ and $R'_8$ of the general formula (1'), includes the same one as the alkyl group having 1 to 6 carbon atoms, in $R_9$ of the general formula (1), and the preferable ones are also the same.

In the case where $R'_8$ and $R_9$ of the general formula (1') form a cyclic structure of a 5 to 6 membered ring together with —N—$(CH_2)_n$—Y— bonding thereto, the cyclic structure is the one represented by the general formula (1-2).

Among specific examples of $R'_1$ and $R'_4$ in the general formula (1'), a hydrogen atom, a methyl group, an ethyl group and a propyl group are preferable, and a hydrogen atom is more preferable.

As $R'_8$ in the general formula (1'), a hydrogen atom, or the case where $R_8$ and $R_9$ form a cyclic structure of a 5 to 6 membered ring together with —N—$(CH_2)_n$—Y— bonding thereto is preferable, and a hydrogen atom is more preferable. Specifically, it includes a hydrogen atom, a methyl group, an ethyl group, a propyl group, an isopropyl group, a butyl group, a pentyl group, a hexyl group, and the case where the cyclic structure, represented by the general formula (1-2) as described below is formed; and a hydrogen atom, a methyl group, an ethyl group, a propyl group, and the case where the structure included as the specific example of the cyclic structure, represented by the general formula (1-2) as described below is formed, are preferable; and a hydrogen atom, and the case where the structure included as the preferable specific example of the cyclic structure, represented by the after-mentioned general formula (1-2) as described below is formed, are more preferable; and a hydrogen atom is particularly preferable.

Among specific examples of $R'_2$ and $R'_3$ in the general formula (1'), a methyl group, an ethyl group and a propyl group are preferable, and an ethyl group is more preferable.

Preferable specific examples among the compound represented by the general formula (1') include the compound represented by the following general formula (1").

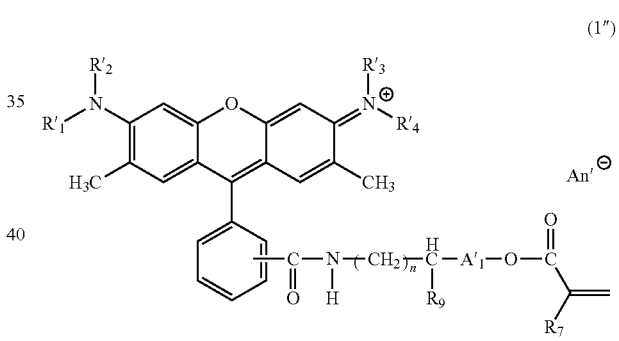
(1")

(wherein $A'_1$ represents an alkylene group having 1 to 21 carbon atoms which has at least one group selected from —O—, —OCO—, —COO—, —NHCO—, —CONH—, —NHCONH— and an arylene group in the chain; $An'^-$ represents an anion containing an aryl group having a halogeno group, a sulfonyl group having a halogeno group, or a halogenated alkyl group; $R'_1$ to $R'_4$, $R_7$, $R_9$ and n are the same as described above.)

"An alkylene group having 1 to 21 carbon atoms which has at least one group selected from —O—, —OCO—, —COO—, —NHCO—, —CONH—, —NHCONH— and an arylene group in the chain", in $A'_1$ of the general formula (1"), includes the same one as "an alkylene group having 1 to 21 carbon atoms which has at least one group selected from —O—, —OCO—, —COO—, —NHCO—, —CONH—, —NHCONH— and an arylene group in the chain", in $A_1$ of the general formula (1), and the preferable ones are also the same.

An anion moiety in the anion containing the aryl group having the halogeno group, the sulfonyl group having the halogeno group or the halogenated alkyl group, represented by $An'^-$ of the general formula (1"), includes the same one as the anion moiety in the anion of the present invention, and the preferable ones are also the same.

As the halogeno group in the aryl group having the halogeno group or the sulfonyl group having the halogeno group, represented by An'$^-$ of the general formula (1"), includes, for example, a fluoro group, a chloro group, a bromo group, or an iodo group, and a fluoro group is preferable.

As the aryl group in the aryl group having the halogeno group, represented by An'$^-$ of the general formula (1"), includes, for example, a phenyl group, a naphthyl group, and the like, and a phenyl group is preferable.

Specific examples of the aryl groups having a halogeno group, represented by An'$^-$ of the general formula (1"), include, for example, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a periodophenyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthyl group, a perbromonaphthyl group, a monoiodonaphthyl group, a diiodonaphthyl group, a triiodonaphthyl group, a periodonaphthyl group, and the like; a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group and a periodophenyl group are preferable; a difluorophenyl group, a trifluorophenyl group and a perfluorophenyl group are more preferable; and a perfluorophenyl group is particularly preferable.

The sulfonyl group having the halogeno group, represented by An'$^-$ of the general formula (1"), includes, for example, —SO$_2$—F, —SO$_2$—Cl, —SO$_2$—Br, —SO$_2$—I, and the like.

The halogenated alkyl group represented by An'$^-$ of the general formula (1") includes the same one as the halogenated alkyl group in the anion of the present invention, and the preferable ones are also the same.

The anions containing the aryl group having a halogeno group, the sulfonyl group having a halogeno group, or the halogenated alkyl, represented by An'$^-$ of the general formulae (1"), specifically include, for example, those represented by the following general formulae (13') to (18').

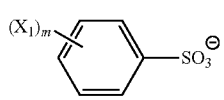

(13')

(wherein m is the same as described above; m pieces of X$_1$ each independently represent a halogen atom.)

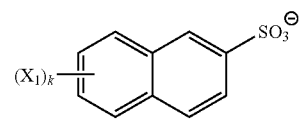

(14')

(wherein X$_1$ and k are the same as described above; k pieces of X$_1$ may be the same or different.)

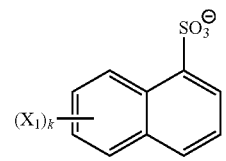

(15')

(wherein X$_1$ and k are the same as described above; k pieces of X$_1$ may be the same or different.)

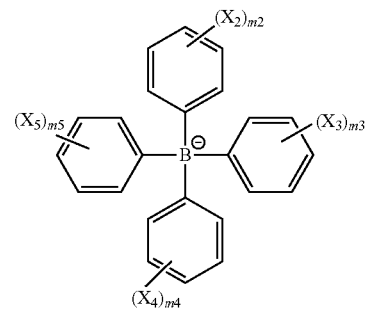

(16')

(wherein X$_2$ to X$_5$ each independently represent a halogen atom, m$_2$ to m$_5$ are the same as described above; m$_2$ pieces of X$_2$ may be the same or different, m$_3$ pieces of X$_3$, m$_4$ pieces of X$_4$, and m$_5$ pieces of X$_5$ may also be the same or different.)

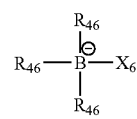

(17')

(wherein X$_6$ represents a halogen atom, R$_{46}$ is the same as described above, and at least one of three R$_{46}$ represents a halogenated alkyl group having 1 to 3 carbon atoms.)

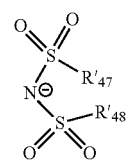

(18')

(wherein R'$_{47}$ and R'$_{48}$ each independently represent a halogen atom, or R'$_{47}$ together with R'$_{48}$ form a halogenated alkylene group having 2 to 3 carbon atoms)

The halogen atom in $X_1$ to $X_6$, $R'_{47}$ and $R'_{48}$ of the general formulae (13') to (18') includes a fluorine atom, a chlorine atom, a bromine atom, an iodine atom, and the like, and among them, a fluorine atom is preferable.

It is preferable that m pieces of $X_1$ in the general formula (13') are all the same.

Preferable specific examples of the anion represented by the general formula (13') include, for example, the following ones.

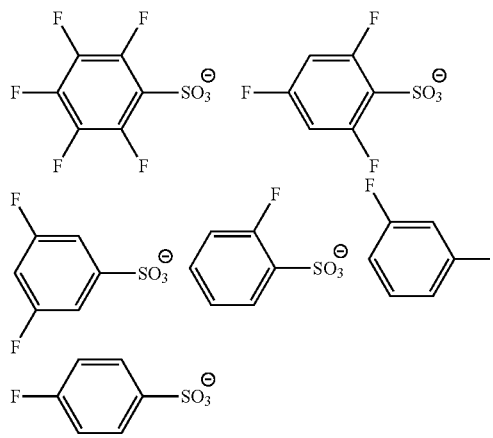

It is preferable that k pieces of $X_1$ in the general formulae (14') and (15') are all the same.

Preferable specific examples of the anion represented by the general formulae (14') and (15') include, for example, the following ones.

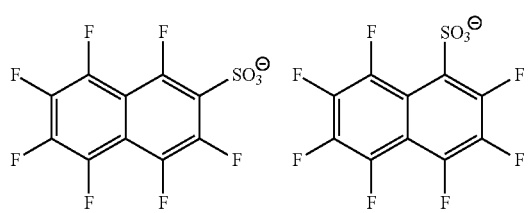

It is preferable that $m_2$ pieces of $X_2$, $m_3$ pieces of $X_3$, $m_4$ pieces of $X_4$ and $m_5$ pieces of $X_5$ in the general formula (16') are all the same.

Preferable specific examples of the anion represented by the general formula (16') include, for example, the following ones.

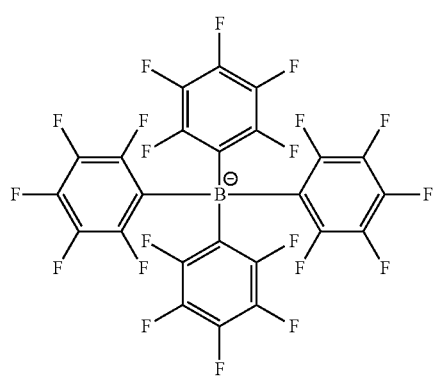

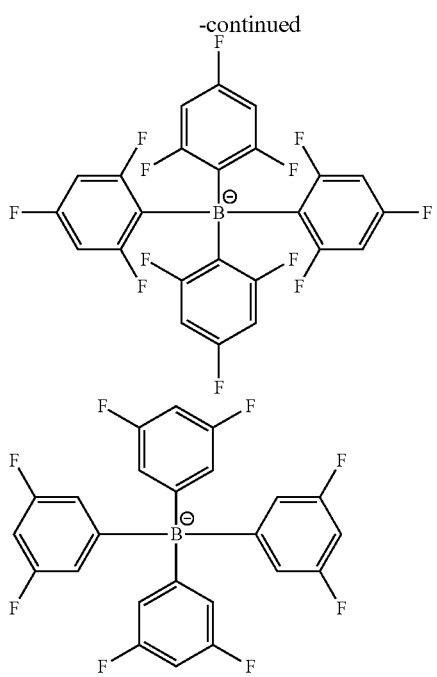

Among the above-described specific examples, the following one is more preferable.

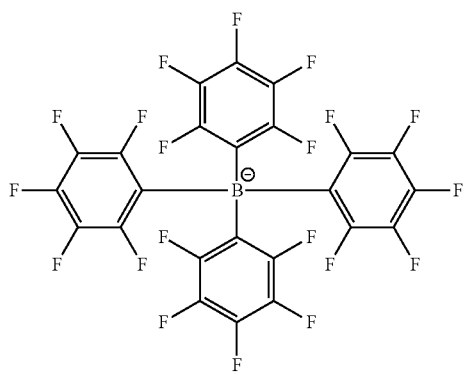 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

Preferable specific examples of the anion represented by the general formula (17') include, for example, $CF_3BF_3$, $CF_2F_5BF_3$, $C_3F_7BF_3$, and the like.

The halogenated alkylene group having 2 to 3 carbon atoms, formed by $R'_{47}$ together with $R'_{48}$ of the general formula (18'), includes, for example, a tetrafluoroethylene group, a hexafluoropropylene group, and the like, and a hexafluoropropylene group is preferable.

Preferable specific examples of the anions represented by the general formula (18') include, for example, the following ones.

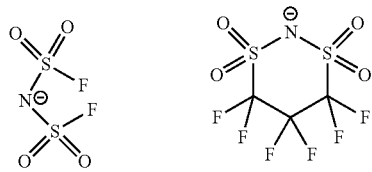

As the anion of the present invention, the one represented by the general formula (16'), the general formula (17'), or the general formula (18') is preferable, and the one represented by the general formula (16'), or the general formula (18') is more preferable, and the one represented by the general formula (16') is particularly preferable.

More specifically, among the specific examples of the anions of the present invention, the following ones are more preferable.

formulae (P) and (Q) in the $A'_1$ column represent the groups represented by the following formulae (P) and (Q).

$$-O-CO-(CH_2)_2-CO-O-(CH_2)_2- \quad (P)$$

$$-NHCONH-(CH_2)_2- \quad (Q)$$

| $R_1'$ | $R_2'$ | $R_3'$ | $R_4'$ | $R_7$ | $R_9$ | n | $A_1'$ |
|---|---|---|---|---|---|---|---|
| Hydrogen atom | Methyl group | Methyl group | Hydrogen atom | Hydrogen atom or methyl group | Hydrogen atom | 1 | Formula (P) or formula (Q) |
| Hydrogen atom | Ethyl group | Ethyl group | Hydrogen atom | | Hydrogen atom | 1 | |
| Hydrogen atom | Ethyl group | Ethyl group | Hydrogen atom | | Methyl group | 1 | |
| Hydrogen atom | Ethyl group | Ethyl group | Hydrogen atom | | Hydrogen atom | 2 | |
| Hydrogen atom | n-propyl group | n-propyl group | Hydrogen atom | | Hydrogen atom | 1 | |
| Hydrogen atom | Isopropyl group | Isopropyl group | Hydrogen atom | | Hydrogen atom | 1 | |
| Methyl group | Methyl group | Methyl group | Methyl group | | Hydrogen atom | 1 | |
| Methyl group | Ethyl group | Ethyl group | Methyl group | | Hydrogen atom | 1 | |
| Methyl group | n-propyl group | n-propyl group | Methyl group | | Hydrogen atom | 1 | |
| Methyl group | Isopropyl group | Isopropyl group | Methyl group | | Hydrogen atom | 1 | |
| Ethyl group | Ethyl group | Ethyl group | Ethyl group | | Hydrogen atom | 1 | |
| Ethyl group | n-propyl group | n-propyl group | Ethyl group | | Hydrogen atom | 1 | |
| Ethyl group | Isopropyl group | Isopropyl group | Ethyl group | | Hydrogen atom | 1 | |
| n-propyl group | n-propyl group | n-propyl group | n-propyl group | | Hydrogen atom | 1 | |

$An'^-$ used together with the combinations of the table includes, for example, the following ones.

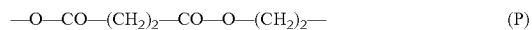

Among the above-described specific examples, the following one is particularly preferable.

Preferable combinations of $R'_1$ to $R'_4$, $R_7$, $R_9$, n and $A'_1$ in the general formula (1") include, for example, those described in the following table. It should be noted that

[Production Method for the Compound of the Present Invention]

Among the compound of the present invention, for example, the one where $R_8$ in the general formula (1) is a hydrogen atom, and Y is the group represented by the formula (1-1) {the compound represented by the following general formula (1-3)} can be produced by a method shown in the next scheme [I]. That is, after a reaction between a compound represented by the following general formula (31) and a compound represented by the following general formula (32) to obtain a compound represented by the following general formula (33), followed by a reaction between the compound represented by the general formula (33) and a compound represented by the following general formula (34) in the presence of a dehydration condensation agent, the resulting compound represented by the following general formula (36) may be subjected to salt formation reaction.

In addition, in the reaction to obtain the compound represented by the general formula (36) from the compound represented by the general formula (33), the compound represented by the general formula (36) can also be obtained by a reaction of the compound represented by the general formula (33) and a compound represented by the following general formula (35), instead of the method for using the compound represented by the general formula (34).

atoms which has at least one group selected from —O—, —OCO—, —COO—, —NHCO—, —CONH—, —NHCONH— and an arylene group in the chain, and also has a hydroxy group as a substituent; an alkylene group having 1 to 21 carbon atoms which has a hydroxy group as a substituent; or an alkylene group having 1 to 21 carbon atoms; and $Z^-$ represents an anion.)

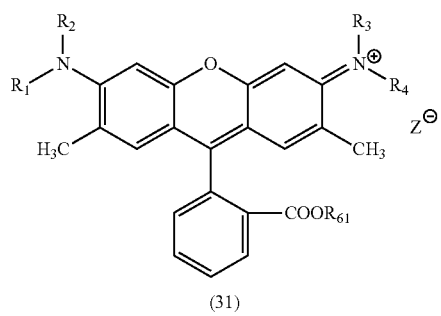

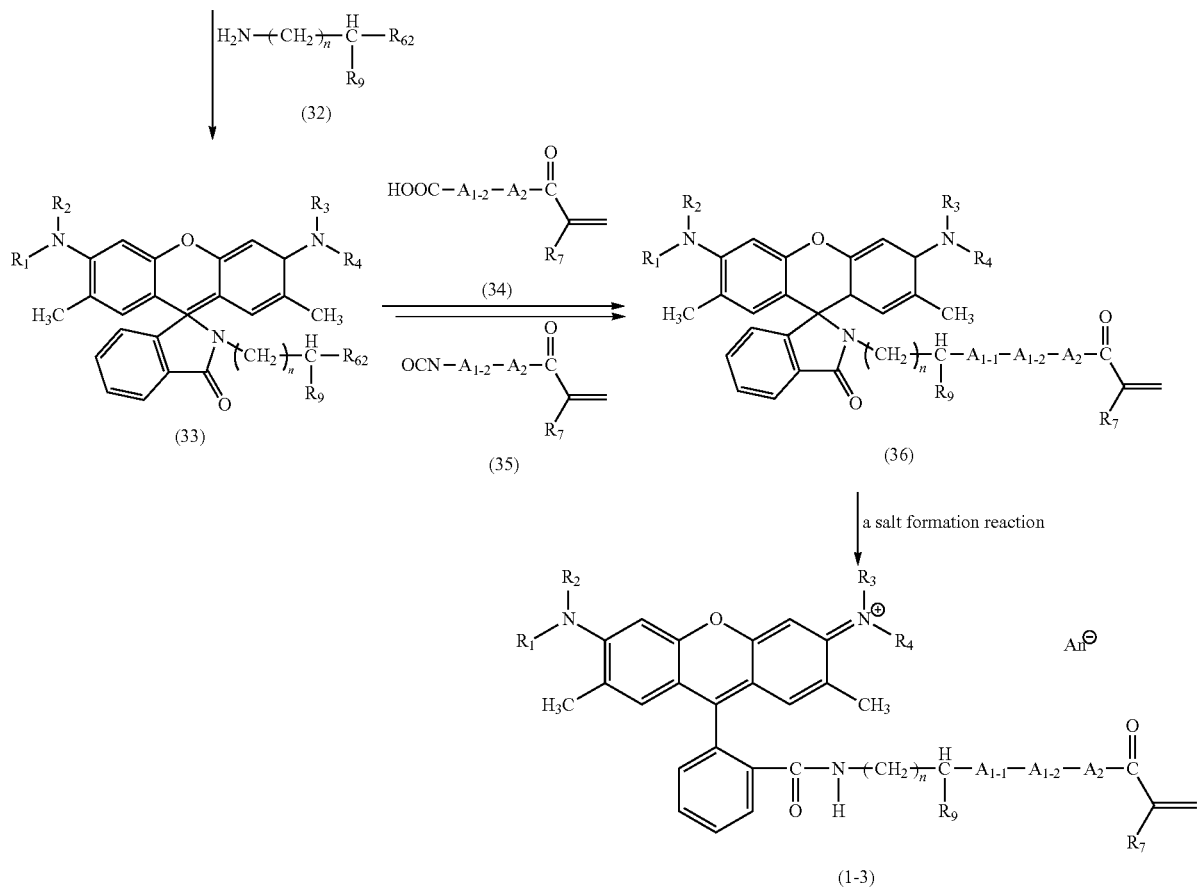

(in the scheme, $R_1$ to $R_4$, $R_7$, $R_9$, n, $A_2$ and An are the same as described above; $R_{61}$ represents an alkyl group having 1 to 6 carbon atoms; $R_{62}$ represents a hydroxy group or an amino group; $A_{1-1}$ represents —OCO—, —NHCO—, —OCONH— or —NHCONH—; $A_{1-2}$ represents an alkylene group having 1 to 21 carbon atoms which has at least one group selected from —O—, —OCO—, —COO—, —NHCO—, —CONH—, —NHCONH— and an arylene group in the chain; an alkylene group having 1 to 21 carbon The anion represented by $Z^-$ in the general formula (31) includes $Cl^-$, $NO_3^-$, $SO_4^{2-}$, $HSO_4^-$, $ClO_4^-$ and the anion of the present invention, and the like, and among them, $Cl^-$ is preferable.

The alkyl group having 1 to 6 carbon atom in $R_{61}$ of the general formula (31) includes the same one as the alkyl group having 1 to 6 carbon atom in $R_9$ of the general formula (1), and the preferable ones are also the same.

$A_{1-1}$ in the general formulae (36) and (1-3) is specified by the kind of a compound reacted with the general formula (33), and the kind of $R_{62}$, and the combinations thereof are shown in the following table.

| $A_{1-1}$ | Compound subjected to a reaction with the general formula (33) | $R_{62}$ |
|---|---|---|
| —OCO— | Compound represented by the general formula (34) | Hydroxyl group |
| —NHCO— | | Amino group |
| —OCONH— | Compound represented by the general formula (35) | Hydroxyl group |
| —NHCONH— | | Amino group |

The alkylene group having 1 to 21 carbon atom in "an alkylene group having 1 to 21 carbon atoms which has at least one group selected from —O—, —OCO—, —COO—, —NHCO—, —CONH—, —NHCONH— and an arylene group in the chain", "an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", "an alkylene group having 1 to 21 carbon atoms which has a hydroxy group as a substituent", and "an alkylene group having 1 to 21 carbon atoms", in $A_{1-2}$ of the general formulae (34) to (36) and (1-3), includes the same one as the alkylene group having 1 to 21 carbon atom in $A_1$ of the general formula (1), and the preferable ones are also the same.

The arylene group in "an alkylene group having 1 to 21 carbon atoms which has at least one group selected from —O—, —OCO—, —COO—, —NHCO—, —CONH—, —NHCONH— and an arylene group in the chain", and "an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", in $A_{1-2}$ of the general formulae (34) to (36) and (1-3), includes the one having 6 to 10 carbon atoms, and specifically includes a phenylene group, a naphthylene group, and the like.

"An alkylene group having 1 to 21 carbon atoms which has at least one group selected from —O—, —OCO—, —COO—, —NHCO—, —CONH—, —NHCONH— and an arylene group in the chain" in $A_{1-2}$ of the general formulae (34) to (36) and (1-3) includes, for example, the groups represented by the following general formulae (24-1) to (24-3), and the like.

$$-(R_{51}-O)_{h11}-R_{51}- \qquad (24-1)$$

(wherein $h_{11}$ represents an integer of 1 to 9, $R_{51}$ is the same as described above, and total number of carbon atoms in the formula is 1 to 21.)

$$-R_{52}-COO-(CH_2)_{h5}- \qquad (24-2)$$

(wherein $R_{52}$ and $h_5$ are the same as described above.)

The group represented by the general formula (24-1) includes specifically, for example,
—CH$_2$CH$_2$—O—(CH$_2$)$_2$—, —(CH$_2$CH$_2$—O)$_2$—(CH$_2$)$_2$—,
—(CH$_2$CH$_2$—O)$_3$—(CH$_2$)$_2$—, —(CH$_2$CH$_2$—O)$_4$—(CH$_2$)$_2$—,
—(CH$_2$CH$_2$—O)$_5$—(CH$_2$)$_2$—, —(CH$_2$CH$_2$—O)$_6$—(CH$_2$)$_2$—,
—(CH$_2$CH$_2$—O)$_7$—(CH$_2$)$_2$—, —(CH$_2$CH$_2$—O)$_8$—(CH$_2$)$_2$—,
—(CH$_2$CH$_2$—O)$_9$—(CH$_2$)$_2$—,
—CH$_2$CH(CH$_3$)—O—CH$_2$CH(CH$_3$)—,
—(CH$_2$CH(CH$_3$)—O)$_2$—CH$_2$CH(CH$_3$)—,
—(CH$_2$CH(CH$_3$)—O)$_3$—CH$_2$CH(CH$_3$)—,
—(CH$_2$CH(CH$_3$)—O)$_4$—CH$_2$CH(CH$_3$)—,
—(CH$_3$CH(CH$_3$)—O)$_5$—CH$_2$CH(CH$_3$)—,
—(CH$_2$CH(CH$_3$)—O)$_6$—CH$_2$CH(CH$_3$)—,
—(CH$_2$CH(CH$_3$)—O)$_7$—CH$_2$CH(CH$_3$)—,
—CH(CH$_3$)CH$_2$—O—CH(CH$_3$)CH$_2$—,
—(CH(CH$_3$)CH$_2$—O)$_2$—CH(CH$_3$)CH$_2$—,
—(CH(CH$_3$)CH$_2$—O)$_3$—CH(CH$_3$)CH$_2$—,
—(CH(CH$_3$)CH$_2$—O)$_4$—CH(CH$_3$)CH$_2$—,
—(CH(CH$_3$)CH$_2$—O)$_5$—CH(CH$_3$)CH$_2$—,
—(CH(CH$_3$)CH$_2$—O)$_6$—CH(CH$_3$)CH$_2$—,
—(CH(CH$_3$)CH$_2$—O)$_7$—CH(CH$_3$)CH$_2$—, and the like.

The group represented by the general formula (24-2) includes specifically, for example,
—CH$_2$—CO—O—CH$_2$—, —(CH$_2$)$_2$—CO—O—CH$_2$—,
—(CH$_2$)$_3$—CO—O—CH$_2$—, —(CH$_2$)$_4$—CO—O—CH$_2$—,
—(CH$_2$)$_5$—CO—O—CH$_2$—, —(CH$_2$)$_6$—CO—O—CH$_2$—,
—(CH$_2$)$_7$—CO—O—CH$_2$—,
—CH$_2$—CO—O—(CH$_2$)$_2$—,
—(CH$_2$)$_2$—CO—O—(CH$_2$)$_2$—,
—(CH$_2$)$_3$—CO—O—(CH$_2$)$_2$—,
—(CH$_2$)$_4$—CO—O—(CH$_2$)$_2$—,
—(CH$_2$)$_5$—CO—O—(CH$_2$)$_2$—,
—(CH$_2$)$_6$—CO—O—(CH$_2$)$_2$—,
—(CH$_2$)$_7$—CO—O—(CH$_2$)$_2$—,
—(CH$_2$)—CO—O—(CH$_2$)$_3$—,
—(CH$_2$)$_2$—CO—O—(CH$_2$)$_3$—,
—(CH$_2$)$_3$—CO—O—(CH$_2$)$_3$—,
—(CH$_2$)$_4$—CO—O—(CH$_2$)$_3$—,
—(CH$_2$)$_5$—CO—O—(CH$_2$)$_3$—,
—(CH$_2$)$_6$—CO—O—(CH$_2$)$_3$—,
—(CH$_2$)$_7$—CO—O—(CH$_2$)$_3$—,
—C$_6$H$_4$—CO—O—CH$_2$—, —C$_6$H$_4$—CO—O—(CH$_2$)$_2$—,
—C$_6$H$_4$—CO—O—(CH$_2$)$_3$—,
—C$_6$H$_{10}$—CO—O—CH$_2$—, —C$_6$H$_4$CO—O—(CH$_2$)$_2$—,
—C$_6$H$_4$CO—O—(CH$_2$)$_3$—, and the like; and among them,
—CH$_2$—CO—O—CH$_2$—, —(CH$_2$)$_2$—CO—O—CH$_2$—,
—(CH$_2$)$_3$—CO—O—CH$_2$—, —(CH$_2$)$_4$—CO—O—CH$_2$—,
—(CH$_2$)$_5$—CO—O—CH$_2$—, —(CH$_2$)$_6$CO—O—CH$_2$—,
—(CH$_2$)$_7$—CO—O—CH$_2$—,
—CH$_2$—CO—O—(CH$_2$)$_2$—,
—(CH$_2$)$_2$—CO—O—(CH$_2$)$_2$—,
—(CH$_2$)$_3$—CO—O—(CH$_2$)$_2$—,
—(CH$_2$)$_4$—CO—O—(CH$_2$)$_2$—,
—(CH$_2$)$_5$—CO—O—(CH$_2$)$_2$—,
—(CH$_2$)$_6$—CO—O—(CH$_2$)$_2$—,
—(CH$_2$)$_7$—CO—O—(CH$_2$)$_2$—,
—CH$_2$—CO—O—(CH$_2$)$_3$—,
—(CH$_2$)$_2$—CO—O—(CH$_2$)$_3$—,
—(CH$_2$)$_3$—CO—O—(CH$_2$)$_3$—,
—(CH$_2$)$_4$—CO—O—(CH$_2$)$_3$—,
—(CH$_2$)$_5$—CO—O—(CH$_2$)$_3$—,
—(CH$_2$)$_6$—CO—O—(CH$_2$)$_3$— and
—(CH$_2$)$_7$—CO—O—(CH$_2$)$_3$— are preferable; and
—CH$_2$—CO—O—(CH$_2$)$_2$—,
—(CH$_2$)$_2$—CO—O—(CH$_2$)$_2$—,
—(CH$_2$)$_3$—CO—O—(CH$_2$)$_2$—,
—(CH$_2$)$_4$—CO—O—(CH$_2$)$_2$—,
—(CH$_2$)$_5$—CO—O—(CH$_2$)$_2$—,
—(CH$_2$)$_6$—CO—O—(CH$_2$)$_3$— and
—(CH$_2$)$_7$—CO—O—(CH$_2$)$_2$— are more preferable; and
—(CH$_2$)$_2$—CO—O—(CH$_2$)$_2$— is particularly preferable.

"An alkylene group having 1 to 21 carbon atoms which has at least one group selected from —O—, —OCO—, —COO—, —NHCO—, —CONH—, —NHCONH— and an arylene group in the chain, and also has a hydroxy group as a substituent", in $A_{1-2}$ of the general formulae (34) to (36) and (1-3) includes the same one as "an alkylene group having 1 to 21 carbon atoms which has at least one group selected from —O—, —OCO—, —COO—, —NHCO—, —CONH—, —NHCONH— and an arylene group in the chain, and also has a hydroxy group as a substituent" in $A_1$ of the general formula (1), and the preferable ones are also the same.

The alkylene group having 1 to 21 carbon atoms which has a hydroxy group as a substituent, in $A_{1-2}$ of the general formulae (34) to (36) and (1-3) includes the same one as the alkylene group having 1 to 21 carbon atoms which has a hydroxy group as a substituent, in $A_1$ of the general formula (1), and the preferable ones are also the same.

As $A_{1-2}$ of the general formulae (34) to (36) and (1-3), "an alkylene group having 1 to 21 carbon atoms which has at least one group selected from —O—, —OCO—, —COO—, —NHCO—, —CONH—, —NHCONH— and an arylene group in the chain" and "an alkylene group having 1 to 21 carbon atoms" are preferable, and among them, the group represented by the general formula (24-2), and the alkylene group having 1 to 21 carbon atoms are preferable. Preferable specific examples of $A_{1-2}$ include a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group,
—$CH_2$—CO—O—$CH_2$—, —$(CH_2)_2$—CO—O—$CH_2$—,
—$(CH_2)_3$—CO—O—$CH_2$—, —$(CH_2)_4$—CO—O—$CH_2$—,
—$(CH_3)_5$—CO—O—$CH_2$—, —$(CH_2)_6$—CO—O—$CH_2$—,
—$(CH_2)_7$—CO—O—$CH_2$—,
—$CH_2$—CO—O—$(CH_2)_2$—,
—$(CH_2)_2$—CO—O—$(CH_2)_2$—,
—$(CH_2)_3$—CO—O—$(CH_2)_2$—,
—$(CH_2)_4$—CO—O—$(CH_2)_2$—,
—$(CH_2)_5$—CO—O—$(CH_2)_2$—,
—$(CH_2)_6$—CO—O—$(CH_2)_2$—,
—$(CH_2)_7$—CO—O—$(CH_2)_2$—,
—$CH_2$—CO—O—$(CH_2)_3$—,
—$(CH_2)_2$—CO—O—$(CH_2)_3$—,
—$(CH_2)_3$—CO—O—$(CH_2)_3$—,
—$(CH_2)_4$—CO—O—$(CH_2)_3$—,
—$(CH_2)_5$—CO—O—$(CH_2)_3$—,
—$(CH_2)_6$—CO—O—$(CH_2)_3$—,
—$(CH_2)_7$—CO—O—$(CH_2)_3$—,
and the like; and a methylene group, an ethylene group, a propylene group,
—$CH_2$—CO—O—$(CH_2)_2$—,
—$(CH_2)_2$—CO—O—$(CH_2)_2$—,
—$(CH_2)_3$—CO—O—$(CH_2)_2$—,
—$(CH_2)_4$—CO—O—$(CH_2)_2$—,
—$(CH_3)_5$—CO—O—$(CH_2)_2$—,
—$(CH_2)_6$—CO—O—$(CH_2)_2$— and
—$(CH_2)_7$—CO—O—$(CH_2)_2$—
are more preferable; and an ethylene group and
—$(CH_2)_2$—CO—O—$(CH_2)_2$—
are particularly preferable.

The group where $A_{1-1}$ and $A_{1-2}$ are combined in the scheme [I] provides $A_1$ in the compound of the present invention. In this case, total number of carbon atoms contained in $A_{1-1}$ and $A_{1-2}$ is 1 to 21.

Preferable specific examples of the compound represented by the general formula (1-3) include the compound represented by the following general formula (1'-3).

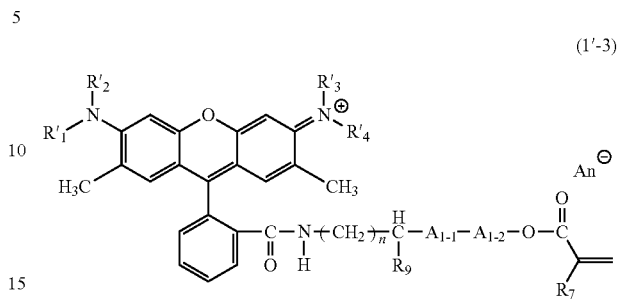

(1'-3)

(wherein $R'_1$ to $R'_4$, $R_7$, $R_9$, n, $A_{1-1}$, $A_{1-2}$ and $An^-$ are the same as described above.)

Preferable specific examples of the compound represented by the general formula (1'-3) include the compound represented by the following general formula (1"-3).

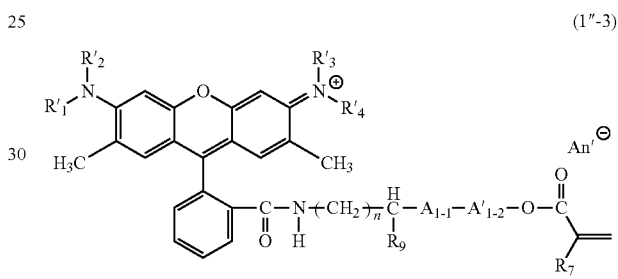

(1"-3)

(wherein $R'_1$ to $R'_4$, $R_7$, $R_9$, n, $A_{1-1}$ and $An'^-$ are the same as described above; $A'_{1-2}$ represents an alkylene group having 1 to 21 carbon atoms which has at least one group selected from —O—, —OCO—, —COO—, —NHCO—, —CONH—, —NHCONH— and an arylene group in the chain; or an alkylene group having 1 to 21 carbon atoms.)

The alkylene group having 1 to 21 carbon atoms in "an alkylene group having 1 to 21 carbon atoms which has at least one group selected from —O—, —OCO—, —COO—, —NHCO—, —CONH—, —NHCONH— and an arylene group in the chain", and "an alkylene group having 1 to 21 carbon atoms", in $A'_{1-2}$ of the general formula (1"-3), includes the same one as the alkylene group having 1 to 21 carbon atom, in $A_1$ of the general formula (1), and the preferable ones are also the same.

"An alkylene group having 1 to 21 carbon atoms which has at least one group selected from —O—, —OCO—, —COO—, —NHCO—, —CONH—, —NHCONH— and an arylene group in the chain", in $A'_{1-2}$ of the general formula (1"-3), includes the same one as "an alkylene group having 1 to 21 carbon atoms which has at least one group selected from —O—, —OCO—, —COO—, —NHCO—, —CONH—, —NHCONH— and an arylene group in the chain", in $A_{1-2}$ of the general formula (1-3), and the preferable ones are also the same.

Preferable specific examples of $A'_{1-2}$ in the general formula (1"-3) include the same ones as the preferable specific examples of $A_{1-2}$ in the general formula (1-3), and the more preferable ones are also the same.

Preferable combinations of $R'_1$ to $R'_4$, $R_7$, $R_9$, n, $A_{1-1}$ and $A_{1-2}$ of the general formula (1"-3) include, for example, those described in the following table. It should be noted that formula (P') in the $A'_{1-2}$ column represents the group represented by the following formula (P).

$$—(CH_2)_2—CO—O—(CH_2)_2—\quad (P')$$

and an alkylenediamine such as methylenediamine, ethylenediamine, propylenediamine, methylethylenediamine, butylenediamine, 1-methylpropylenediamine, 2-methylpropylenediamine, pentylenediamine, methylbuty-

| $R_1'$ | $R_3'$ | $R_5'$ | $R_6'$ | $R_7$ | $R_8$ | n | $A_{1-1}$ | $A'_{1-3}$ |
|---|---|---|---|---|---|---|---|---|
| Hydrogen atom | Methyl group | Methyl group | Hydrogen atom | Hydrogen atom or methyl group | Hydrogen atom | 1 | —OCO— | Formula (P') |
|  | Methyl group | Methyl group |  |  | Hydrogen atom | 1 | —NHCONH— | Ethylene group |
|  | Ethyl group | Ethyl group |  |  | Hydrogen atom | 1 | —OCO— | Formula (P') |
|  | Ethyl group | Ethyl group |  |  | Hydrogen atom | 1 | —NHCONH— | Ethylene group |
|  | Ethyl group | Ethyl group |  |  | Methyl group | 1 | —OCO— | Formula (P') |
|  | Ethyl group | Ethyl group |  |  | Methyl group | 1 | —NHCONH— | Ethylene group |
|  | Ethyl group | Ethyl group |  |  | Hydrogen atom | 2 | —OCO— | Formula (P') |
|  | Ethyl group | Ethyl group |  |  | Hydrogen atom | 2 | —NHCONH— | Ethylene group |
|  | n-propyl group | n-propyl group |  |  | Hydrogen atom | 1 | —OCO— | Formula (P') |
|  | n-propyl group | n-propyl group |  |  | Hydrogen atom | 1 | —NHCONH— | Ethylene group |
|  | Isopropyl group | Isopropyl group |  |  | Hydrogen atom | 1 | —OCO— | Formula (P') |
|  | Isopropyl group | Isopropyl group |  |  | Hydrogen atom | 1 | —NHCONH— | Ethylene group |
| Methyl group | Methyl group | Methyl group | Methyl group |  | Hydrogen atom | 1 | —OCO— | Formula (P') |
|  | Methyl group | Methyl group |  |  | Hydrogen atom | 1 | —NHCONH— | Ethylene group |
|  | Ethyl group | Ethyl group |  |  | Hydrogen atom | 1 | —OCO— | Formula (P') |
|  | Ethyl group | Ethyl group |  |  | Hydrogen atom | 1 | —NHCONH— | Ethylene group |
|  | n-propyl group | n-propyl group |  |  | Hydrogen atom | 1 | —OCO— | Formula (P') |
|  | n-propyl group | n-propyl group |  |  | Hydrogen atom | 1 | —NHCONH— | Ethylene group |
|  | Isopropyl group | Isopropyl group |  |  | Hydrogen atom | 1 | —OCO— | Formula (P') |
|  | Isopropyl group | Isopropyl group |  |  | Hydrogen atom | 1 | —NHCONH— | Ethylene group |
| Ethyl group | Ethyl group | Ethyl group | Ethyl group |  | Hydrogen atom | 1 | —OCO— | Formula (P') |
|  | Ethyl group | Ethyl group |  |  | Hydrogen atom | 1 | —NHCONH— | Ethylene group |
|  | n-propyl group | n-propyl group |  |  | Hydrogen atom | 1 | —OCO— | Formula (P') |
|  | n-propyl group | n-propyl group |  |  | Hydrogen atom | 1 | —NHCONH— | Ethylene group |
|  | Isopropyl group | Isopropyl group |  |  | Hydrogen atom | 1 | —OCO— | Formula (P') |
|  | Isopropyl group | Isopropyl group |  |  | Hydrogen atom | 1 | —NHCONH— | Ethylene group |
| n-propyl group | n-propyl group | n-propyl group | n-propyl group |  | Hydrogen atom | 1 | —OCO— | Formula (P') |
|  | n-propyl group | n-propyl group |  |  | Hydrogen atom | 1 | —NHCONH— | Ethylene group |

$An'^-$ used with the combinations includes the same one as $An'^-$ used with the preferable combinations of $R'_1$ to $R'_4$, $R_7$, $R_9$, n and $A'_1$ in the general formula (1").

Preferable combinations of $R_1$ to $R_4$, $R_{61}$ and Z of the general formula (31) include, for example, those described in the following table.

| $R_1$ | $R_2$ | $R_3$ | $R_4$ | $R_{61}$ | $Z^-$ |
|---|---|---|---|---|---|
| Hydrogen atom | Methyl group | Methyl group | Hydrogen atom | Ethyl group | $Cl^-$ |
| Hydrogen atom | Ethyl group | Ethyl group | Hydrogen atom | Methyl group | $Cl^-$ |
| Hydrogen atom | Ethyl group | Ethyl group | Hydrogen atom | Ethyl group | $Cl^-$ |
| Hydrogen atom | Ethyl group | Ethyl group | Hydrogen atom | n-propyl group | $Cl^-$ |
| Hydrogen atom | Ethyl group | Ethyl group | Hydrogen atom | Ethyl group | $NO_3^-$ |
| Hydrogen atom | Ethyl group | Ethyl group | Hydrogen atom | Ethyl group | $SO_4^{2-}$ |
| Hydrogen atom | Ethyl group | Ethyl group | Hydrogen atom | Ethyl group | $HSO_4^-$ |
| Hydrogen atom | Ethyl group | Ethyl group | Hydrogen atom | Ethyl group | $ClO_4^-$ |
| Hydrogen atom | n-propyl group | n-propyl group | Hydrogen atom | Ethyl group | $Cl^-$ |
| Hydrogen atom | Isopropyl group | Isopropyl group | Hydrogen atom | Ethyl group | $Cl^-$ |
| Methyl group | Methyl group | Methyl group | Methyl group | Ethyl group | $Cl^-$ |
| Methyl group | Ethyl group | Ethyl group | Methyl group | Ethyl group | $Cl^-$ |
| Methyl group | n-propyl group | n-propyl group | Methyl group | Ethyl group | $Cl^-$ |
| Methyl group | Isopropyl group | Isopropyl group | Methyl group | Ethyl group | $Cl^-$ |
| Ethyl group | Ethyl group | Ethyl group | Ethyl group | Ethyl group | $Cl^-$ |
| Ethyl group | n-propyl group | n-propyl group | Ethyl group | Ethyl group | $Cl^-$ |
| Ethyl group | Isopropyl group | Isopropyl group | Ethyl group | Ethyl group | $Cl^-$ |
| n-propyl group | n-propyl group | n-propyl group | n-propyl group | Ethyl group | $Cl^-$ |

Preferable specific examples of the general formula (32) include, for example, an amino alcohol such as aminomethanol, 2-aminoethanol, 3-aminopropanol, 2-amino-1-methylethanol, 4-aminobutanol, 3-amino-1-methylpropanol, 3-amino-2-methylpropanol, 5-aminopentanol, 4-amino-1-methylbutanol, 3-amino-1,2-dimethylpropanol, 3-amino-1-ethylpropanol, 6-aminohexanol and 5-amino-1-methylpen- lenediamine, 1,2-dimethylpropylenediamine, 1-ethylpropylenediamine, hexylenediamine and methylpentylenediamine. Among them, aminomethanol, 2-aminoethanol, 3-aminopropanol, 4-aminobutanol, 5-aminopentanol, 6-aminohexanol, methylenediamine, ethylenediamine, propylenediamine, butylenediamine, pentylenediamine and hexylenediamine are preferable; aminomethanol, 2-aminoethanol, 3-aminopropanol, methylenediamine, ethylenediamine and propylenediamine are more preferable; and 2-aminoethanol and ethylenediamine are particularly preferable.

Preferable specific examples of the compound represented by the general formula (33) include the compound represented by the following general formula (33').

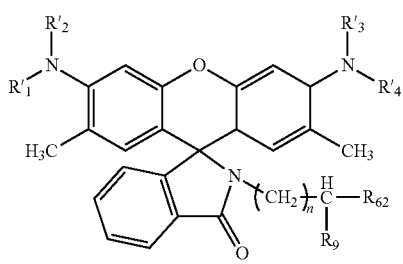

(33')

(wherein $R'_1$ to $R'_4$, $R_9$, $R_{62}$ and n are the same as described above.)

Preferable combinations of $R'_1$ to $R'_4$, $R_9$, $R_{62}$ and n of the general formula (33') include, for example, those described in the following table.

| $R_1'$ | $R_2'$ | $R_3'$ | $R_4'$ | $R_9$ | $R_{62}$ | n |
|---|---|---|---|---|---|---|
| Hydrogen atom | Methyl group | Methyl group | Hydrogen atom | Hydrogen atom | —OH or —NH$_2$ | 1 |
| Hydrogen atom | Ethyl group | Ethyl group | Hydrogen atom | Hydrogen atom | —OH or —NH$_2$ | 1 |
| Hydrogen atom | Ethyl group | Ethyl group | Hydrogen atom | Methyl group | —OH or —NH$_2$ | 1 |
| Hydrogen atom | Ethyl group | Ethyl group | Hydrogen atom | Hydrogen atom | —OH or —NH$_2$ | 2 |
| Hydrogen atom | Ethyl group | Ethyl group | Hydrogen atom | Hydrogen atom | —OH or —NH$_2$ | 1 |
| Hydrogen atom | Ethyl group | Ethyl group | Hydrogen atom | Hydrogen atom | —OH or —NH$_2$ | 1 |
| Hydrogen atom | Ethyl group | Ethyl group | Hydrogen atom | Hydrogen atom | —OH or —NH$_2$ | 1 |
| Hydrogen atom | n-propyl group | n-propyl group | Hydrogen atom | Hydrogen atom | —OH or —NH$_2$ | 1 |
| Hydrogen atom | Isopropyl group | Isopropyl group | Hydrogen atom | Hydrogen atom | —OH or —NH$_2$ | 1 |
| Methyl group | Methyl group | Methyl group | Methyl group | Hydrogen atom | —OH or —NH$_2$ | 1 |
| Methyl group | Ethyl group | Ethyl group | Methyl group | Hydrogen atom | —OH or —NH$_2$ | 1 |
| Methyl group | n-propyl group | n-propyl group | Methyl group | Hydrogen atom | —OH or —NH$_2$ | 1 |
| Methyl group | Isopropyl group | Isopropyl group | Methyl group | Hydrogen atom | —OH or —NH$_2$ | 1 |
| Ethyl group | Ethyl group | Ethyl group | Ethyl group | Hydrogen atom | —OH or —NH$_2$ | 1 |
| Ethyl group | n-propyl group | n-propyl group | Ethyl group | Hydrogen atom | —OH or —NH$_2$ | 1 |
| Ethyl group | Isopropyl group | Isopropyl group | Ethyl group | Hydrogen atom | —OH or —NH$_2$ | 1 |
| n-propyl group | n-propyl group | n-propyl group | n-propyl group | Hydrogen atom | —OH or —NH$_2$ | 1 |

Preferable specific examples of the general formula (34) include, for example, the following ones.

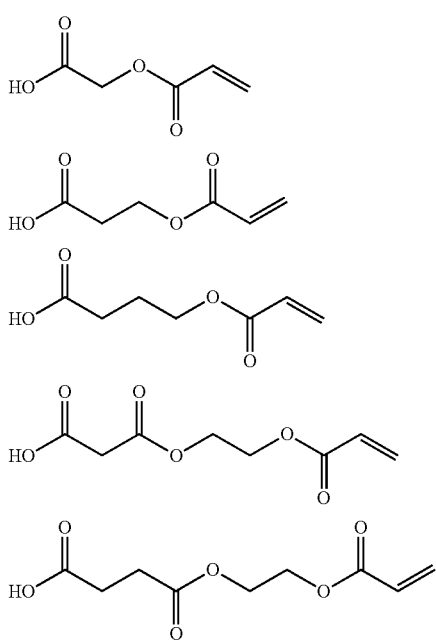

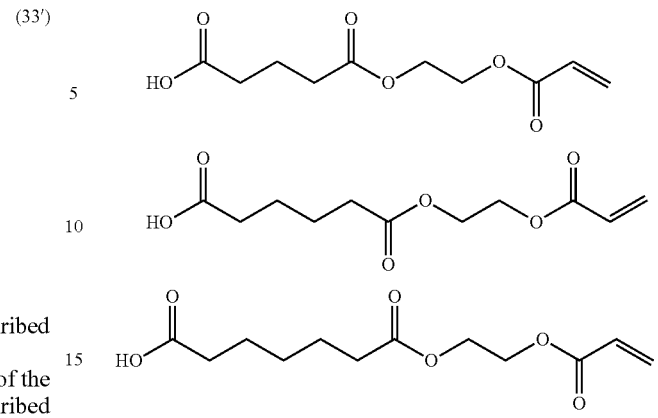

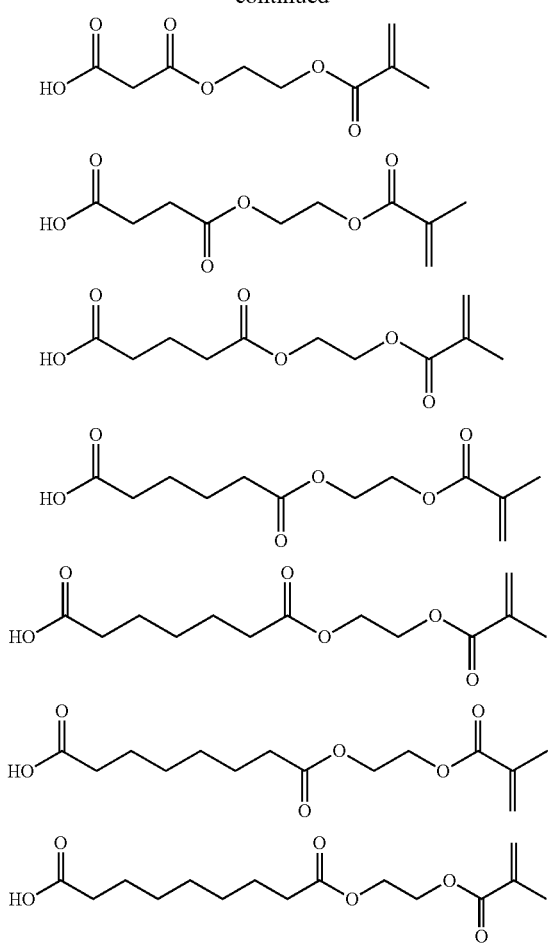
Preferable specific examples of the general formula (35) include, for example, the following ones.
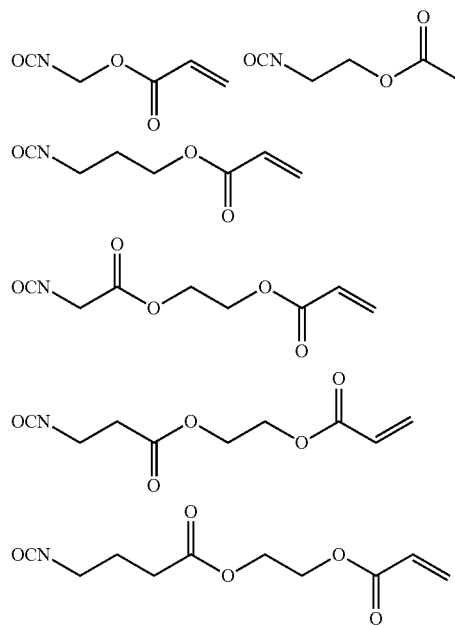
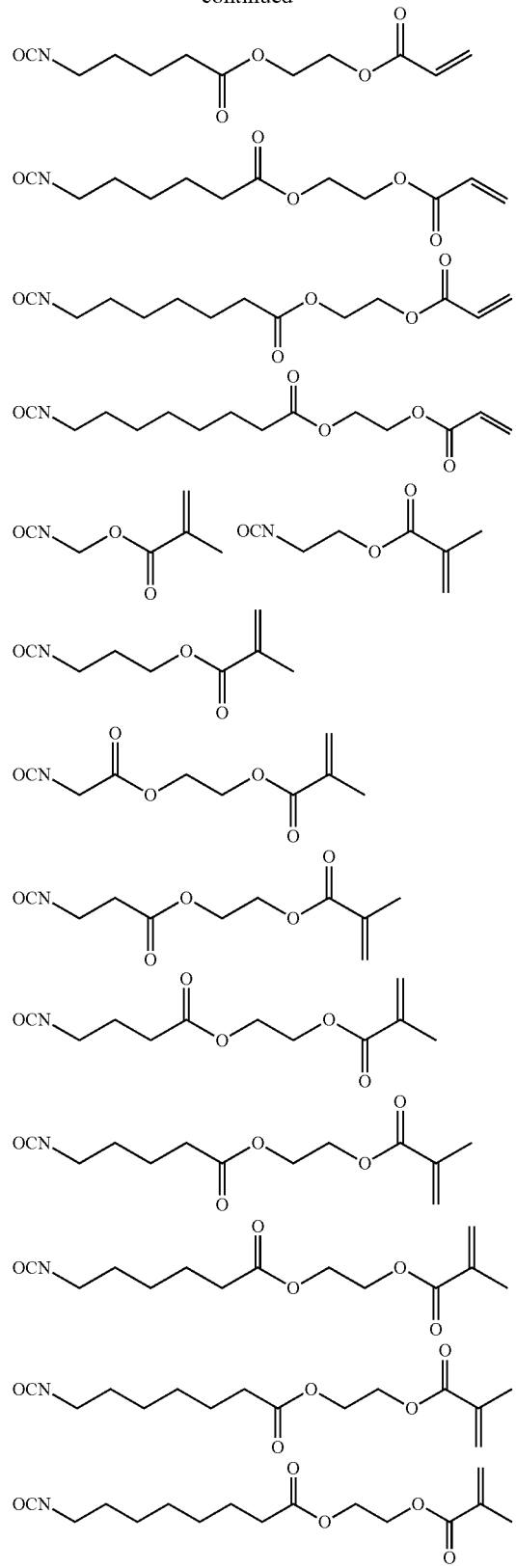
Preferable specific examples of the compound represented by the general formula (36) include the compound represented by the following general formula (36').

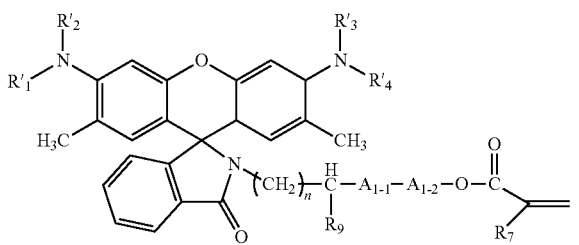

(36')

(wherein R'$_1$ to R'$_4$, R$_7$, R$_9$, n, A$_{1-1}$ and A$_{1-2}$ are the same as described above.)

More preferable specific examples among the compound represented by the general formula (36') include the compound represented by the following general formula (36").

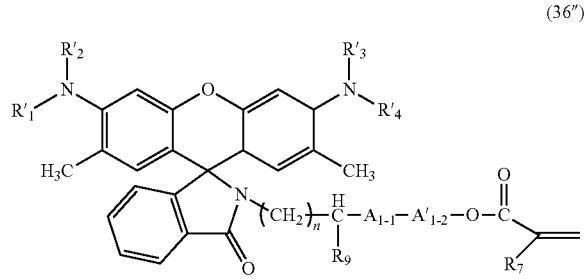

(36")

(wherein R'$_1$ to R'$_4$, R$_7$, R$_9$, n, A$_{1-1}$ and A'$_{1-2}$ are the same as described above.)

Preferable combinations of R'$_1$ to R'$_4$, R$_7$, R$_9$, n, A$_{1-1}$ and A'$_{1-2}$ of the general formula (36") include the same one as the preferable combinations of R'$_1$ to R'$_4$, R$_7$, R$_9$, n, A$_{1-1}$ and A'$_{1-2}$ of the general formula (1"-3).

In the reaction between the compound represented by the general formula (31) and the compound represented by the general formula (32), the compound represented by the general formula (31) and the compound represented by the general formula (32) may be reacted in a solvent, usually at 0 to 80° C., preferably at 10 to 50° C., for usually 1 to 24 hours, and preferably 1 to 8 hours.

The solvent in the reaction between the compound represented by the general formula (31) and the compound represented by the general formula (32) includes an organic solvent such as methanol, ethanol, isopropyl alcohol (IPA), tetrahydrofuran (THF), dioxane, N,N-dimethylformamide (DMF), methylene chloride, dichloroethane and among them, ethanol is preferable. They may be used alone, or in combination of two or more kinds thereof as appropriate. Use amount of the reaction solvent is usually 1 to 50 times volume, and preferably 1 to 20 times volume, relative to total volume of the compound represented by the general formula (31) and the compound represented by the general formula (32).

Use amount of the compound represented by the general formula (32) is usually 1 to 50 equivalent, and preferably 10 to 20 equivalent, relative to mole number of the compound represented by the general formula (31).

In the reaction between the compound represented by the general formula (33) and the compound represented by the general formula (34), the compound represented by the general formula (33) and the compound represented by the general formula (34) may be reacted in a solvent, in the presence of a dehydration condensation agent, usually at 0 to 80° C., preferably at 10 to 50° C., for usually 1 to 48 hours, and preferably 10 to 36 hours.

The solvent in the reaction between the compound represented by the general formula (33) and the compound represented by the general formula (34) includes ethers such as diethyl ether, diisopropyl ether, ethylmethyl ether, tetrahydrofuran, 1,4-dioxane and dimethoxyethane; ketones such as acetone, dimethyl ketone, methyl ethyl ketone, diethyl ketone, 2-hexanone, t-butyl methyl ketone, cyclopentanone and cyclohexanone; halogenated hydrocarbons such as chloromethane, methylene chloride, chloroform, dichloroethane, trichloroethane and chlorobenzene; hydrocarbons such as n-hexane, benzene, toluene and xylene; esters such as ethyl acetate, butyl acetate and methyl propionate; nitriles such as acetonitrile; amides such as N,N-dimethylformamide; and the like; and among them, halogenated hydrocarbons are preferable, and methylene chloride is more preferable. They may be used alone, or in combination of two or more kinds thereof as appropriate. Use amount of the reaction solvent is usually 1 to 50 times volume, and preferably 1 to 20 times volume, relative to total volume of the compound represented by the general formula (33) and the compound represented by the general formula (34).

The dehydration condensation agent in the reaction between the compound represented by the general formula (33) and the compound represented by the general formula (34) may be, for example, the one generally used as a dehydration condensation agent, and it includes, for example, inorganic dehydrating agents such as diphosphorus pentaoxide and anhydrous zinc chloride; carbodiimides such as dicyclohexylcarbodiimide, diisopropylcarbodiimide and 1-ethyl-3-(3-dimethylaminopropylcarbodiimide) hydrochloride; polyphosphoric acid; acetic anhydride; sulfuric acid; carbonyldiimidazole; p-toluenesulfonic acid; and the like; and carbodiimides are preferable. Use amount of the dehydration condensation agent is usually 1 to 10 equivalent, and preferably 1 to 5 equivalent, relative to mole number of the compound represented by the general formula (33). In the reaction between the compound represented by the general formula (33) and the compound represented by the general formula (34), a catalyst, such as dimethylaminopyridine, may be used to enhance the efficiency of the dehydration condensation agent. Use amount of the catalyst is usually 0.1 to 10 equivalent, relative to mole number of the compound represented by the general formula (33).

Use amount of the compound represented by the general formula (34) is usually 1 to 2 equivalent, and preferably 1 to 1.5 equivalent, relative to mole number of the compound represented by the general formula (33).

The salt formation reaction in the scheme [I] is carried out by contacting a salt of the anion of the present invention with the compound represented by the general formula (36), in a solvent.

The solvent in the salt formation reaction includes an organic solvent such as methanol, ethanol, isopropyl alcohol (IPA), tetrahydrofuran (THF), dioxane, N,N-dimethylformamide (DMF), methylene chloride, dichloroethane, and among them, ethanol is preferable. They may be used alone, or in combination of two or more kinds thereof as appropriate. Use amount of the reaction solvent is usually 1 to 50 times volume, preferably 1 to 20 times volume, relative to volume of the compound represented by the general formula (36).

The salt formation reaction may be carried out usually at 0 to 100° C., preferably at 30 to 80° C., for usually 1 to 12 hours, and preferably 1 to 8 hours.

The salt of the anion of the present invention in the salt formation reaction includes a sodium salt, a potassium salt, a lithium salt, and the like, of the anion of the present invention, and a potassium salt or a lithium salt is preferable. Use amount of the salt of the anion of the present invention is usually 1 to 2 equivalent, preferably 1 to 1.5 equivalent, relative to mole number of the compound represented by the general formula (36).

The reaction between the compound represented by the general formula (33) and the compound represented by the general formula (35) may be carried out in a solvent, usually at 0 to 80° C., preferably at 10 to 50° C., for usually 1 to 24 hours, and preferably 1 to 8 hours.

The solvent in the reaction between the compound represented by the general formula (33) and the compound represented by the general formula (35) includes ethers such as diethyl ether, diisopropyl ether, ethylmethyl ether, tetrahydrofuran, 1,4-dioxane and dimethoxyethane; ketones such as acetone, dimethyl ketone, methyl ethyl ketone, diethyl ketone, 2-hexanone, t-butyl methyl ketone, cyclopentanone and cyclohexanone; halogenated hydrocarbons such as chloromethane, methylene chloride, chloroform, dichloroethane, trichloroethane and chlorobenzene; hydrocarbons such as n-hexane, benzene, toluene and xylene; esters such as ethyl acetate, butyl acetate and methyl propionate; nitriles such as acetonitrile; amides such as N,N-dimethylformamide; and the like; and among them, ethers, halogenated hydrocarbons and hydrocarbons are preferable, and tetrahydrofuran, methylene chloride, toluene, and the like, are more preferable. They may be used alone, or in combination of two or more kinds thereof as appropriate. Use amount of the reaction solvent is usually 1 to 50 times volume, and preferably 1 to 20 times volume, relative to total volume of the compound represented by the general formula (33) and the compound represented by the general formula (35).

Use amount of the compound represented by the general formula (35) is usually 1 to 2 equivalent, and preferably 1 to 1.5 equivalent, relative to mole number of the compound represented by the general formula (33).

Pressure in a series of the above-described reactions is not especially limited, as long as the series of the reactions is carried out without delay, and the reactions may be carried out, for example, under ambient pressure.

Resulting reactants and products after the series of the reactions can be isolated by a general post-treatment operation and purification operation usually carried out in this field. Specifically, for example, the resulting reactants and products may be isolated, as needed, by filtration, washing, extraction, concentration under reduced pressure, recrystallization, distillation, column chromatography, and the like.

Among the compound of the present invention, for example, the one where $R_8$ is an alkyl group having 1 to 30 carbon atoms, or the one where $R_8$ and $R_9$ form a cyclic structure of a 5 to 6 membered ring together with —N—$(CH_2)_n$—Y— bonding thereto {a compound represented by the following general formula (1-4)} can be produced by a method shown in the next scheme [II]. That is, after hydrolysis of a compound represented by the following general formula (31), a resulting acid derived from the compound represented by the general formula (31) and a compound represented by the following general formula (37) are reacted to obtain an intermediate represented by the following general formula (38). Then, after a reaction between the intermediate represented by the general formula (38) and a compound represented by the following general formula (39), and a salt formation reaction, a resulting compound represented by the general formula (40) and the compound represented by the general formula (34) may be reacted in the presence of a dehydration condensation agent.

In addition, in the reaction to obtain the compound represented by the general formula (1-4) from the compound represented by the general formula (40), the compound represented by the general formula (1-4) can also be obtained by a reaction of the compound represented by the general formula (40) and the compound represented by the following general formula (35), instead of the method for using the compound represented by the general formula (34).

[II]

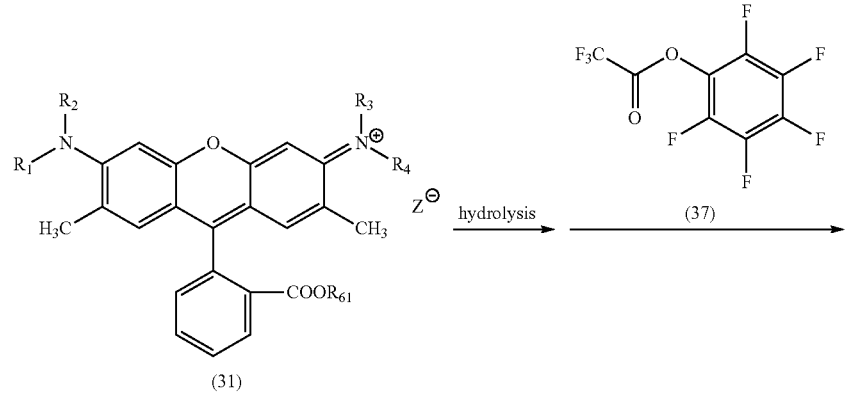

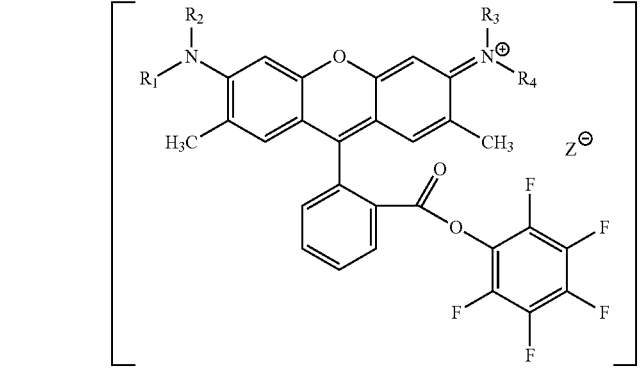

(38)

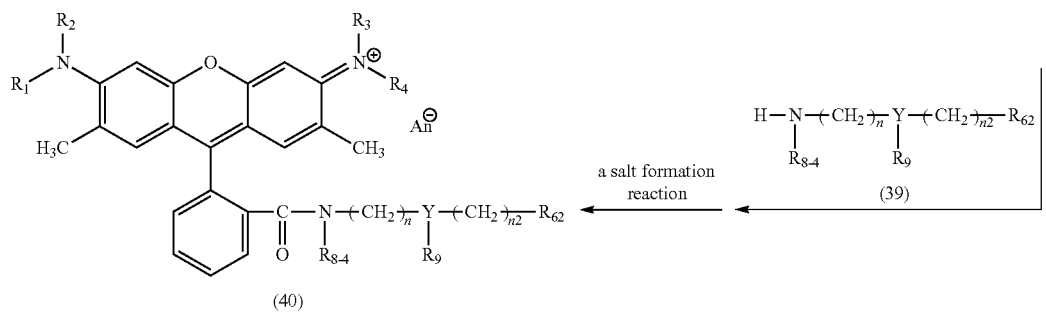

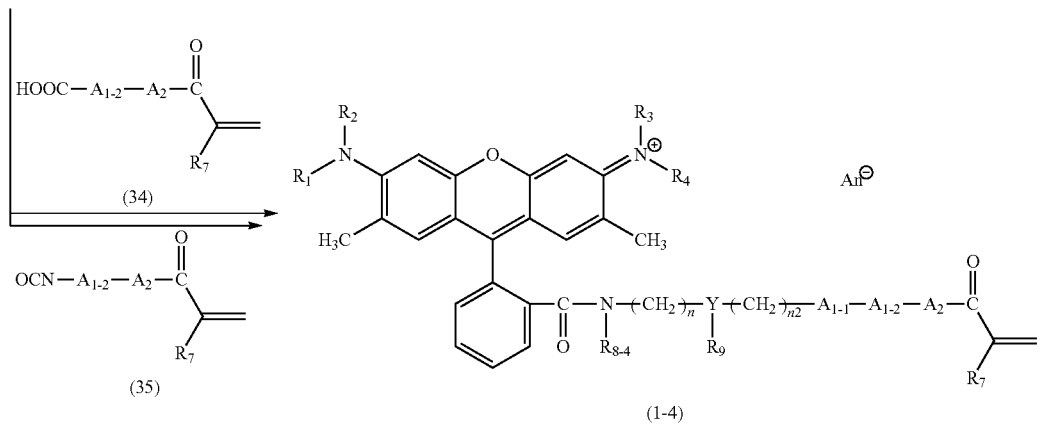

(in the scheme, $R_1$ to $R_4$, $R_7$, $R_9$, $R_{61}$, $R_{62}$, Y, n, $n_2$, $A_{1-1}$, $A_{1-2}$, $A_2$, $Z^-$ and $An^-$ are the same as described above; $R_{8-4}$ represents an alkyl group having 1 to 30 carbon atoms; $n_2$ represents an integer of 0 to 3; $R_{8-4}$ and $R_9$ may form a cyclic structure of a 5 to 6 membered ring together with —N—$(CH_2)_n$—Y— bonding thereto.)

The alkyl group having 1 to 30 carbon atoms in $R_{8-4}$ of the general formulae (1-4), (39) and (40), includes the same one as the alkyl group having 1 to 30 carbon atoms in $R_1$ to $R_4$ of the general formula (1), and the preferable ones are also the same.

In the case where $R_{8-4}$ and $R_9$ in the general formulae (1-4), (39) and (40) form a cyclic structure of a 5 to 6 membered ring together with —N—$(CH_2)_n$—Y— bonding thereto, the cyclic structure is the one represented by the general formula (1-2).

The group where —$(CH_2)_{n2}$—, $A_{1-1}$ and $A_{1-2}$ are combined in the scheme [II] provides $A_1$ in the compound of the present invention. In this case, total number of carbon atoms contained in —$(CH_2)_{n2}$—, $A_{1-1}$ and $A_{1-2}$ is 1 to 21.

Preferable specific examples of the compound represented by the general formula (1-4) include the compound represented by the following general formula (1'-4).

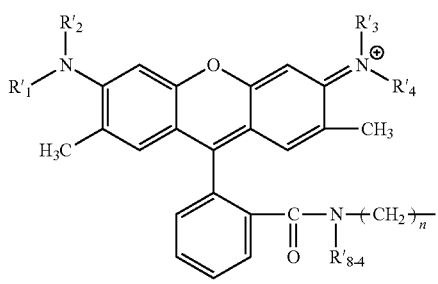
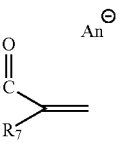

(1'-4)

(wherein R'₁ to R'₄, R₇, R₉, Y, n, n₂, A₁₋₁, A₁₋₂ and An⁻ are the same as described above; R'₈₋₄ represents an alkyl group having 1 to 6 carbon atoms; R'₈₋₄ and R₉ may form a cyclic structure of a 5 to 6 membered ring together with —N—(CH₂)ₙ—Y— bonding thereto.)

The alkyl group having 1 to 6 carbon atoms in R'₈₋₄ of the general formula (1'-4) includes the same one as the alkyl group having 1 to 6 carbon atoms in R₉ of the general formula (1), and the preferable ones are also the same.

In the case where R'₈₋₄ and R₉ in the general formula (1'-4) form a cyclic structure of a 5 to 6 membered ring together with —N—(CH₂)ₙ—Y— bonding thereto, the cyclic structure is the one represented by the general formula (1-2).

Preferable specific examples of the compound represented by the general formula (1'-4) include the compound represented by the following general formula (1''-4).

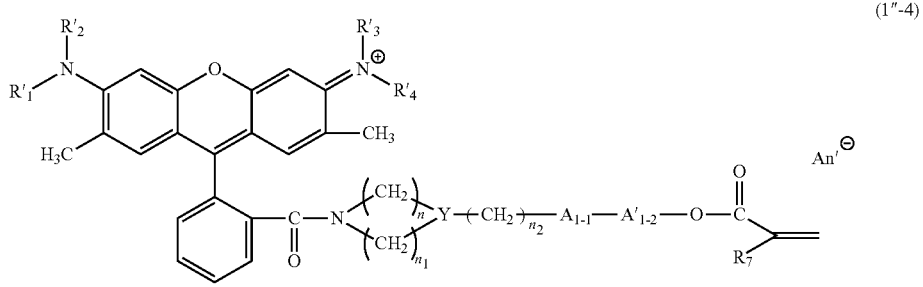

(1''-4)

(wherein R'₁ to R'₄, R₇, Y, n, n₁, n₂, A₁₋₁, A'₁₋₂ and An'⁻ are the same as described above.)

Preferable combinations of R'₁ to R'₄, R₇, Y, n, n₁, n₂, A₁₋₁ and A'₁₋₂ of the general formula (1''-4) include those described in the following table.

| R₁' | R₂' | R₃' | R₄' | R₇ | Y | n | n₁ | n₂ | A₁₋₁ | A'₁₋₂ |
|---|---|---|---|---|---|---|---|---|---|---|
| Hydrogen atom | Methyl group | Methyl group | Hydrogen atom | Hydrogen atom or methyl group | Formula (1-1) or nitrogen atom | 2 | 2 | 2 | —OCO— | Formula (P') |
|  | Methyl group | Methyl group |  |  |  | 2 | 2 | 2 | —NHCONH— | Ethylene group |
|  | Ethyl group | Ethyl group |  |  |  | 0 | 3 | 2 | —OCO— | Formula (P') |
|  | Ethyl group | Ethyl group |  |  |  | 0 | 3 | 2 | —NHCONH— | Ethylene group |
|  | Ethyl group | Ethyl group |  |  |  | 0 | 4 | 2 | —OCO— | Formula (P') |
|  | Ethyl group | Ethyl group |  |  |  | 0 | 4 | 2 | —NHCONH— | Ethylene group |
|  | Ethyl group | Ethyl group |  |  |  | 1 | 2 | 2 | —OCO— | Formula (P') |
|  | Ethyl group | Ethyl group |  |  |  | 1 | 2 | 2 | —NHCONH— | Ethylene group |
|  | Ethyl group | Ethyl group |  |  |  | 1 | 3 | 2 | —OCO— | Formula (P') |
|  | Ethyl group | Ethyl group |  |  |  | 1 | 3 | 2 | —NHCONH— | Ethylene group |
|  | Ethyl group | Ethyl group |  |  |  | 2 | 2 | 0 | —OCO— | Formula (P') |
|  | Ethyl group | Ethyl group |  |  |  | 2 | 2 | 0 | —NHCONH— | Ethylene group |
|  | Ethyl group | Ethyl group |  |  |  | 2 | 2 | 1 | —OCO— | Formula (P') |
|  | Ethyl group | Ethyl group |  |  |  | 2 | 2 | 1 | —NHCONH— | Ethylene group |
|  | Ethyl group | Ethyl group |  |  |  | 2 | 2 | 2 | —OCO— | Formula (P') |
|  | Ethyl group | Ethyl group |  |  |  | 2 | 2 | 2 | —NHCONH— | Ethylene group |
|  | Ethyl group | Ethyl group |  |  |  | 2 | 2 | 3 | —OCO— | Formula (P') |
|  | Ethyl group | Ethyl group |  |  |  | 2 | 2 | 3 | —NHCONH— | Ethylene group |
|  | n-propyl group | n-propyl group |  |  |  | 2 | 2 | 2 | —OCO— | Formula (P') |
|  | n-propyl group | n-propyl group |  |  |  | 2 | 2 | 2 | —NHCONH— | Ethylene group |
|  | Isopropyl group | Isopropyl group |  |  |  | 2 | 2 | 2 | —OCO— | Formula (P') |
|  | Isopropyl group | Isopropyl group |  |  |  | 2 | 2 | 2 | —NHCONH— | Ethylene group |

-continued

| R₁' | R₂' | R₃' | R₄' | R₇ | Y | n | n₁ | n₂ | $A_{1-1}$ | $A'_{1-2}$ |
|---|---|---|---|---|---|---|---|---|---|---|
| Methyl group | Methyl group | Methyl group | Methyl group | | | 2 | 2 | 2 | —OCO— | Formula (P') |
| | Methyl group | Methyl group | | | | 2 | 2 | 2 | —NHCONH— | Ethylene group |
| | Ethyl group | Ethyl group | | | | 2 | 2 | 2 | —OCO— | Formula (P') |
| | Ethyl group | Ethyl group | | | | 2 | 2 | 2 | —NHCONH— | Ethylene group |
| | n-propyl group | n-propyl group | | | | 2 | 2 | 2 | —OCO— | Formula (P') |
| | n-propyl group | n-propyl group | | | | 2 | 2 | 2 | —NHCONH— | Ethylene group |
| | Isopropyl group | Isopropyl group | | | | 2 | 2 | 2 | —OCO— | Formula (P') |
| | Isopropyl group | Isopropyl group | | | | 2 | 2 | 2 | —NHCONH— | Ethylene group |
| Ethyl group | Ethyl group | Ethyl group | Ethyl group | | | 2 | 2 | 2 | —OCO— | Formula (P') |
| | Ethyl group | Ethyl group | | | | 2 | 2 | 2 | —NHCONH— | Ethylene group |
| | n-propyl group | n-propyl group | | | | 2 | 2 | 2 | —OCO— | Formula (P') |
| | n-propyl group | n-propyl group | | | | 2 | 2 | 2 | —NHCONH— | Ethylene group |
| | Isopropyl group | Isopropyl group | | | | 2 | 2 | 2 | —OCO— | Formula (P') |
| | Isopropyl group | Isopropyl group | | | | 2 | 2 | 2 | —NHCONH— | Ethylene group |
| n-propyl group | n-propyl group | n-propyl group | n-propyl group | | | 2 | 2 | 2 | —OCO— | Formula (P') |
| | n-propyl group | n-propyl group | | | | 2 | 2 | 2 | —NHCONH— | Ethylene group |

An⁻ used together with the combinations of the table includes the same one as An⁻ used together with preferable combinations of $R'_1$ to $R'_4$, $R_7$, $R_9$, n and $A'_1$ in the general formula (1").

Preferable specific examples among the intermediates represented by the general formula (38) include the intermediate represented by the following general formula (38').

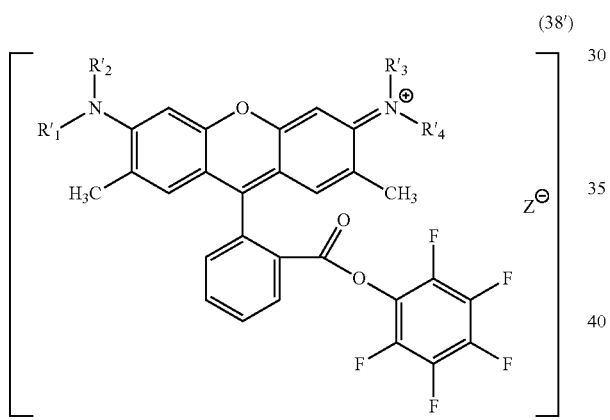

(wherein $R'_1$ to $R'_4$ and $Z^-$ are the same as described above.)

Preferable combinations of $R'_1$ to $R'_4$ and $Z^-$ in the general formula (38') include, for example, those described in the following table.

Preferable specific examples of the compound represented by the general formula (39) include the following ones.

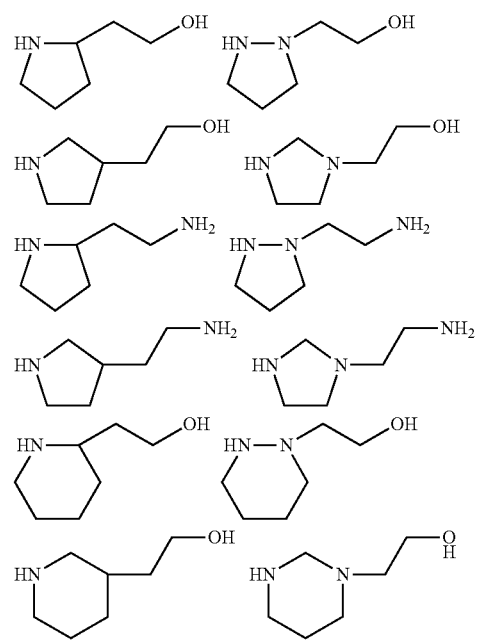

| R₁' | R₂' | R₃' | R₄' | Z⁻ |
|---|---|---|---|---|
| Hydrogen atom | Methyl group | Methyl group | Hydrogen atom | Cl⁻ |
| Hydrogen atom | Ethyl group | Ethyl group | Hydrogen atom | Cl⁻ |
| Hydrogen atom | Ethyl group | Ethyl group | Hydrogen atom | $NO_3^-$ |
| Hydrogen atom | Ethyl group | Ethyl group | Hydrogen atom | $SO_4^{2-}$ |
| Hydrogen atom | Ethyl group | Ethyl group | Hydrogen atom | $HSO_4^-$ |
| Hydrogen atom | Ethyl group | Ethyl group | Hydrogen atom | $ClO_4^-$ |
| Hydrogen atom | n-propyl group | n-propyl group | Hydrogen atom | Cl⁻ |
| Hydrogen atom | Isopropyl group | Isopropyl group | Hydrogen atom | Cl⁻ |
| Methyl group | Methyl group | Methyl group | Methyl group | Cl⁻ |
| Methyl group | Ethyl group | Ethyl group | Methyl group | Cl⁻ |
| Methyl group | n-propyl group | n-propyl group | Methyl group | Cl⁻ |
| Methyl group | Isopropyl group | Isopropyl group | Methyl group | Cl⁻ |
| Ethyl group | Ethyl group | Ethyl group | Ethyl group | Cl⁻ |
| Ethyl group | n-propyl group | n-propyl group | Ethyl group | Cl⁻ |
| Ethyl group | Isopropyl group | Isopropyl group | Ethyl group | Cl⁻ |
| n-propyl group | n-propyl group | n-propyl group | n-propyl group | Cl⁻ |

Among the above-described specific examples, the following ones are preferable.

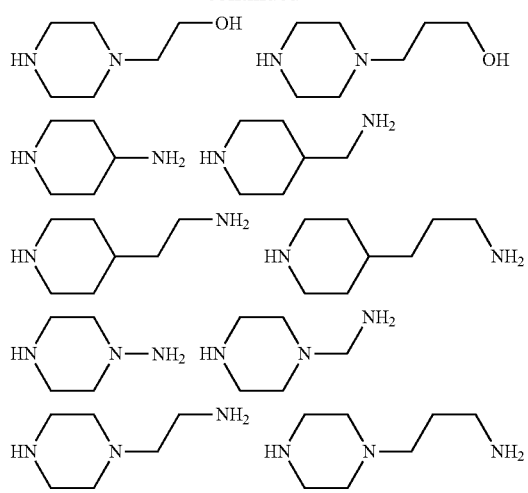

Among the above-described specific examples, the following ones are more preferable.

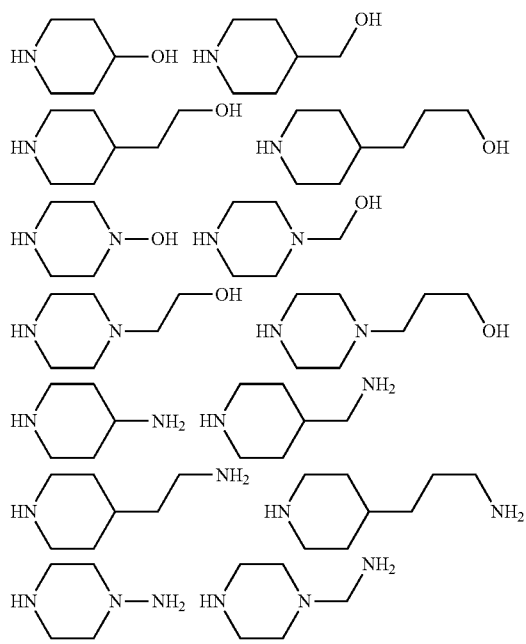

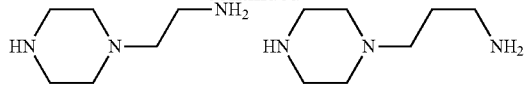

Preferable specific examples among the compound represented by the general formula (40) include the compound represented by the following general formula (40').

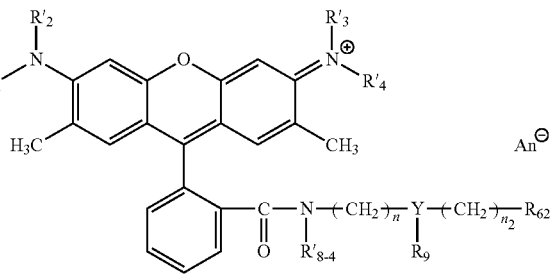

(40')

(wherein $R'_1$ to $R'_4$, $R'_{8-4}$, $R_9$, $R_{62}$, Y, n, $n_2$ and $An^-$ are the same as described above; $R'_{8-4}$ and $R_9$ may form a cyclic structure of a 5 to 6 membered ring together with —N—$(CH_2)_n$—Y bonding thereto.)

Preferable specific examples of the compound represented by the general formula (40') include the compound represented by the following general formula (40").

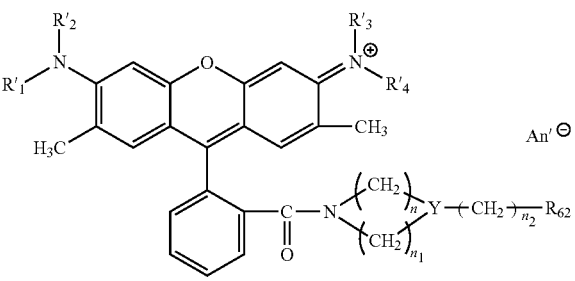

(40")

(wherein $R'_1$ to $R'_4$, $R_{62}$, Y, n, $n_1$, $n_2$ and $An'^-$ are the same as described above.)

Preferable combinations of $R'_1$ to $R'_4$, $R_{62}$, Y, n, $n_1$, and $n_2$ in the general formula (40") include, for example, those described in the following table.

| $R_1'$ | $R_2'$ | $R_3'$ | $R_4'$ | $R_{62}$ | Y | n | $n_1$ | $n_3$ |
|---|---|---|---|---|---|---|---|---|
| Hydrogen atom | Methyl group | Methyl group | Hydrogen atom | —OH or —NH$_2$ | Formula (1-1) or nitrogen atom | 2 | 2 | 2 |
| Hydrogen atom | Ethyl group | Ethyl group | Hydrogen atom | —OH or —NH$_2$ | Formula (1-1) or nitrogen atom | 0 | 3 | 2 |
| Hydrogen atom | Ethyl group | Ethyl group | Hydrogen atom | —OH or —NH$_2$ | Formula (1-1) or nitrogen atom | 0 | 4 | 2 |
| Hydrogen atom | Ethyl group | Ethyl group | Hydrogen atom | —OH or —NH$_2$ | Formula (1-1) or nitrogen atom | 1 | 2 | 2 |
| Hydrogen atom | Ethyl group | Ethyl group | Hydrogen atom | —OH or —NH$_2$ | Formula (1-1) or nitrogen atom | 1 | 3 | 2 |
| Hydrogen atom | Ethyl group | Ethyl group | Hydrogen atom | —OH or —NH$_2$ | Formula (1-1) or nitrogen atom | 2 | 2 | 0 |
| Hydrogen atom | Ethyl group | Ethyl group | Hydrogen atom | —OH or —NH$_2$ | Formula (1-1) or nitrogen atom | 2 | 2 | 1 |
| Hydrogen atom | Ethyl group | Ethyl group | Hydrogen atom | —OH or —NH$_2$ | Formula (1-1) or nitrogen atom | 2 | 2 | 2 |
| Hydrogen atom | Ethyl group | Ethyl group | Hydrogen atom | —OH or —NH$_2$ | Formula (1-1) or nitrogen atom | 2 | 2 | 3 |
| Hydrogen atom | n-propyl group | n-propyl group | Hydrogen atom | —OH or —NH$_2$ | Formula (1-1) or nitrogen atom | 2 | 2 | 2 |
| Hydrogen atom | Isopropyl group | Isopropyl group | Hydrogen atom | —OH or —NH$_2$ | Formula (1-1) or nitrogen atom | 2 | 2 | 2 |
| Methyl group | Methyl group | Methyl group | Methyl group | —OH or —NH$_2$ | Formula (1-1) or nitrogen atom | 2 | 2 | 2 |
| Methyl group | Ethyl group | Ethyl group | Methyl group | —OH or —NH$_2$ | Formula (1-1) or nitrogen atom | 2 | 2 | 2 |
| Methyl group | n-propyl group | n-propyl group | Methyl group | —OH or —NH$_2$ | Formula (1-1) or nitrogen atom | 2 | 2 | 2 |
| Methyl group | Isopropyl group | Isopropyl group | Methyl group | —OH or —NH$_2$ | Formula (1-1) or nitrogen atom | 2 | 2 | 2 |

-continued

| $R_1'$ | $R_2'$ | $R_3'$ | $R_4'$ | $R_{62}$ | Y | n | $n_1$ | $n_3$ |
|---|---|---|---|---|---|---|---|---|
| Ethyl group | Ethyl group | Ethyl group | Ethyl group | —OH or —NH$_2$ | Formula (1-1) or nitrogen atom | 2 | 2 | 2 |
| Ethyl group | n-propyl group | n-propyl group | Ethyl group | —OH or —NH$_2$ | Formula (1-1) or nitrogen atom | 2 | 2 | 2 |
| Ethyl group | Isopropyl group | Isopropyl group | Ethyl group | —OH or —NH$_2$ | Formula (1-1) or nitrogen atom | 2 | 2 | 2 |
| n-propyl group | n-propyl group | n-propyl group | n-propyl group | —OH or —NH$_2$ | Formula (1-1) or nitrogen atom | 2 | 2 | 2 |

The hydrolysis reaction of the scheme [II] is carried out by the addition of a base to the compound represented by the general formula (31), and then by treatment with an acid.

The hydrolysis reaction may be carried out, usually at 10 to 100° C., preferably at 60 to 100° C., for usually 1 to 24 hours, and preferably 6 to 12 hours.

The base in the hydrolysis reaction includes, for example, sodium hydroxide, potassium hydroxide, and the like. Use amount of the base is usually 1 to 10 equivalent, relative to mole number of the compound represented by the general formula (31).

A method for treatment with the acid in the hydrolysis reaction is carried out by the addition of an acid such as hydrochloric acid, sulfuric acid, nitric acid, perchloric acid, and the like, into the reaction system in which the base is added to the compound represented by the general formula (31). The acid added into the reaction system may be used alone, or in combination of two or more kinds thereof as appropriate. Amount of the acid added into the reaction system may be any amount as long as pH of the reaction system is 4 or less, and it is usually 1 to 50 times volume, preferably 1 to 20 times volume, relative to volume of the compound represented by the general formula (31).

In the reaction between the acid derived from the compound represented by the general formula (31), obtained by the hydrolysis reaction of the scheme [II], and the compound represented by the formula (37), the acid derived from the compound represented by the general formula (31) and the compound represented by the formula (37) may be reacted in a solvent, usually at 0 to 100° C., preferably at 10 to 50° C., for usually 1 to 48 hours, and preferably 2 to 10 hours.

The solvent in the reaction between the acid derived from the compound represented by the general formula (31) and the compound represented by the formula (37) includes, for example, tetrahydrofuran (THF), dioxane, N,N-dimethylformamide (DMF), methylene chloride, and the like. They may be used alone, or in combination of two or more kinds thereof as appropriate. Use amount of the reaction solvent is usually 1 to 50 times volume, and preferably 1 to 20 times volume, relative to total volume of the acid derived from the compound represented by the general formula (31) and the compound represented by the formula (37).

Use amount of the compound represented by the general formula (37) is usually 1 to 2 equivalent, and preferably 1 to 1.5 equivalent, relative to mole number of the acid derived from the compound represented by the general formula (31).

In the reaction between the intermediate represented by the general formula (38) and the compound represented by the general formula (39), the intermediate represented by the general formula (38) and the compound represented by the general formula (39) may be reacted in a solvent, usually at 0 to 80° C., preferably at 10 to 50° C., for usually 1 to 48 hours, and preferably 5 to 10 hours.

The solvent in the reaction between the intermediate represented by the general formula (38) and the compound represented by the general formula (39) includes, for example, tetrahydrofuran (THF), dioxane, N,N-dimethylformamide (DMF), methylene chloride, and the like. They may be used alone, or in combination of two or more kinds thereof as appropriate. Use amount of the reaction solvent is usually 1 to 50 times volume, and preferably 1 to 20 times volume, relative to total volume of the intermediate represented by the general formula (38) and the compound represented by the general formula (39).

Use amount of the compound represented by the general formula (39) is usually 1 to 2 equivalent, and preferably 1 to 1.5 equivalent, relative to mole number of the intermediate represented by the general formula (38).

The salt formation reaction in the scheme [II] may be carried out similarly as in the salt formation reaction in the scheme [I], and reaction temperature, reaction time, the salt of the anion of the present invention and a solvent are the same as described above.

The reaction between the compound represented by the general formula (40) and the compound represented by the general formula (34) may be carried out similarly as in the reaction between the compound represented by the general formula (33) and the compound represented by the general formula (34), and reaction temperature, reaction time, a solvent, a dehydration condensation agent and a catalyst are the same as described above.

The reaction between the compound represented by the general formula (40) and the compound represented by the general formula (35) may be carried out similarly as in the reaction between the compound represented by the general formula (33) and the compound represented by the general formula (35), and reaction temperature, reaction time and a solvent are the same as described above.

Pressure in a series of the above-described reactions is not especially limited, as long as the series of the reactions is carried out without delay, and the reactions may be carried out, for example, under ambient pressure.

Resulting reactants and products after the series of the reactions can be isolated by a general post-treatment operation and purification operation usually carried out in this field. Specifically, for example, the resulting reactants and products may be isolated, as needed, by filtration, washing, extraction, concentration under reduced pressure, recrystallization, distillation, column chromatography, and the like.

In addition, among the compound of the present invention, for example, the one where (i) $A_2$ in the general formula (1) is —O—, as well as (ii) $R_8$ in the general formula (1) is an alkyl group having 1 to 30 carbon atoms, or $R_8$ and $R_9$ form a cyclic structure of a 5 to 6 membered ring together with —N—$(CH_2)_n$—Y— bonding thereto (a compound represented by the following general formula (1-7)) can be produced also by a method shown in the next scheme [III]. That is, after a reaction between a compound represented by the following general formula (41) and a compound represented by the following general formula (42), a resulting compound represented by the general formula (43) and methacrylic anhydride or acrylic anhydride are reacted in the presence of a dehydration condensation agent, and then a salt formation reaction may be carried out.

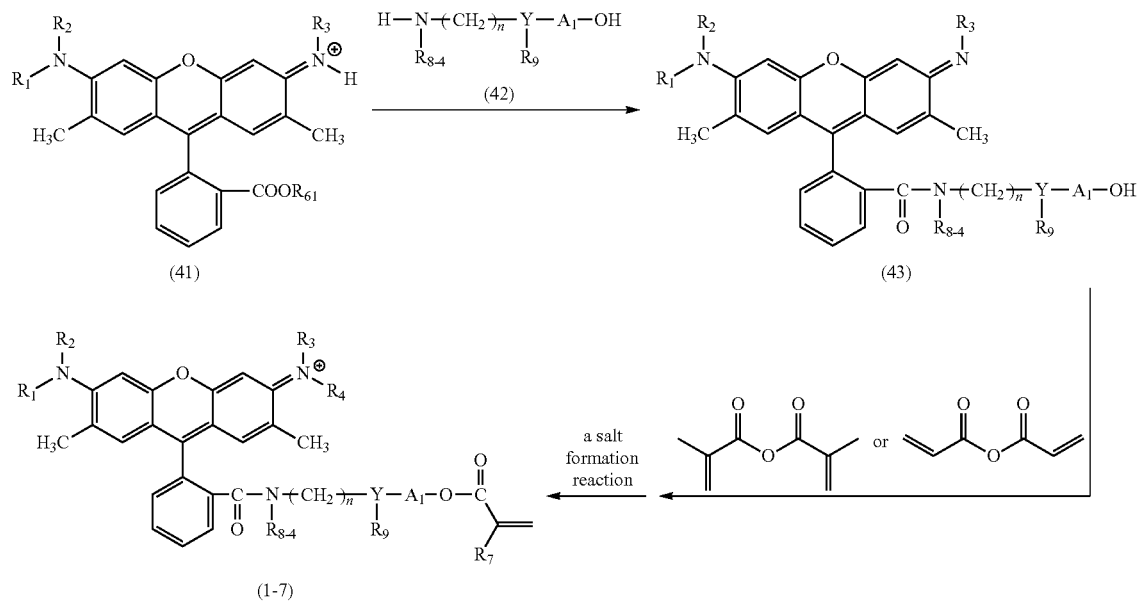

(in the scheme, $R_1$ to $R_4$, $R_7$, $R_{8-4}$, $R_9$, $R_{61}$, Y, n, $A_1$, $A_2$, Z' and An" are the same as described above.)

Preferable specific examples of the compound represented by the general formula (1-7) include the compound represented by the following general formula (1'-7).

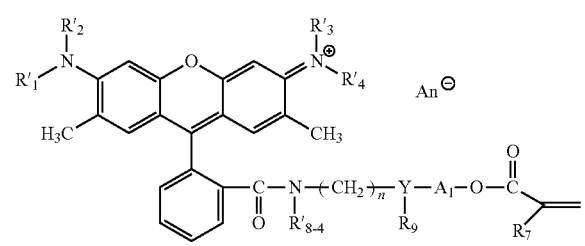

(wherein $R'_1$ to $R'_4$, $R_7$, $R'_{8-4}$, $R_9$, Y, n, $A_1$ and An⁻ are the same as described above.)

Preferable specific examples among the compound represented by the general formula (1'-7) include the compound represented by the following general formula (1"-7).

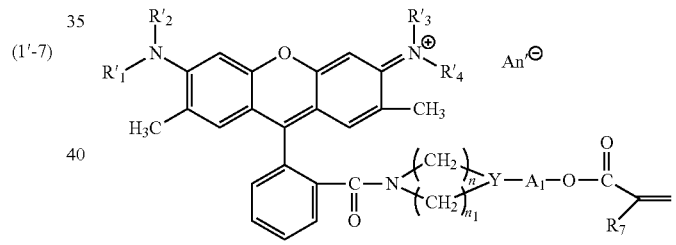

(wherein $R'_1$ to $R'_4$, $R_7$, Y, n, $n_1$, $A_1$ and An'⁻ are the same as described above.)

Preferable combinations of $R'_1$ to $R'_4$, $R_7$, Y, n, $n_1$ and $A_1$ in the general formula (1"-7) include, for example, those described in the following table.

| $R_1'$ | $R_2'$ | $R_3'$ | $R_4'$ | $R_7$ | Y | n | $n_1$ | $A_1$ |
|---|---|---|---|---|---|---|---|---|
| Hydrogen atom | Methyl group | Methyl group | Hydrogen atom | Hydrogen atom or methyl group | Formula (1-1) or nitrogen atom | 2 | 2 | Methyl group, ethyl group, or n-propyl group |
|  | Ethyl group | Ethyl group |  |  |  | 0 | 3 |  |
|  | Ethyl group | Ethyl group |  |  |  | 0 | 4 |  |
|  | Ethyl group | Ethyl group |  |  |  | 1 | 2 |  |
|  | Ethyl group | Ethyl group |  |  |  | 1 | 3 |  |
|  | Ethyl group | Ethyl group |  |  |  | 2 | 2 |  |
|  | n-propyl group | n-propyl group |  |  |  | 2 | 2 |  |
|  | Isopropyl group | Isopropyl group |  |  |  | 2 | 2 |  |
| Methyl group | Methyl group | Methyl group | Methyl group |  |  | 2 | 2 |  |
|  | Ethyl group | Ethyl group |  |  |  |  |  |  |
|  | n-propyl group | n-propyl group |  |  |  |  |  |  |
|  | Isopropyl group | Isopropyl group |  |  |  |  |  |  |
| Ethyl group | Ethyl group | Ethyl group | Ethyl group |  |  | 2 | 2 |  |
|  | n-propyl group | n-propyl group |  |  |  |  |  |  |
|  | Isopropyl group | Isopropyl group |  |  |  |  |  |  |
| n-propyl group | n-propyl group | n-propyl group | n-propyl group |  |  | 2 | 2 |  |

An⁻ used together with the combinations in the table includes the same one as An⁻ used together with preferable combinations of $R'_1$ to $R'_4$, $R_7$, $R^9$, n and $A'_1$ in the general formula (1″).

Preferable combinations of $R_1$ to $R_3$, $R_{61}$ and $Z^-$ in the general formula (41) include, for example, those described in the following table.

| $R_1'$ | $R_2'$ | $R_3'$ | $Z^-$ |
|---|---|---|---|
| Hydrogen atom | Methyl group | Methyl group | Cl⁻ |
|  | Ethyl group | Ethyl group | Cl⁻ |
|  | Ethyl group | Ethyl group | $NO_3^-$ |
|  | Ethyl group | Ethyl group | $SO_4^{2-}$ |
|  | Ethyl group | Ethyl group | $HSO_4^-$ |
|  | Ethyl group | Ethyl group | $ClO_4^-$ |
|  | n-propyl group | n-propyl group | Cl⁻ |
|  | Isopropyl group | Isopropyl group | Cl⁻ |
| Methyl group | Methyl group | Methyl group | Cl⁻ |
|  | Ethyl group | Ethyl group | Cl⁻ |
|  | n-propyl group | n-propyl group | Cl⁻ |
|  | Isopropyl group | Isopropyl group | Cl⁻ |
| Ethyl group | Ethyl group | Ethyl group | Cl⁻ |
|  | n-propyl group | n-propyl group | Cl⁻ |
|  | Isopropyl group | Isopropyl group | Cl⁻ |
| n-propyl group | n-propyl group | n-propyl group | Cl⁻ |

Specific examples of the compound represented by the general formula (42) include the following ones.

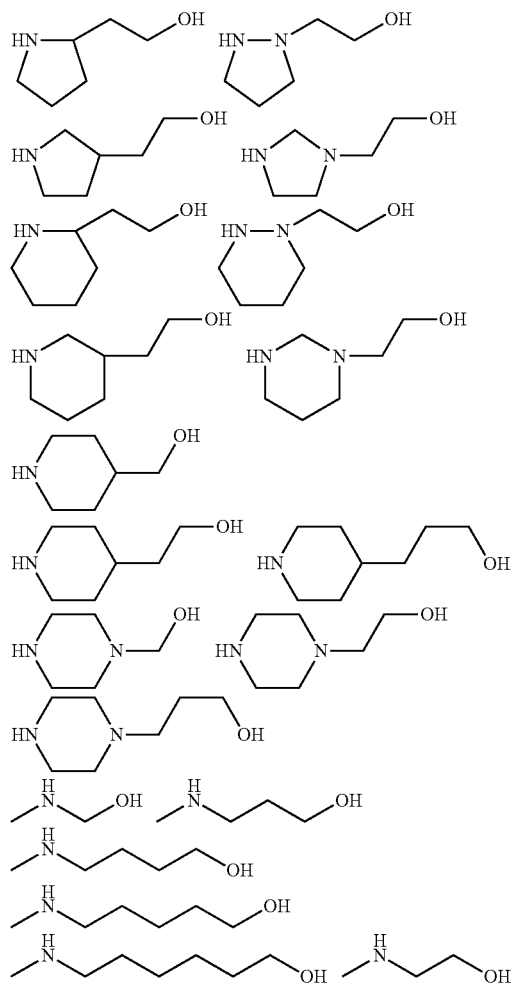
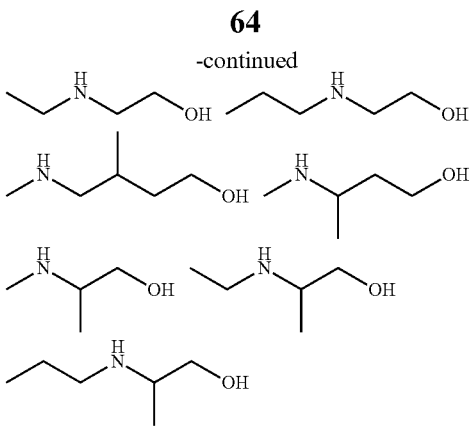

Among the above-described specific examples, the following ones are preferable.

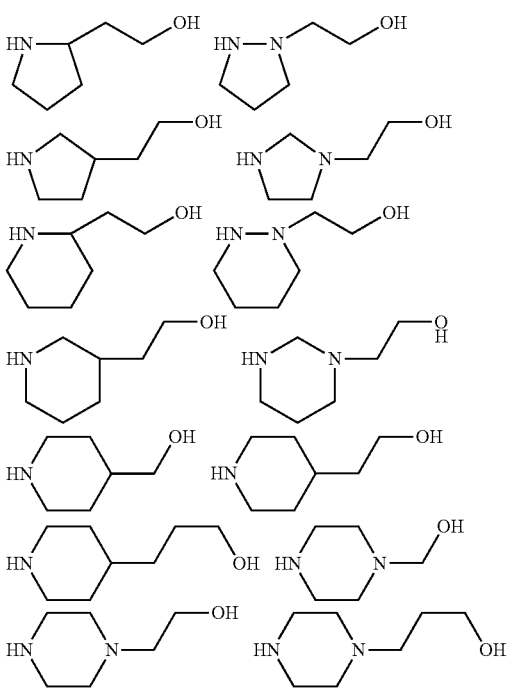

Among the above-described specific examples, the following ones are more preferable.

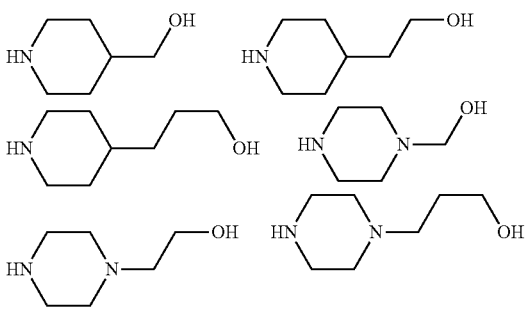

Preferable specific examples among the compound represented by the general formula (43) include the compound represented by the following general formula (43').

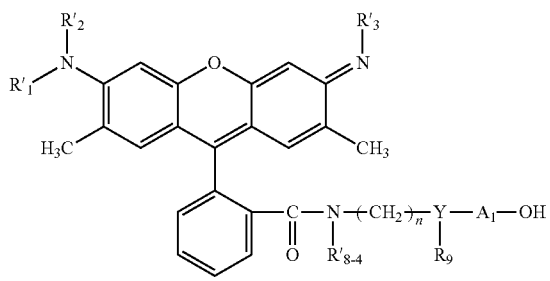

(43')

(wherein R'$_1$ to R'$_4$, R'$_{8-4}$, R$_9$, Y, n and A$_1$ are the same as describe above.)

Preferable specific examples among the compound represented by the general formula (43') include the compound represented by the following general formula (43").

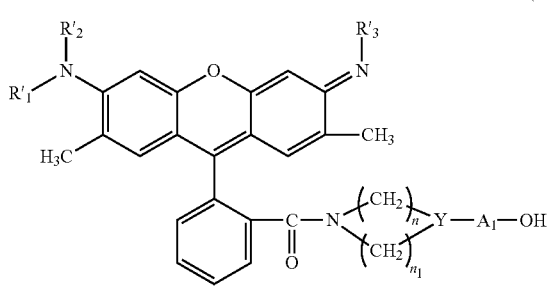

(43")

(wherein R'$_1$ to R'$_4$, Y, n, n$_1$ and A$_1$ are the same as describe above.)

Preferable combinations of R'$_1$ to R'$_4$, Y, n, n$_1$ and A$_1$ in the general formula (43") include those described in the following table.

Use amount of the compound represented by the general formula (42) is usually 1 to 10 equivalent, and preferably 1 to 6 equivalent, relative to mole number of the compound represented by the general formula (41).

In the reaction between the intermediate represented by the general formula (43) and methacrylic anhydride or acrylic anhydride, the intermediate represented by the general formula (43) and methacrylic anhydride or acrylic anhydride may be reacted in a solvent, in the presence of a polymerization inhibitor as needed, usually at 0 to 80° C., preferably at 10 to 50° C., for usually 1 to 72 hours, and preferably 24 to 48 hours.

The solvent in the reaction between the intermediate represented by the general formula (43) and methacrylic anhydride or acrylic anhydride includes, for example, tetrahydrofuran (THF), dioxane, N,N-dimethylformamide (DMF), methylene chloride, chloroform, methacrylic acid, acrylic acid, and the like. They may be used alone, or in combination of two or more kinds thereof as appropriate.

Use amount of the reaction solvent is usually 1 to 50 times volume, and preferably 1 to 20 times volume, relative to total volume of the intermediate represented by the general formula (43) and methacrylic anhydride or acrylic anhydride.

Use amount of methacrylic anhydride or acrylic anhydride is usually 1 to 10 equivalent, and preferably 1 to 8 equivalent, relative to mole number of the intermediate represented by the general formula (43).

The polymerization inhibitor in the reaction between the intermediate represented by the general formula (43) and methacrylic anhydride or acrylic anhydride includes, for example, p-methoxyphenol, and the like.

The salt formation reaction in the scheme [II] may be carried out similarly as in the salt formation reaction in the scheme [I], and reaction temperature, reaction time, the salt of the anion of the present invention and a solvent are the same as described above.

Pressure in a series of the above-described reactions is not especially limited, as long as the series of the reactions is carried out without delay, and the reactions may be carried out, for example, under ambient pressure.

| R$_1$' | R$_2$' | R$_3$' | R$_4$' | Y | n | n$_1$ | A$_1$ |
|---|---|---|---|---|---|---|---|
| Hydrogen atom | Methyl group | Methyl group | Hydrogen atom | Formula (1-1) or nitrogen atom | 2 | 2 | Methyl group, ethyl group, or n-propyl group |
|  | Ethyl group | Ethyl group |  |  | 0 | 3 |  |
|  | Ethyl group | Ethyl group |  |  | 0 | 4 |  |
|  | Ethyl group | Ethyl group |  |  | 1 | 2 |  |
|  | Ethyl group | Ethyl group |  |  | 1 | 3 |  |
|  | Ethyl group | Ethyl group |  |  | 2 | 2 |  |
|  | n-propyl group | n-propyl group |  |  | 2 | 2 |  |
|  | Isopropyl group | Isopropyl group |  |  | 2 | 2 |  |
| Methyl group | Methyl group | Methyl group | Methyl group |  | 2 | 2 |  |
|  | Ethyl group | Ethyl group |  |  |  |  |  |
|  | n-propyl group | n-propyl group |  |  |  |  |  |
|  | Isopropyl group | Isopropyl group |  |  |  |  |  |
| Ethyl group | Ethyl group | Ethyl group | Ethyl group |  | 2 | 2 |  |
|  | n-propyl group | n-propyl group |  |  |  |  |  |
|  | Isopropyl group | Isopropyl group |  |  |  |  |  |
| n-propyl group | n-propyl group | n-propyl group | n-propyl group |  | 2 | 2 |  |

In the reaction between the compound represented by the general formula (41) and the compound represented by the general formula (42), the compound represented by the general formula (41) and the compound represented by the general formula (42) may be reacted, usually at 10 to 100° C., preferably at 60 to 100° C., for usually 1 to 72 hours, and preferably 24 to 48 hours.

Resulting reactants and products after the series of the reactions can be isolated by a general post-treatment operation and purification operation usually carried out in this field. Specifically, for example, the resulting reactants and products may be isolated, as needed, by filtration, washing, extraction, concentration under reduced pressure, recrystallization, distillation, column chromatography, and the like.

[Polymer of the Resent Invention]

The polymer of the present invention is a polymer having a monomer unit derived from the compound of the present invention.

Weight average molecular weight (Mw) of the polymer of the present invention is usually 2,000 to 100,000, and preferably 2,000 to 50,000, and more preferably 2,000 to 30,000. In addition, distribution degree thereof (Mw/Mn) is usually 1.00 to 5.00, and preferably 1.00 to 3.00.

The polymer of the present invention may be a homopolymer or a copolymer, as long as it is the one having the monomer unit derived from the compound represented by the general formula (1), and the copolymer having high heat resistance effect is preferable.

The copolymer includes, for example, the one comprising one to two kinds of the monomer unit derived from the compound represented by the following general formula (2), the general formula (3), the general formula (4) or the general formula (5), and the monomer unit derived from the compound represented by the general formula (1), as the constituents thereof.

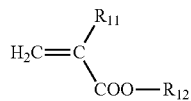
(2)

[wherein, $R_{11}$ represents a hydrogen atom or a methyl group; $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms which has oxygen atom or no oxygen atom, a dialkylaminoalkyl group having 3 to 9 carbon atoms, a fluoroalkyl group having 1 to 18 carbon atoms, an N-alkylenephthalimide group having 9 to 14 carbon atoms, a group represented by the following general formula (2-1):

$$(-R_{21}-O)_q-R_{22} \quad (2\text{-}1)$$

(wherein $R_{21}$ represents an alkylene group having 1 to 3 carbon atoms which has a hydroxy group as a substituent or no substituent; $R_{22}$ represents a phenyl group having a hydroxy group as a substituent or not having a substituent, or an alkyl group having 1 to 3 carbon atoms; and q represents an integer of 1 to 3.), a group represented by the following general formula (2-2):

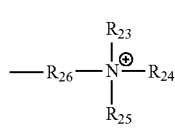
(2-2)

(wherein $R_{23}$ to $R_{25}$ represent an alkyl group having 1 to 3 carbon atoms; $R_{26}$ represents an alkylene group having 1 to 3 carbon atoms.), or a group represented by the following general formula (2-3):

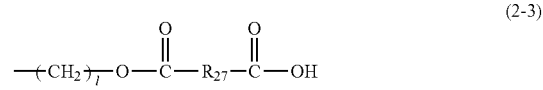
(2-3)

(wherein l represents an integer of 1 to 6; $R_{27}$ represents a phenylene group or a cyclohexylene group.)]

(3)

(wherein $R_{11}$ is the same as described above; $R_{13}$ represents a hydrogen atom or an alkyl group having 1 to 3 carbon atoms; $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms; $R_{13}$ and $R_{14}$ may form a morpholino group together with a nitrogen atom adjacent thereto.)

(4)

(wherein $R_{15}$ represents a phenyl group or a pyrrolidino group; and $R_{11}$ is the same as described above.)

(5)

(wherein $R_{17}$ represents a nitrogen atom or an oxygen atom; j represents 0 when $R_{17}$ is an oxygen atom, and 1 when $R_{17}$ is a nitrogen atom; $R_{16}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 6 to 10 carbon atoms, a halogenated cycloalkyl group having 6 to 7 carbon atoms, an aryl group having 6 to 10 carbon atoms, an aryl group having 6 to 10 carbon atoms, which has an alkyl group having 1 to 6 carbon atoms as a substituent, or a halogenated aryl group having 6 to 10 carbon atoms.)

As $R_{11}$ in the general formula (2), a methyl group is preferable.

The alkyl group having 1 to 18 carbon atoms in $R_{12}$ of the general formula (2) may be any of the linear, branched or cyclic one, specifically including, for example, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a 3-methylpentyl group, a 2-methylpentyl group, a 1,2-dimethylbutyl group, an n-heptyl group, an isoheptyl group, a sec-heptyl group, an n-octyl group, an isooctyl group, a sec-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a cyclopropyl group, a cyclopentyl group, a cyclohexyl group, a cycloheptyl group, a cyclooctyl group, a cyclodecyl group, a cycloundecyl group, a cyclododecyl group, a cyclotetradecyl group, a cyclooctadecyl group, and the like, and a methyl group and an ethyl group are preferable.

The hydroxyalkyl group having 1 to 10 carbon atoms in $R_{12}$ of the general formula (2) includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, and the like.

The aryl group having 6 to 10 carbon atoms in $R_{12}$ of the general formula (2) includes a phenyl group, a naphthyl group, and the like.

The arylalkyl group having 7 to 13 carbon atoms in $R_{12}$ of the general formula (2) includes, for example, a benzyl group, a phenylethyl group, a phenylpropyl group, a naphthylmethyl group, a naphthylethyl group, a naphthylpropyl group, and the like, and a benzyl group is preferable.

The alkoxyalkyl group having 2 to 9 carbon atoms in $R_{12}$ of the general formula (2) includes, for example, a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, a propoxymethyl group, a propoxyethyl group, a propoxypropyl group, a propoxybutyl group, a propoxypentyl group, a propoxyhexyl group, and the like.

The alkoxyalkoxyalkyl group having 3 to 9 carbon atoms in $R_{12}$ of the general formula (2) includes, for example, a methoxymethoxymethyl group, a methoxymethoxyethyl group, a methoxymethoxypropyl group, an ethoxymethoxymethyl group, an ethoxymethoxyethyl group, an ethoxymethoxypropyl group, a propoxymethoxymethyl group, a propoxymethoxyethyl group, a propoxymethoxypropyl group, an ethoxyethoxymethyl group, an ethoxyethoxyethyl group, an ethoxyethoxypropyl group, a propoxyethoxymethyl group, a propoxyethoxyethyl group, a propoxyethoxypropyl group, a propoxypropoxymethyl group, a propoxypropoxyethyl group, a propoxypropoxypropyl group, and the like.

The aryloxyalkyl group having 7 to 13 carbon atoms in $R_{12}$ of the general formula (2) includes, for example, a phenoxymethyl group, a phenoxyethyl group, a phenoxypropyl group, a naphthyloxymethyl group, a naphthyloxyethyl group, a naphthyloxypropyl group, and the like.

The morpholinoalkyl group having 5 to 7 carbon atoms in $R_{12}$ of the general formula (2) includes, for example, a morpholinomethyl group, a morpholinoethyl group, a morpholinopropyl group, and the like.

The trialkylsilyl group having 3 to 9 carbon atoms in $R_{12}$ of the general formula (2) includes, for example, a trimethylsilyl group, a triethylsilyl group, a tripropylsilyl group, a dimethylethylsilyl group, a diethylmethylsilyl group, and the like.

The alicyclic hydrocarbon group having 6 to 12 carbon atoms which has oxygen atom, in $R_{12}$ of the general formula (2), includes, for example, a dicyclopentenyloxyethyl group, and the like.

The alicyclic hydrocarbon group having 6 to 12 carbon atoms which has no oxygen atom, in $R_{12}$ of general formula (2), includes, for example, a cyclohexyl group, an isobornyl group, a dicyclopentanyl group, and the like.

The dialkylaminoalkyl group having 3 to 9 carbon atoms in $R_{12}$ of the general formula (2) includes, for example, a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The fluoroalkyl group having 1 to 18 carbon atoms in $R_{12}$ of the general formula (2) includes, for example, a 2,2,2-trifluoroethyl group, a 2,2,3,3-tetrafluoropropyl group, a 2,2,3,3-tetrafluoropropyl group, a 2,2,3,3,4,4-hexafluoropropyl group, a 2,2,3,3,4,4,5,5-octafluoropentyl group, a 3,3,4,4,5,5,6,6,7,7,8,8,9,9,10,10,10-heptadecafluorodecyl group, a 2-(heptadecafluorooctyl)ethyl group, and the like.

The N-alkylenephthalimide group having 9 to 14 carbon atoms in $R_{12}$ of the general formula (2) includes, for example, a 2-phthalimideethyl group, a 2-tetrahydrophthalimideethyl group, and the like.

The alkylene group having 1 to 3 carbon atoms which has a hydroxy group as substituent or no substituent, in $R_{21}$ of the general formula (2-1), includes a methylene group, an ethylene group, a propylene group, a hydroxymethylene group, a hydroxyethylene group, a 1-hydroxypropylene group, a 2-hydroxypropylene group, and the like, and an ethylene group, a propylene group and a 2-hydroxypropylene group are preferable.

The phenyl group having a hydroxy group as a substituent or not having a substituent, in $R_{22}$ of the general formula (2-1), includes a hydroxyphenyl group, a phenyl group, and the like.

The alkyl group having 1 to 3 carbon atoms in $R_{22}$ of the general formula (2-1) includes, a methyl group, an ethyl group, a propyl group, and the like.

Specific examples of the group represented by the general formula (2-1) include, a (4-hydroxyphenoxy)methyl group, a (4-hydroxyphenoxy)ethyl group, a (4-hydroxyphenoxy) propyl group, a 1-hydroxy-1-phenoxymethyl group, a 1-hydroxy-2-phenoxyethyl group, a 2-hydroxy-3-phenoxypropyl group, a methyltrimethylene glycol group, a methyltriethylene glycol group, a methyltripropylene glycol group, and the like. Among them, a (4-hydroxyphenoxy)propyl group, a 2-hydroxy-3-phenoxypropyl group, a methyltripropylene glycol group, a methyltriethylene glycol group, and the like, are preferable.

The alkyl group having 1 to 3 carbon atoms in $R_{23}$ to $R_{25}$ of the general formula (2-2) includes a methyl group, an ethyl group, a propyl group, and the like, and a methyl group is preferable.

The alkylene group having 1 to 3 carbon atoms in $R_{26}$ of the general formula (2-2) includes a methylene group, an ethylene group, a propylene group, and the like.

Specific examples of the group represented by the general formula (2-2) include a trimethylammoniummethyl group, a trimethylammoniumethyl group, a triethylammoniumethyl group, a triethylammoniummethyl group, and the like.

Preferable specific examples of the group represented by the general formula (2-3) include, for example, the following ones.

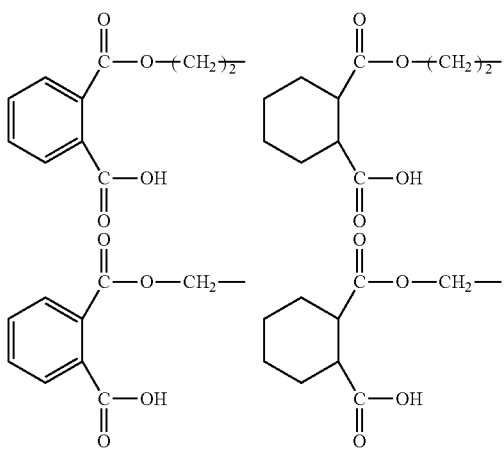

As $R_{12}$ in the general formula (2), a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an aryloxyalkyl group having 7 to 13 carbon atoms, a group represented by the general formula (2-1) and a group represented by the general formula (2-3) are preferable. Among them, a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, and an alkoxyalkyl group having 2 to 9 carbon atoms are more preferable, and a hydrogen atom and an arylalkyl group having 7 to 13 carbon atoms are particularly preferable.

Preferable specific examples of the general formula (2) include acrylic acid, benzyl acrylate, methacrylic acid, benzyl methacrylate, hydroxyethyl methacrylate, methyl methacrylate, and the like. Among them, acrylic acid, benzyl acrylate, methacrylic acid and benzyl methacrylate are preferable.

The alkyl group having 1 to 3 carbon atoms in $R_{13}$ and $R_{14}$ of the general formula (3) includes a methyl group, an ethyl group, a propyl group, and the like.

The dialkylaminoalkyl group having 3 to 9 carbon atoms in $R_{14}$ of the general formula (3) includes, for example, a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The hydroxyalkyl group having 1 to 6 carbon atoms in $R_{14}$ of the general formula (3) includes, for example, a hydroxymethyl group, a hydroxyethyl group, a hydroxypropyl group, a hydroxybutyl group, a hydroxypentyl group, a hydroxyhexyl group, and the like, and a hydroxyethyl group is preferable.

Preferable specific examples of the general formula (3) include (meth)acrylamide, N,N-dimethylacrylamide, N,N-diethylacrylamide, hydroxyethyl (meth)acrylamide, 4-acryloyl morpholine, and the like. Among them, (meth)acrylamide, N,N-dimethylacrylamide and N,N-diethylacrylamide are preferable, and N,N-diethylacrylamide is particularly preferable.

Preferable specific examples of the general formula (4) include styrene, α-methylstyrene, N-vinylpyrrolidone, and the like. Among them, styrene and α-methylstyrene are preferable, and styrene is particularly preferable.

The alkyl group having 1 to 20 carbon atoms in $R_{16}$ of the general formula (5) may be any of the linear, branched and cyclic one, specifically including, for example, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a 3-methylpentyl group, a 2-methylpentyl group, a 1,2-dimethylbutyl group, an n-heptyl group, an isoheptyl group, a sec-heptyl group, an n-octyl group, an isooctyl group, a sec-octyl group, a n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a nonadecyl group, an icosyl group, and the like.

The hydroxyalkyl group having 1 to 10 carbon atoms in $R_{16}$ of the general formula (5) includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, and the like.

The halogenated alkyl group having 1 to 10 carbon atoms in $R_{16}$ of the general formula (5) includes, for example, a chloromethyl group, a chloroethyl group, a chloro-n-propyl group, a chloroisopropyl group, a chloro-n-butyl group, a chloro-tert-butyl group, a chloro-n-pentyl group, a chloro-n-hexyl group, a chloro-n-heptyl group, a chloro-n-octyl group, a chloro-n-nonyl group, a chloro-n-decyl group, a fluoromethyl group, a fluoroethyl group, a fluoro-n-propyl group, a fluoroisopropyl group, a fluoro-n-butyl group, a fluoro-tert-butyl group, a fluoro-n-pentyl group, a fluoro-n-hexyl group, a fluoro-n-heptyl group, a fluoro-n-octyl group, a fluoro-n-nonyl group, a fluoro-n-decyl group, and the like.

The alkylcycloalkyl group having 6 to 10 carbon atoms in $R_{16}$ of the general formula (5) includes, for example, a methylcyclopentyl group, an ethylcyclopentyl group, a propylcyclopentyl group, a methylcyclohexyl group, an ethylcyclohexyl group, a propylcyclohexyl group, a butylcyclohexyl group, a methylcycloheptyl group, an ethylcycloheptyl group, a propylcycloheptyl group, a methylcyclooctyl group, an ethylcyclooctyl group, and the like.

The halogenated cycloalkyl group having 6 to 7 carbon atoms in $R_{16}$ of the general formula (5) includes, for example, a chlorocyclohexyl group, a fluorocyclohexyl group, a bromocyclohexyl group, a chlorocycloheptyl group, a fluorocycloheptyl group, a bromocycloheptyl group, and the like.

The aryl group having 6 to 10 carbon atoms in $R_{16}$ of the general formula (5) includes a phenyl group, a naphthyl group, and the like.

The aryl group having 6 to 10 carbon atoms, which has an alkyl group having 1 to 6 carbon atoms as a substituent, in $R_{16}$ of the general formula (5), includes, for example, a methylphenyl group, an ethylphenyl group, an n-propylphenyl group, an n-butylphenyl group, an n-pentylphenyl group, an n-hexylphenyl group, a methylnaphthyl group, an ethylnaphthyl group, an n-propylnaphthyl group, and the like.

The halogenated aryl group having 6 to 10 carbon atoms in $R_{16}$ of the general formula (5) includes, for example, a chlorophenyl group, a fluorophenyl group, a chloronaphthyl group, a fluoronaphthyl group, and the like.

Preferable specific examples of the general formula (5) include maleic anhydride, maleimide, N-methylmaleimide, N-ethylmaleimide, N-butylmaleimide, N-octylmaleimide, N-dodecylmaleimide, N-(2-ethylhexyl)maleimide, N-(2-hydroxyethyl)maleimide, N-(2-chlorohexyl)maleimide, N-cyclohexylmaleimide, N-(2-methylcyclohexyl)maleimide, N-(2-ethylcyclohexyl)maleimide, N-(2-chlorocyclohexyl)maleimide, N-phenylmaleimide, N-(2-methylphenyl)maleimide, N-(2-ethylphenyl)maleimide, N-(2-chlorophenyl)maleimide, and the like, and among them, N-phenylmaleimide is preferable.

The copolymer of the present invention specifically includes those having monomer unit combinations described in the following table. Among them, the combinations 1, 5, 6, and 7 are preferable, and in the combination 1, a combination comprising the compound represented by the general formula (1) and two kinds of the compound represented by the general formula (2) is preferable.

| | Compound from which monomer unit is derived | | |
|---|---|---|---|
| Combination 1 | General formula (1) | General formula (2) | |
| Combination 2 | General formula (1) | General formula (3) | |
| Combination 3 | General formula (1) | General formula (4) | |
| Combination 4 | General formula (1) | General formula (5) | |
| Combination 5 | General formula (1) | General formula (2) | General formula (3) |
| Combination 6 | General formula (1) | General formula (2) | General formula (4) |
| Combination 7 | General formula (1) | General formula (2) | General formula (5) |

Weight ratio of the monomer unit derived from the compound represented by the general formula (1), and the monomer unit derived from compound represented by the general formula (2), the general formula (3), the general formula (4), or the general formula (5) may be set as appropriate, depending on kinds of the monomer units to be used, however, the monomer unit derived from the compound represented by the general formula (1) is usually 1 to 90% by weight, and preferably 5 to 85% by weight, relative to total weight of the resulting polymer.

Preferable specific examples of the copolymer of the present invention include polymers comprising the monomer unit derived from the compound represented by the general formula (1), and one kind or two kinds of the monomer unit derived from the compound represented by the following general formula (2).

(2')

(wherein $R_{11}$ is the same as described above; $R'_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, or an alkoxyalkyl group having 2 to 9 carbon atoms.)

Specific examples of the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, and the alkoxyalkyl group having 2 to 9 carbon atoms, in $R'_{12}$ of the general formula (2'), include the same ones as those in $R_{12}$ of the general formula (2).

As $R'_{12}$ of the general formula (2'), a hydrogen atom, an alkyl group having 1 to 18 carbon atoms, an arylalkyl group having 7 to 13 carbon atoms, and the like, are preferable, and a hydrogen atom, and the arylalkyl group having 7 to 13 carbon atoms are more preferable.

Preferable specific examples of the compound represented by the general formula (2') include acrylic acid, benzyl acrylate, methacrylic acid, benzyl methacrylate, and the like, and among them, methacrylic acid and benzyl methacrylate are preferable.

[Production Method for the Polymer of the Present Invention]

The polymer of the present invention is produced, for example, as follows. That is, the polymer of the present invention can be obtained by subjecting the compound of the present invention obtained as described above to a polymerization reaction known per se. When the polymer of the present invention is a copolymer, in the polymerization reaction, after mixing the compound of the present invention with one to two kinds of the compound represented by the general formula (2), the general formula (3), the general formula (4) or the general formula (5), so that ratio of the monomer unit derived from each monomer in the finally obtained polymer attains as described above, polymerization may be carried out.

The above-described polymerization reaction is carried out, for example, as follows. That is, the compound represented by the general formula (1) having the anion of the present invention, or the compound represented by the general formula (1) having the anion of the present invention and one to two kinds of compound represented by the general formula (1), the general formula (3), the general formula (4) or the general formula (5) are dissolved in an appropriate solvent, for example, toluene, 1,4-dioxane, tetrahydrofuran, isopropanol, methyl ethyl ketone, propylene glycol monomethyl ether acetate, and the like, of 1 to 10 times volume relative to total volume thereof. Then, in the presence of a polymerization initiator, for example, azoisobutyronitrile, 2,2'-azobis(2,4-dimethylvaleronitrile), 2,2'-azobis(2-methylpropionate), 2,2'-azobis(2-methylbutyronitrile), benzoylperoxide, lauroyl peroxide, and the like, of 0.01 to 30% by weight relative to total amount of the dissolved compounds, a reaction may be carried out at 50 to 150° C. for 1 to 48 hours. After the reaction, treatment may also be carried out according to a conventional method for polymer acquisition.

[Coloring Composition]

The coloring composition of the present invention is the one containing at least one kind of the compound or the polymer of the present invention. The coloring composition is the one having less fading caused by heating, and still more, it is capable of forming an excellent colored cured film having heat resistance. Therefore, it can be used in an application of color pixel formation such as a color filter used in a liquid crystal display (LCD) or a solid-state imaging element (CCD, CMOS, and the like), or in applications of printing ink, inkjet ink, paint, and the like; and particularly, it can be suitably used for the color filter of the liquid crystal display. Still more, the coloring composition of the present invention can be also used as a colored resin molded product by molding to a sheet, a film, a bottle, a cup, and the like, using a conventionally known molding method.

Accordingly, it can also be used in applications of spectacles, contact lens, color contact lens, and the like; and it can be used in similar applications also by making a multilayered structure with a known resin. In addition, it can also be used in applications of, for example, an optical film, a hair coloring agent, a labeling material for a compound or a biological material, a material of an organic solar battery, and the like. The coloring composition of the present invention may contain an additive used in this field usually, and the like, depending on each application, besides the compound or the polymer of the present invention.

For example, in the case of using the coloring composition of the present invention as a colored resin, the coloring composition of the present invention is preferably the one which contains at least one or more kinds of the compound or the polymer of the present invention, as well as which is mixed with other resins, and more preferably the one which has one or more kinds of the polymer of the present invention and is mixed with other resins. The other resins are not especially limited, and include, for example, a polyolefin resin, a polystyrene resin, a polyester resin, a polyamide resin, a polyurethane resin, a polycarbonate resin, an epoxy resin, an acrylic resin, an acrylonitrile resin, an ABS resin, and the like. More specifically, a homopolymer or a copolymer derived from the compound represented by the general formula (2), the general formula (3), the general formula (4) and/or the general formula (5) is preferable, and the homopolymer derived from the compound represented by the general formula (2), the general formula (3), the general formula (4) or the general formula (5) is more preferable. As the homopolymer, the homopolymer derived from the compound represented by the general formula (2) is preferable, and the homopolymer derived from the compound represented by the general formula (2') is more preferable. In addition, in the case of mixing with the other resins, mixing ratio thereof may be set appropriately depending on desired color of the colored resin. In the case of using the coloring composition of the present invention as the colored resin, it may be used after molding it by a molding method known per se. Further, the coloring composition of the present invention, if necessary, may contain an additive usually used in this field, such as a lubricant, an antistatic agent, a UV inhibitor, an antioxidant, a light stabilizer, a dispersing agent, a processing stabilizer, a processing aid, an impact modifier, fillers, a reinforcing agent, a flame-proofing agent, a plasticizer, a foaming agent, and the like; besides the compound or the polymer of the present invention and the other resins; within a range not interfering with the objects and effects of the present invention. The coloring composition of the present invention has less elution of a dye even in contact with a solvent and excellent weather resistance, in the case where it is used as the colored resin.

For example, in the case of using the coloring composition of the present invention in an application of color pixel formation, the coloring composition of the present invention is preferably the one containing at least one kind or more of the compound or the polymer of the present invention, and a polymerization initiator, a binder resin, as well as a radically polymerizable monomer or oligomer, and if necessary, which may contain a pigment, a solvent, a silane coupling agent, as well as a cross-linking agent, and the like. The coloring composition contains 1 to 50%, preferably 5 to 30% of the compound or the polymer of the present invention, relative to weight of the coloring composition. It should be noted that, weight of the coloring composition referred to herein means weight of solid components excluding the solvent, and means the same hereafter in the present application.

As the above-described polymerization initiator, a known thermal polymerization initiator or a photo polymerization initiator can be used, and a photo polymerization initiator is preferable. Specifically, it includes an acetophenone type such as diethoxyacetophenone, 2-hydroxy-2-methyl-1-phenylpropane-1-one, benzyldimethylketal, 1-(4-isopropylphenyl)-2-hydroxy-2-methylpropane-1-one, 4-(2-hydroxyethoxy)phenyl-(2-hydroxy-2-propyl)ketone, 1-hydroxycycylohexyl-phenylketone, 2-methyl-2-morpholino(4-thiomethylphenyl)propane-1-one and 2-benzyl-2-dimethylamino-1-(4-morpholinophenyl)-butanone; a benzoin type such as benzoin, benzoin isopropyl ether and benzoin isobutyl ether; an acyl phosphine oxide type such as 2,4,6-trimethylbenzoyldiphenyl phosphine oxide; a benzyl, a methyl phenylglyoxylate type; a benzophenone type such as benzophenone, methyl o-benzoylbenzoate, 4-phenylbenzophenone, 4,4'-dichlorobenzophenone, hydroxybenzophenone, 4-benzoyl-4'-methyl-diphenylsulfide, acrylated benzophenone, 3,3',4,4'-tetra(tert-butylperoxycarbonyl)benzophenone and 3,3'-dimethyl-4-methoxybenzophenone; a thioxanthone type such as 2-isopropylthioxanthone, 2,4-dimethylthioxanthone, 2,4-diethylthioxanthone and 2,4-dichlorothioxanthone; an aminobenzophenone type such as Michler's ketone and 4,4'-diethylaminobenzophenone; an oxime ester type such as 1-[4-(phenylthio)phenyl]-1,2-octanedione-2-(o-benzoyloxime) and 1-[6-(2-methylbenzoyl)-9-ethyl-9H-carbazol-3-yl]ethanone-o-acetyloxime; 10-butyl-2-chloroacridone, 2-ethylanthraquinone, 9,10-Phenanthrenequinone, camphor quinone; and the like.

The polymerization initiator may be contained alone, or in two or more kinds. Content thereof is 1 to 50% by weight, and preferably 5 to 30% by weight, relative to weight of the coloring composition.

The above-described binder resin includes, for example, an ethylenically unsaturated monomer having at least one of a carboxy group or a hydroxy group; a copolymer of the ethylenically unsaturated monomer and an ethylenically unsaturated monomer having an aromatic hydrocarbon group or an aliphatic hydrocarbon group; the one having an epoxy group at the side chain or the terminal, and the like, of the copolymer; and the one to which an acrylate is added; and the like. They may be used alone, or in combination of two or more kinds.

Specific examples of the ethylenically unsaturated monomer having the carboxy group include unsaturated monocarboxylic acids such as acrylic acid, methacrylic acid, benzyl methacrylate, crotonic acid, α-chloroacrylic acid, ethacrylic acid and cinnamic acid; unsaturated dicarboxylic acids (anhydrides) such as maleic acid, maleic anhydride, fumaric acid, itaconic acid, itaconic anhydride, citraconic acid, citraconic anhydride and mesaconic acid; tri or more polyvalent unsaturated carboxylic acids (anhydrides), 2-(meth)acryloyloxyethyl hexahydrophthalate, 2-methacryloyloxyethyl 2-hydroxypropylphthalate, 2-acryloyloxyethyl 2-hydroxyethylphthalate; and the like.

Content of the binder resin is 10% by weight to 50% by weight, and preferably 20% by weight to 50% by weight, relative to weight of the coloring composition.

The above-described radically polymerizable monomer or oligomer includes, as one example, polyethylene glycol diacrylate (the one having 2 to 14 ethylene groups), polyethylene glycol dimethacrylate (the one having 2 to 14 ethylene groups), trimethylolpropane diacrylate, trimethylolpropane dimethacrylate, trimethylolpropane triacrylate, trimethylolpropane trimethacrylate, trimethylolpropane ethoxytriacrylate, trimethylolpropane ethoxytrimethacrylate, trimethylolpropane propoxytriacrylate, trimethylolpropane propoxytrimethacrylate, tetramethylohnethane triacrylate, tetramethylolmethane trimethacrylate, tetramethylolmethane tetraacrylate, tetramethylolmethane tetramethacrylate, polypropyleneglycol diacrylate (the one having 2 to 14 propylene groups), polypropylene glycol dimethacrylate (the one having 2 to 14 propylene groups), dipentaerythritol pentaacrylate, dipentaerythritol pentamethacrylate, dipentaerythritol hexaacrylate, dipentaerythritol hexamethacrylate, ethoxylated pentaerythritol tetraacrylate (the one having 40 or less ethoxy groups), propoxylated pentaerythritol tetraacrylate (the one having 40 or less propoxy groups), ethoxylated trimethylolpropane triacrylate (the one having 40 or less ethoxy groups), propoxylated trimethylolpropane triacrylate (the one having 40 or less propoxy groups), bisphenol A polyoxyethylene diacrylate, bisphenol A polyoxyethylene dimethacrylate, bisphenol A dioxyethylene diacrylate, bisphenol A dioxyethylene dimethacrylate, bisphenol A trioxyethylene diacrylate, bisphenol A trioxyethylene dimethacrylate, bisphenol A decaoxyethylene diacrylate, bisphenol A decaoxyethylene dimethacrylate, isocyanuric acid ethoxy modified triacrylate, an esterified product with a polyvalent carboxylic acid (phthalic anhydride, and the like) and a compound having a hydroxy group and an ethylenically unsaturated group (β-hydroxyethyl acrylate, β-hydroxyethyl methacrylate, and the like), an alkyl ester of acrylic acid or methacrylic acid (acrylic acid methyl ester, methacrylic acid methyl ester, acrylic acid ethyl ester, methacrylic acid ethyl ester, acrylic acid butyl ester, methacrylic acid butyl ester, acrylic acid 2-ethylhexyl ester, methacrylic acid 2-ethylhexyl ester, and the like), 2-hydroxyethyl acrylate, 2-hydroxyethyl methacrylate, phenoxyethyl acrylate, phenoxyethyl methacrylate, N,N-dimethylacrylamide, N,N-dimethylaminoethyl acrylate, a quaternary chloride of N,N-dimethylaminoethyl acrylate by methyl chloride, a quaternary chloride of N,N-dimethylaminopropylacrylamide by methyl chloride, acryloylmorpholine, N-isopropylacrylamide, N,N-diethylacrylamide, and the like. Among them, dipentaerythritol pentaacrylate, dipentaerythritol pentamethacrylate, dipentaerythritol hexaacrylate and dipentaerythritol hexamethacrylate are preferable, and dipentaerythritol pentaacrylate and dipentaerythritol hexaacrylate are more preferable.

Content of the radically polymerizable monomer or oligomer is usually 20% by weight to 60% by weight, and preferably 30% by weight to 60% by weight, and more preferably 40% by weight to 60% by weight, relative to weight of the coloring composition. Particularly, in the case of using with the compound of the present invention, higher heat resistance effect can be exerted by using the radically polymerizable monomer or oligomer in 40% by weight to 60% by weight.

The above-described pigment may be the pigment that is used to prepare a colored pattern of red color, blue color or green color, and for example, a phthalocyanine-type pigment, and the like, is included. The phthalocyanine-type pigment includes the one containing magnesium, titanium, iron, cobalt, nickel, copper, zinc, or aluminum in central metal; and specifically includes C.I. pigment red 1, C.I. pigment red 2, C.I. pigment red 5, C.I. pigment red 17, C.I. pigment red 31, C.I. pigment red 32, C.I. pigment red 41, C.I. pigment red 122, C.I. pigment red 123, C.I. pigment red 144, C.I. pigment red 149, C.I. pigment red 166, C.I. pigment red 168, C.I. pigment red 170, C.I. pigment red 171, C.I. pigment red 175, C.I. pigment red 176, C.I. pigment red 177, C.I. pigment red 178, C.I. pigment red 179, C.I. pigment red 180, C.I. pigment red 185, C.I. pigment red 187, C.I. pigment red 202, C.I. pigment red 206, C.I. pigment red 207, C.I. pigment red 209, C.I. pigment red 214, C.I. pigment red 220, C.I. pigment red 221, C.I. pigment red 224, C.I. pigment red 242, C.I. pigment red 243, C.I. pigment red 254, C.I. pigment red 255, C.I. pigment red 262, C.I. pigment red 264, C.I. pigment red 272, C.I. pigment blue 15, C.I. pigment blue 15:1, C.I. pigment blue 15:2, C.I. pigment blue 15:3, C.I. pigment blue 15:4, C.I. pigment blue 15:5, C.I. pigment blue 15:6, C.I. pigment blue 16, C.I. pigment blue 17:1, C.I. pigment blue 75, C.I. pigment blue 79, C.I. pigment green 7, C.I. pigment green 36, C.I. pigment green 37, C.I. pigment green 58, chloroaluminum phthalocyanine, hydroxyaluminum phthalocyanine, aluminum phthalocyanine oxide, and zinc phthalocyanine.

Content of the pigment is 10 to 50% by weight, and preferably 10 to 30% by weight, relative to weight of the coloring composition.

In the case where the coloring composition of the present invention contains the pigment, it is preferable to contain a pigment dispersant. The pigment dispersant includes, for example, polyamide amine and a salt thereof, polycarboxylic acid and a salt thereof, a high molecular weight unsaturated acid ester, modified polyurethane, modified polyester, modified poly(meth)acrylate, a (meth)acrylic copolymer, a naphthalene sulfonic acid/formalin condensate, a polyoxyethylene alkyl phosphoric acid ester, a polyoxyethylene alkylamine, an alkanol amine, and the like. The pigment dispersant may be used alone, or in combination of two or more kinds. Content thereof is usually 1 to 80% by weight, and preferably 10 to 60% by weight, relative to weight of the pigment.

The above-described solvent may be appropriately selected depending on the components contained in the coloring composition. Specifically, it includes, for example, ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, methyl 2-methoxy-2-methylpropionate, ethyl 2-ethoxy-2-nethylpropionate, methyl pyruvate, ethyl pyruvate, propyl pyruvate, methyl acetoacetate, ethyl acetoacetate, methyl 2-oxobutanoate, ethyl 2-oxobutaanoate, diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, methyl ethyl ketone, cyclohexanone, 2-heptanone, 3-heptanone, and the like. Content of the solvent is an amount that concentration of the coloring composition of the present invention attains 10% by weight to 80% by weight in the solvent.

The above-described silane coupling agent is used in the case of bonding to a substrate, such as glass. As the silane coupling agent, a conventionally known one usually used in this field can be used, and it includes a silane coupling agent having, for example, an epoxy group, a thiol group, a hydroxy group, an amino group, an ureido group, a vinyl group, an acryloyl group, and the like, as a reactive organic functional group. Specifically, it includes β-(3,4-epoxycyclohexyl)ethyltrimethoxysilane, γ-glycidooxypropyltrimethoxysilane, γ-mercaptopropyltrimethoxysilane, γ-aminopropyltriethoxysilane, N-β-(aminoethyl)-γ-aminopropyltrimethoxysilane, γ-ureidopropyltriethoxysilane, vinyltriethoxysilane, vinyl-tris(β-methoxyethoxy)silane and γ-methacryloxypropyltrimethoxysilane. The silane coupling agent may be used usually in the amount of 0.1% by weight to 10% by weight, and preferably 1% by weight to 5% by weight, in the reaction solution.

The above-described cross-linking agent is not especially limited as long as it is the one which is capable of carrying out film curing by a cross-linking reaction, and includes, for example, (a) an epoxy resin, (b) a melamine compound, a guanamine compound, a glycoluril compound or a urea compound, substituted with at least one substituent selected from a methylol group, an alkoxymethyl group and an acyloxymethyl group, and (c) a phenol compound, a naphthol compound or a hydroxyanthracene compound, substituted with at least one substituent selected from a methylol group, an alkoxymethyl group and an acyloxymethyl group; and among them, a polyfunctional epoxy resin is preferable.

Content of the cross-linking agent is 10% by weight to 50% by weight, and preferably 20% by weight to 50% by weight, relative to weight of the coloring composition.

The coloring composition of the present invention may contain a polymerization inhibitor, a surfactant, an additive, and the like, in addition to the above-described ones, and they are not especially limited, as long as they are those known per se, and the use amount is not limited, as long as it is the amount usually used in this field.

The coloring composition of the present invention is prepared by mixing with the above-described components.

The present invention is described below in further detail by Examples, however, the present invention should not be limited to these Examples.

EXAMPLES

Example 1

Synthesis of a Polymerizable Coloring Compound (Dye Monomer 1)

(1) Construction of a skeleton of a coloring compound

Into a round-bottom flask equipped with a stirring apparatus, 5.0 g of rhodamine 6G (compound 1) (0.010 mol, produced by Wako Pure Chemical Industries, Ltd.), 10.8 g of 2-aminoethanol (compound 2) (0.177 mol, produced by Wako Pure Chemical Industries, Ltd.), and 50 mL of ethanol (EtOH) were added, and reacted at room temperature for 6 hours. Into there, 50 mL of ion-exchanged water was added to stir at room temperature for 30 minutes, and then deposited crystal was filtrated to obtain 4.5 g (yield: 95%) of a compound 3.

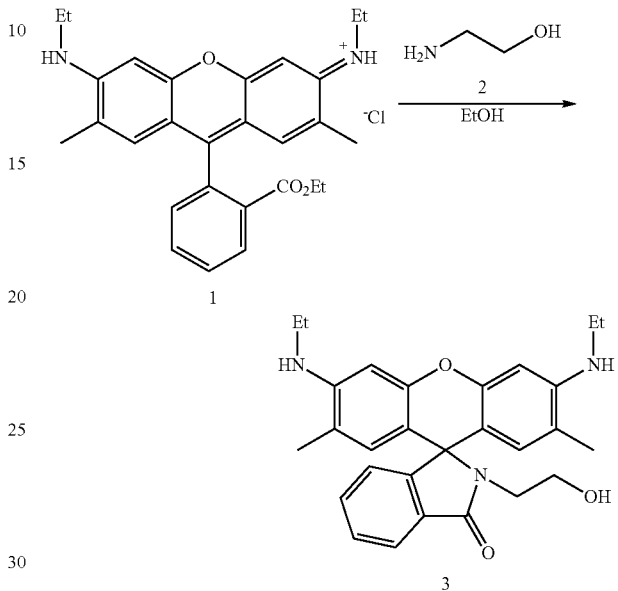

(2) Introduction of a Polymerizable Group

Into a round-bottom flask equipped with a stirring apparatus, 1.5 g (0.003 mol) of the compound 3 obtained in (1), 0.8 g of 2-methacryloyloxyethyl succinate (compound 4) (0.004 mol, product name: NK ester SA, produced by Shin-Nakamura chemical Co., Ltd.), 0.1 g of 4-dimethylaminopyridine (DMAP) (0.001 mol, produced by Wako Pure Chemical Industries, Ltd.), 1.0 g of 1-ethyl-3-(3-dimethylaminopropyl)carbodiimide hydrochloride (WSC) (0.005 mol, produced by Toyobo Co., Ltd.), and 20 mL of methylene chloride were added, and reacted at room temperature for 24 hours. After washing with ion exchanged water, the solvent was removed by concentration under reduced pressure to obtain 2.2 g (yield: 110%) of a red solid monomer (compound 5) containing the compound 4 used in excess.

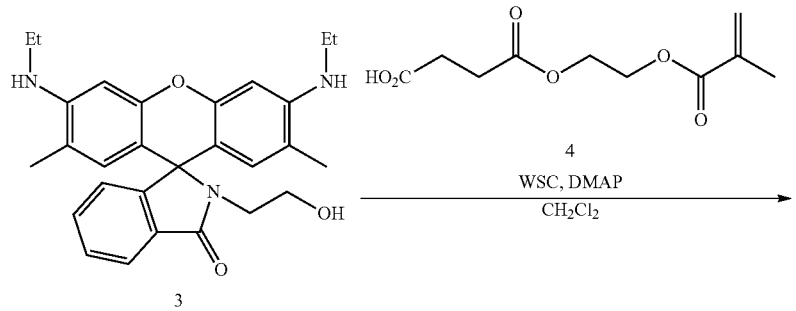

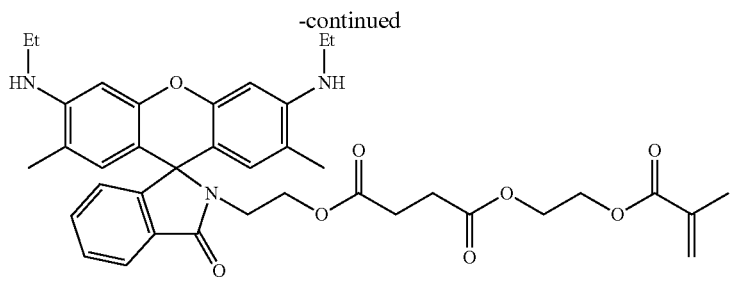

5

(3) Salt Formation Reaction

Into a round-bottom flask equipped with a stirring apparatus, 1.0 g (0.002 mol) of the monomer obtained in (2) (compound 5), and 20 mL of ethanol were added and dissolved. Into there, 1.1 g of lithium salt of tetrakis(pentafluorophenyl)boron (IV) (0.002 mol, produced by Tosoh Finechem Corp.) and 4 mL of 1 mol/L hydrochloric acid were added, and reacted at 40° C. for 3 hours. After dilution with 40 mL of methylene chloride and washing with ion-exchanged water, the solvent was removed by concentration under reduced pressure to obtain 1.8 g (yield: 86%) of a dye monomer 1 (compound 6) as a dark brown solid, having a tetrakis(pentafluorophenyl)boron (IV) anion as a counter anion.

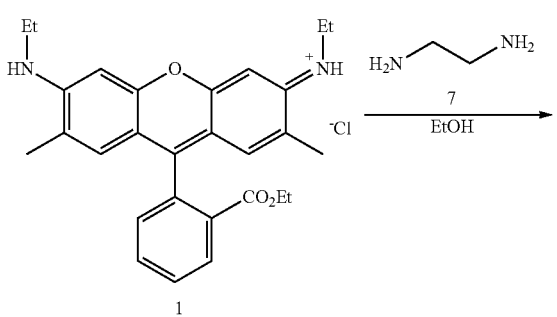

Example 2

Synthesis of a Polymerizable Coloring Compound (Dye Monomer 2)

(1) Construction of a Skeleton of a Coloring Compound

Into a round-bottom flask equipped with a stirring apparatus, 7.1 g of rhodamine 6G (compound 1) (0.015 mol, produced by Wako Pure Chemical Industries, Ltd.), 15.1 g of ethylenediamine (compound 7) (0.251 mol, produced by Wako Pure Chemical Industries, Ltd.), and 30 mL of ethanol were added, and reacted at room temperature for 6 hours. Into there, 30 mL of ion-exchanged water was added to stir at room temperature for 1 hour, and then deposited crystal was filtrated to obtain 6.4 g (yield: 95%) of a compound 8.

-continued

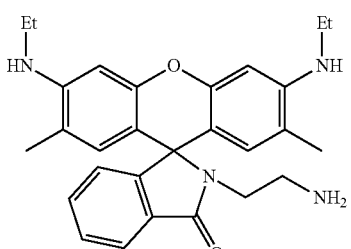

(2) Introduction of a Polymerizable Group

Into a round-bottom flask equipped with a stirring apparatus, 1.0 g (0.002 mol) of the compound 8 obtained in (1), 0.4 g of 2-isocyanatoethyl methacrylate (compound 9) (0.003 mol, produced by Wako Pure Chemical Industries, Ltd.), and 15 mL of toluene were added, and reacted at room temperature for 4 hours. Deposited crystal was filtrated to obtain 1.2 g (yield: 88%) of a red solid monomer (compound 10).

with 40 mL of methylene chloride and washing with ion-exchanged water, the solvent was removed by concentration under reduced pressure to obtain 2.2 g (yield: 100%) of a dye monomer 2 (compound 11) as a dark brown solid, having a tetrakis(pentafluorophenyl)boron (IV) anion as a counter anion.

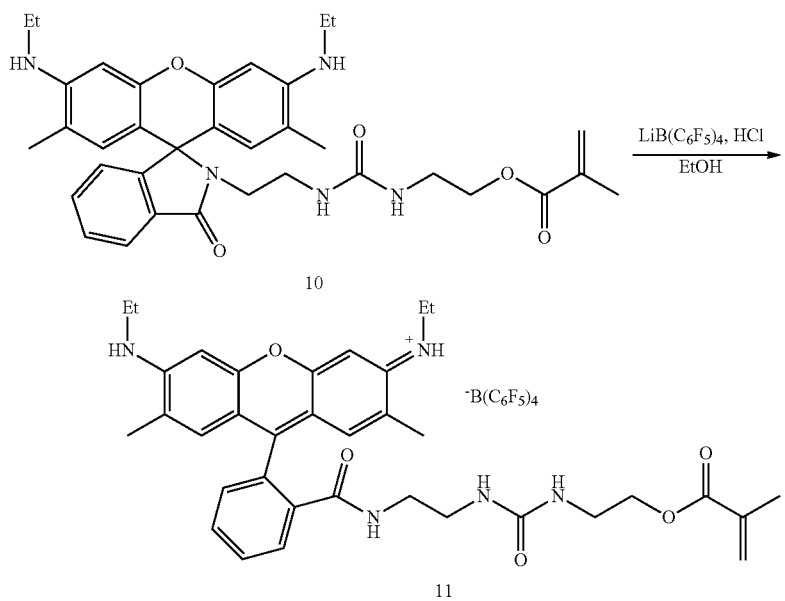

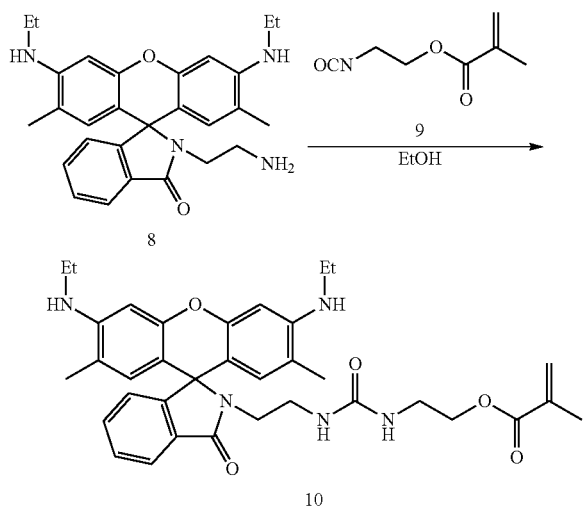

(3) Salt Formation Reaction

Into a round-bottom flask equipped with a stirring apparatus, 1.0 g (0.002 mol) of the monomer obtained in (2) (compound 10), and 20 mL of ethanol were added and dissolved. Into there, 1.1 g of lithium salt of tetrakis(pentafluorophenyl)boron (IV) (0.002 mol, produced by Tosoh Finechem Corp.) and 5 mL of 1 mol/L hydrochloric acid were added, and reacted at 40° C. for 3 hours. After dilution Example 3

Synthesis of Polymerizable Coloring Compounds (Dye Monomers 3 and 4)

(1) Amidation Reaction

Into a round-bottom flask equipped with a stirring apparatus, 25.0 g of rhodamine 6G (compound 1) (0.052 mol, produced by Wako Pure Chemical Industries, Ltd.), and 35.0 g of 1-piperazine ethanol (compound 12) (0.269 mol, produced by Tokyo Chemical Industry Co., Ltd.) were added, and reacted at 90° C. for 40 hours. After dilution of the reaction solution with 30 mL of methanol, it was poured into 500 mL of ion-exchanged water, and then precipitate was filtered off. After adding 70 g of sodium chloride, solvent extraction was carried out twice using 300 mL of a mixed solution of 2-propanol/methylene chloride (2-propanol: methylene chloride=3:2). After adding 50 g of sodium sulfate for dehydration and filtering, the solvent was removed by concentration under reduced pressure. After adding 150 mL of methylene chloride and stirring at room temperature for 0.5 hour, crystal was filtrated to obtain 9.5 g (yield: 35%) of an amide compound (compound 13).

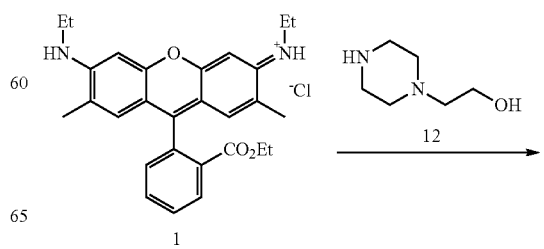

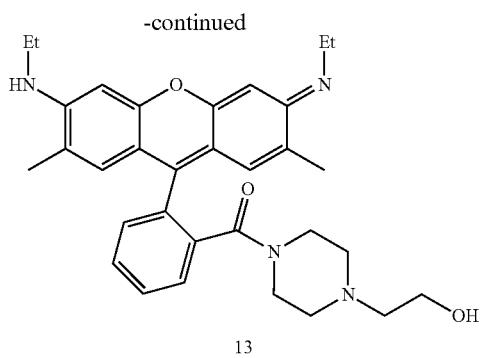

13

(2) Introduction of a Polymerizable Group

Into a round-bottom flask equipped with a stirring apparatus, 11.2 g (0.021 mol) of the amide compound obtained in (1) (compound 13), 227.4 g of methacrylic acid (compound 14) (2.641 mol, produced by Wako Pure Chemical Industries, Ltd.), 23.0 g of methacrylic anhydride (compound 15) (0.149 mol, produced by Wako Pure Chemical Industries, Ltd.), 560 mL of chloroform, and 142 mg of p-methoxyphenol, as a polymerization inhibitor, were added and reacted at room temperature for 45 hours. Further, 21 mL of methanol was added and stirred at room temperature for 1 hour, and then chloroform was removed by concentration under reduced pressure. The resulting reaction solution was poured into 400 mL of diethyl ether, and deposited crystal was filtrated. After adding 300 mL of methylene chloride and 100 mL of ion-exchanged water for liquid separation, collected organic layer was washed with 100 mL of ion-exchanged water. After adding 50 g of sodium sulfate for dehydration and filtering, the solvent was removed by concentration under reduced pressure. After adding 150 mL of methylene chloride, 40 mL of ethanol and 1.5 mL of concentrated hydrochloric acid, and stirring at room temperature for 1 hour, the solvent was removed by concentration under reduced pressure. After addition of 150 mL of diisopropyl ether, deposited crystal was filtrated to obtain 7.9 g (yield: 59%) of a dye monomer 3 (compound 16).

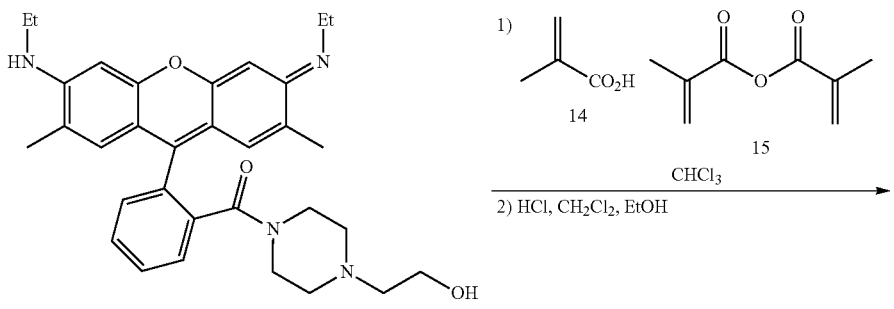

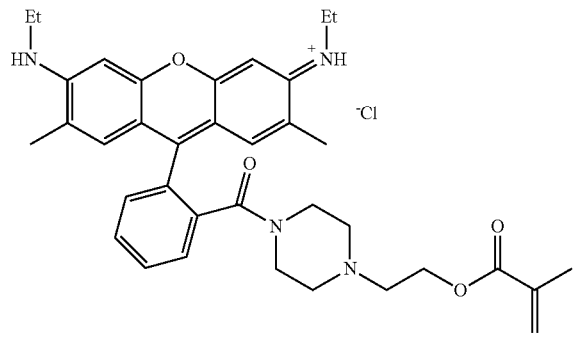

(3) Salt Formation Reaction

Into a round-bottom flask equipped with a stirring apparatus, 3.3 g (0.005 mol) of the dye monomer 3 obtained in (2) (compound 16), and 100 mL of methylene chloride were added and dissolved. Into there, 4.0 g of lithium salt of tetrakis(pentafluorophenyl)boron (IV) (0.005 mol, produced by Tosoh Finechem Corp.) and 10 mL of 1 mol/L hydrochloric acid were added, and reacted at room temperature for 1.5 hour. After washing the reaction solution with 40 mL of ion-exchanged water, the solvent was removed by concentration under reduced pressure to obtain 6.4 g (yield: 97%) of a dye monomer 4 (compound 17) as a dark brown solid, having a tetrakis(pentafluorophenyl)boron (IV) anion as a counter anion.

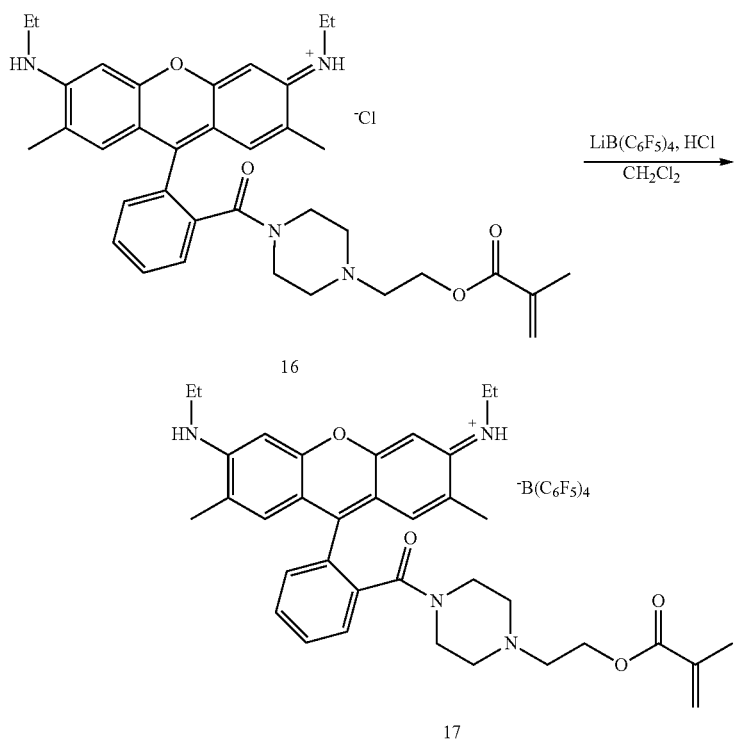

Comparative Example 1

Synthesis of a Dye Monomer 5

Into a round-bottom flask equipped with a stirring apparatus, 47.9 g of rhodamine B (compound 18) (0.10 mol, produced by Wako Pure Chemical Industries, Ltd.), 500 mL of methylene chloride, 15.6 g of hydroxyethyl methacrylate (compound 19) (0.12 mol, produced by Wako Pure Chemical Industries, Ltd.), 4.9 g of 4-dimethylaminopyridine (0.04 mol, produced by Wako Pure Chemical Industries, Ltd.), and 32.6 g of 1-ethyl-3-(3-dimethylaminopropyl)carbodiimide hydrochloride (0.17 mol, produced by Toyobo Co., Ltd.) were added and stirred at room temperature for 24 hours to carry out a reaction. After completion of the reaction, the organic layer was washed with about 500 mL of ion-exchanged water. Next, 50 g of sodium sulfate was added for dehydration, and 10 mg of p-methoxyphenol (produced by Wako Pure Chemical Industries, Ltd.) was added as a polymerization inhibitor, and the solvent was removed under reduced pressure to obtain 44 g (yield: 74.6%) of red solid (compound 20). This was referred to as the dye monomer 5.

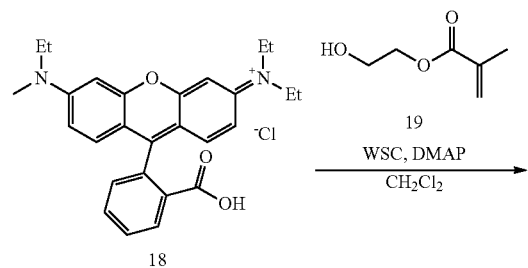

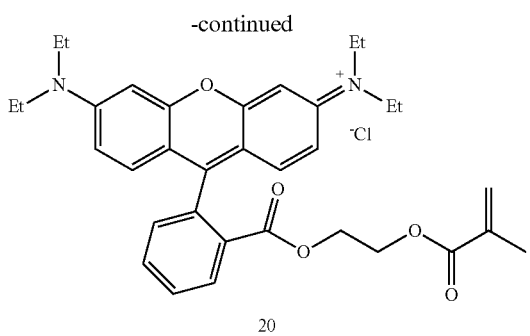

Comparative Example 2

Synthesis of a Dye Monomer 6

Into a 500 mL round-bottom flask equipped with a stirring apparatus, 11.8 g (0.020 mol) of the dye monomer 5 obtained in Comparative Example 1, 6.6 g of dodecylbenzene sulfonic acid (0.020 mol), 150 mL of methylene chloride, 150 mL of ion-exchanged water were added, and then stirred at room temperature for 30 minutes to carry out a salt exchange reaction. After completion of the reaction, the organic layer was washed four times with about 150 mL of ion-exchanged water. Next, 5 mg of p-methoxyphenol (produced by Wako Pure Chemical Industries, Ltd.) was added, and concentrated under reduced pressure to obtain 17.0 g (yield: 93.4%) of red viscous liquid, where chloride ion of the dye monomer 3 was exchanged to a dodecylbenzene sulfonic acid anion. This was referred to as the dye monomer 6.

Comparative Example 3

Synthesis of a Dye Monomer 7

A dye monomer was synthesized by a similar method as in Comparative Example 2, except for using 3.8 g of p-toluene sulfonic acid mono-hydrate (0.020 mol), instead of 6.6 g of dodecylbenzene sulfonic acid. As a result, 13.6 g (yield: 91.0%) of red viscous liquid was obtained, where a dodecylbenzene sulfonic acid anion of the dye monomer 6 was exchanged to a p-toluene sulfonic acid anion. This was referred to as the dye monomer 7.

Example 4

Evaluation of Heat Resistance of a Monomer (230° C. for 0.5 Hour)
Heat resistance of the dye monomer 1 obtained in Example 1 was evaluated as follows.
(1) Synthesis of a Polymer not Containing a Dye
Into a 500 mL round-bottom flask equipped with a stirring apparatus, a cooling condenser, a thermometer and a nitrogen introducing tube, 98.5 g of propylene glycol monomethyl ether acetate was charged, and heated until inner temperature reached to 90° C. under nitrogen gas flow. Next, a solution mixed with 186.2 g of benzyl methacrylate, 25.6 g of methacrylic acid, 33.9 g of dimethyl 2,2'-azobis(2-methylpropionate) (polymerization initiator V-601, produced by Wako Pure Chemical Industries, Ltd.) and 98.5 g of propylene glycol monomethyl ether acetate was dropped therein taking 2 hours. After that, the resulting solution was reacted at 90° C. for 2 hours, and then after raising temperature to 100° C., it was reacted for 1 hour. After the reaction, the solution was cooled down to room temperature, and 171.5 g of propylene glycol monomethyl ether acetate was added and diluted to obtain a pale yellow transparent polymer solution. This was referred to as a polymer A. It should be noted that concentration of non-volatile components of the polymer A was 35.9%.
(2) Preparation of a Mixed Solution of a Dye Monomer
To prepare the mixed solution B of the dye monomer, 0.5 g of the dye monomer 1, 52.9 g of the polymer A and 3.2 g of propylene glycol monomethyl ether acetate were mixed.
(3) Evaluation of Heat Resistance
The mixed solution B of the dye monomer was spin coated onto 3 inch glass wafer (Eagle XG, manufactured by Corning Inc.), and dried for 90 seconds on a hot plate heated at 90° C., to obtain a thin film having a film thickness of 1 μm. Absorbance (λa) at the maximum absorption wavelength of the resulting thin film was measured using a spectrophotometer (Spectrophotometer UV-2550, manufactured by Shimadzu Corp.). After that, the glass wafer was heated for 30 minutes on the hot plate heated at 230° C., and then absorbance (λb) at the maximum absorption wavelength was measured again. From values of λa and λb, dye residual ratio (%) was determined from the following equation.

Dye residual ratio (%)=(λb/λa)×100

Example 5

Evaluation of Heat Resistance of a Monomer (230° C. for 0.5 Hour)
Heat resistance was evaluated similarly as in Example 4, except for using the dye monomer 2 obtained in Example 2, instead of the dye monomer 1.

Example 6

Evaluation of Heat Resistance of a Monomer (230° C. for 0.5 Hour)
Heat resistance was evaluated similarly as in Example 4, except for using the dye monomer 4 obtained in Example 3, instead of the dye monomer 1.

Comparative Example 4

Evaluation of Heat Resistance of a Monomer (230° C. for 0.5 Hour)
Heat resistance was evaluated similarly as in Example 4, except for using the dye monomer 5 obtained in Comparative Example 1, instead of the dye monomer 1.

Comparative Example 5

Evaluation of Heat Resistance of a Monomer (230° C. for 0.5 Hour)
Heat resistance was evaluated similarly as in Example 4, except for using the dye monomer 6 obtained in Comparative Example 2, instead of the dye monomer 1.

Comparative Example 6

Evaluation of Heat Resistance of a Monomer (230° C. for 0.5 Hour)
Heat resistance was evaluated similarly as in Example 4, except for using the dye monomer 7 obtained in Comparative Example 3, instead of the dye monomer 1.

Comparative Example 7

Evaluation of Heat Resistance of a Monomer (230° C. for 0.5 Hour)
Heat resistance was evaluated similarly as in Example 4, except for using the dye monomer 3 obtained in Example 3 (2), instead of the dye monomer 1.

Comparative Example 8

Evaluation of Heat Resistance of a Monomer (230° C. for 0.5 Hour)
Heat resistance was evaluated similarly as in Example 4, except for using rhodamine 6G, instead of the dye monomer 1.
Results of Examples 4 to 6 and Comparative Examples 4 to 8 are shown in Table 1.

TABLE 1

|  |  | Dye residual ratio (%) |
| --- | --- | --- |
| Example 4 | Dye monomer 1 | 94 |
| Example 5 | Dye monomer 2 | 80 |
| Example 6 | Dye monomer 4 | 82 |
| Comp. Ex. 4 | Dye monomer 5 | 5 |
| Comp. Ex. 5 | Dye monomer 6 | 66 |
| Comp. Ex. 6 | Dye monomer 7 | 58 |
| Comp. Ex. 7 | Dye monomer 3 | 14 |
| Comp. Ex. 8 | Rhodamine 6G | 18 |

Observation of the glass wafers after heating showed remaining of a red coat in Examples 4 to 6, while the dyes were decomposed and become colorless and transparent in Comparative Examples 4 to 8. From this result and the results shown by Table 1, it has been demonstrated that the dye monomers 1, 2 and 4 showed superior heat resistance, as compared with rhodamine 6G not having a polymerizable group, the dye monomers 3 and 5 to 7, obtained by introduction of a polymerizable group into rhodamine B which is known as a general red dye.

Example 7

Synthesis of a Dye Polymer 1

Into a 200 mL round-bottom flask equipped with a stirring apparatus, a cooling condenser, a thermometer and a nitrogen introducing tube, 27.9 g of propylene glycol monomethyl ether acetate (produced by Wako Pure Chemical Industries, Ltd.) was charged, and heated until inner temperature reached to 90° C. under nitrogen gas flow. Next, a solution mixed with 3.0 g of the dye monomer 1 (compound 6), 50.1 g of benzyl methacrylate (produced by Wako Pure Chemical Industries, Ltd.), 6.9 g of methacrylic acid (produced by Wako Pure Chemical Industries, Ltd.), 9.6 g of dimethyl 2,2'-azobis(2-methylpropionate) (polymerization initiator V-601, produced by Wako Pure Chemical Industries, Ltd.) and 27.9 g of propylene glycol monomethyl ether acetate (produced by Wako Pure Chemical Industries, Ltd.) was dropped therein taking 2 hours. After that, the resulting solution was reacted at 90° C. for 2 hours. After the reaction, the solution was cooled down to room temperature, and 48.6 g of propylene glycol monomethyl ether acetate was added and diluted to obtain a dye polymer (compound 6/benzyl methacrylate/methacrylic acid=3.0/50.1/6.9). This was referred to as the polymer 1.

Example 8

Evaluation of Heat Resistance of the Dye Polymer 1 (230° C. for 0.5 Hour)

Heat resistance of the dye polymer 1 obtained in Example 7 was evaluated as follows.

That is, the resulting dye polymer 1 was spin coated onto 3 inch glass wafer (Eagle XG, manufactured by Corning Inc.), and then dried for 90 seconds on a hot plate heated at 90° C., to obtain a thin film having a film thickness of 1 μm. Absorbance ($\lambda a$) at the maximum absorption wavelength of the resulting thin film was measured using a spectrophotometer (Spectrophotometer UV-2550, manufactured by Shimadzu Corp.). After that, the glass wafer was heated for 30 minutes on the hot plate heated at 230° C., and then absorbance ($\lambda b$) at the maximum absorption wavelength was measured again. From values of $\lambda a$ and $\lambda b$, dye residual ratio (%) was determined from the following equation.

Dye residual ratio (%)=($\lambda b/\lambda a$)×100

Example 9

Synthesis of a Dye Polymer 2

The dye polymer 2 was synthesized similarly as in Example 7, except for using the dye monomer 4 obtained in Example 3, instead of the dye monomer 1.

Example 10

Evaluation of Heat Resistance of the Dye Polymer 2 (230° C. for 0.5 Hour)

Heat resistance was evaluated similarly as in Example 8, except for using the dye polymer 2 obtained in Example 9, instead of the dye polymer 1.

Comparative Example 9

Synthesis of a Dye Polymer 3

The dye polymer 3 was synthesized similarly as in Example 7, except for using the dye monomer 5 obtained in Comparative Example 1, instead of the dye monomer 1.

Comparative Example 10

Evaluation of Heat Resistance of the Dye Polymer 3 (230° C. for 0.5 Hour)

Heat resistance was evaluated similarly as in Example 8, except for using the dye polymer 3 obtained in Comparative Example 9, instead of the dye polymer 1.

Comparative Example 11

Synthesis of a Dye Polymer 4

The dye polymer 4 was synthesized similarly as in Example 7, except for using the dye monomer 6 obtained in Comparative Example 2, instead of the dye monomer 1.

Comparative Example 12

Evaluation of Heat Resistance of the Dye Polymer 4 (230° C. for 0.5 Hour)

Heat resistance was evaluated similarly as in Example 8, except for using the dye polymer 4 obtained in Comparative Example 11, instead of the dye polymer 1.

Comparative Example 13

Synthesis of a Dye Polymer 5

The dye polymer 5 was synthesized similarly as in Example 7, except for using the dye monomer 7 obtained in Comparative Example 3, instead of the dye monomer 1.

Comparative Example 14

Evaluation of Heat Resistance of the Dye Polymer 5 (230° C. for 0.5 Hour)

Heat resistance was evaluated similarly as in Example 8, except for using the dye polymer 5 obtained in Comparative Example 13, instead of the dye polymer 1.

Comparative Example 15

Synthesis of a Dye Polymer 6

The dye polymer 6 was synthesized similarly as in Example 7, except for using the dye monomer 3 obtained in Example 3 (2), instead of the dye monomer 1, and using propylene glycol as a solvent.

Comparative Example 16

Evaluation of Heat Resistance of the Dye Polymer 6 (230° C. for 0.5 Hour)

Heat resistance was evaluated similarly as in Example 8, except for using the dye polymer 6 obtained in Comparative Example 15, instead of the dye polymer 1.

Results of Examples 8 and 10, as well as Comparative Examples 10, 12, 14 and 16 are shown in Table 2.

TABLE 2

|  |  | Dye residual ratio (%) |
|---|---|---|
| Example 8 | Dye polymer 1 | 96 |
| Example 10 | Dye polymer 2 | 84 |
| Comp. Ex. 10 | Dye polymer 3 | 12 |
| Comp. Ex. 12 | Dye polymer 4 | 76 |
| Comp. Ex. 14 | Dye polymer 5 | 72 |
| Comp. Ex. 16 | Dye polymer 6 | 12 |

From the results shown by Table 2, it has been demonstrated that the dye polymers 1 and 2 more enhance heat resistance by being converted to polymers, because of having higher dye residual ratio as compared with the dye monomers 1 and 4.

On the other hand, it has been demonstrated that the dye polymer 3 or the dye polymer 6 has poor heat resistance even by being converted to a polymer. In addition, the dye polymers 4 and 5 did not show sufficient heat resistance as compared with the dye polymers 1 and 2.

The invention claimed is:

1. A compound represented by the following general formula (1):

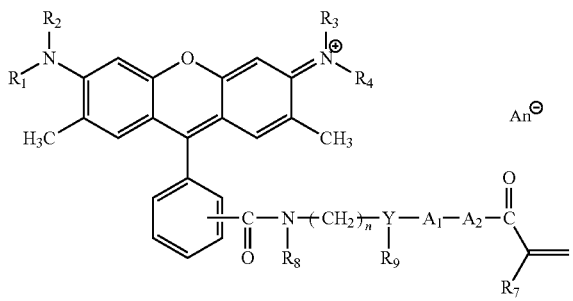

wherein $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenated alkyl group having 1 to 6 carbon atoms, a phenyl group having a substituent or not having a substituent, or a benzyl group having a substituent or not having a substituent; $R_7$ represents a hydrogen atom or a methyl group; $An^-$ represents an anion containing an aryl group having an electron-withdrawing substituent, a sulfonyl group having an electron-withdrawing substituent, or a halogenated alkyl group; $A_1$ represents an alkylene group having 1 to 6 carbon atoms which has at least one group selected from —OCO—, —COO— and —NHCONH— in the chain; or an alkylene group having 1 to 6 carbon atoms; and (a) when $A_1$ represents the alkylene group having 1 to 6 carbon atoms which has at least one group selected from —OCO—, —COO— and —NHCONH— in the chain, $A_2$ represents —NH— or —O—; Y represents a nitrogen atom or the group represented by the following formula (1-1):

n represents an integer of 0 to 3; $R_8$ represents a hydrogen atom; and $R_9$ represents a hydrogen atom; and (b) when $A_1$ represents the alkylene group having 1 to 6 carbon atoms, $A_2$ represents —NH—or —O—; Y represents a nitrogen atom or the group represented by the above formula (1-1); n represents 2; $R_8$ and $R_9$ form the following cyclic structure of a 6 membered ring

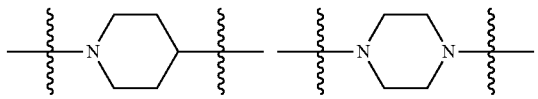

together with —N—$(CH_2)_n$—Y— bonding thereto.

2. The compound according to claim 1, wherein the electron-withdrawing substituent in $An^-$ is a halogen atom.

3. The compound according to claim 1, wherein the electron-withdrawing substituent in $An^-$ is a fluorine atom.

4. The compound according to claim 1, wherein the electron-withdrawing substituent in $An^-$ is a quaternary boron anion.

5. The compound according to claim 1, wherein $An^-$ is a tetrakis(perfluorophenyl)borate anion.

6. A coloring composition comprising the compound according to claim 1.

7. A coloring composition for a color filter comprising the compound according to claim 1.

8. The compound according to claim 1, wherein the alkylene group having 1 to 6 carbon atoms which has at least one group selected from —OCO—, —COO— and —NHCONH—in the chain in $A_1$ is the groups represented by the following general formulae (21-3') or (21-4');

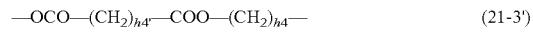

wherein $h_4$ and $h_4'$ each independently represent an integer of 1 to 3,

wherein $h_5'$ represents an integer of 1 to 6.

9. The compound according to claim 1, wherein $A_1$ is the group represented by the following general formula (21-3');

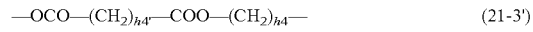

wherein $h_4$ and $h_4'$ each independently represent an integer of 1 to 3, $A_2$ is —NH— or —O—; Y is the nitrogen atom or the group represented by the above formula (1-1); n is the integer of 0 to 3; $R_8$ is the hydrogen atom; and $R_9$ is the hydrogen atom.

10. A polymer having a monomer unit derived from the compound represented by the following general formula (1):

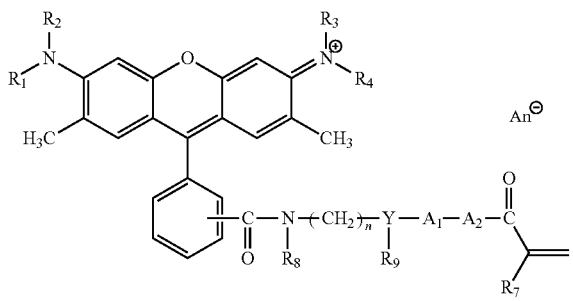

(1)

wherein $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenated alkyl group having 1 to 6 carbon atoms, a phenyl group having a substituent or not having a substituent, or a benzyl group having a substituent or not having a substituent; $R_7$ represents a hydrogen atom or a methyl group; An⁻ represents an anion containing an aryl group having an electron-withdrawing substituent, a sulfonyl group having an electron-withdrawing substituent, or a halogenated alkyl group; $A_1$ represents an alkylene group having 1 to 6 carbon atoms which has at least one group selected from —OCO—, —COO— and —NHCONH— in the chain; or an alkylene group having 1 to 6 carbon atoms; and (a) when $A_1$ represents the alkylene group having 1 to 6 carbon atoms which has at least one group selected from —OCO—, —COO— and —NHCONH— in the chain, $A_2$ represents —NH— or —O—; Y represents a nitrogen atom or the group represented by the following formula (1-1):

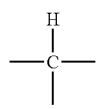

(1-1)

n represents an integer of 0 to 3: $R_9$ represents a hydrogen atom; and $R_9$ represents a hydrogen atom; and (b) when $A_1$ represents the alkylene group having 1 to 6 carbon atoms, $A_2$ represents —NH— or —O—; Y represents a nitrogen atom or the group represented by the above formula (1-1); n represents 2; $R_8$ and $R_9$ form the following cyclic structure of a 6 membered ring

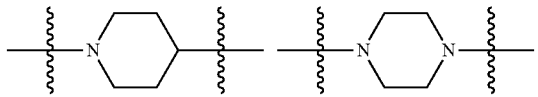

together with —N—$(CH_2)_n$—Y— bonding thereto.

11. The polymer according to claim 10, wherein the electron-withdrawing substituent in An⁻ is a halogen atom.

12. The polymer according to claim 10, wherein the electron-withdrawing substituent in An⁻ is a fluorine atom.

13. The polymer according to claim 10, wherein the electron-withdrawing substituent in An⁻ is a quaternary boron anion.

14. The polymer according to claim 10, wherein An⁻ is a tetrakis(perfluorophenyl)borate anion.

15. The polymer according to claim 10, wherein the polymer is a copolymer.

16. The polymer according to claim 15, wherein the copolymer is a copolymer having one to two kinds of monomer units derived from a compound represented by the following general formula (2), the general formula (3), the general formula (4) or the general formula (5), and the monomer unit derived from the compound represented by the above-described general formula (1), as configuration components:

(2)

wherein $R_{11}$ represents a hydrogen atom or a methyl group; $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms which has oxygen or no oxygen, a dialkylaminoalkyl group having 3 to 9 carbon atoms, a fluoroalkyl group having 1 to 18 carbon atoms, an N-alkylenephthalimide group having 9 to 14 carbon atoms, a group represented by the following general formula (2-1):

$$—(R_{21}—O)_q—R_{22}$$ (2-1)

wherein $R_{21}$ represents an alkylene group having 1 to 3 carbon atoms which has a hydroxy group as a substituent or no substituent; $R_{22}$ represents a phenyl group having a hydroxy group as a substituent or not having a substituent, or an alkyl group having 1 to 3 carbon atoms; and q represents an integer of 1 to 3, a group represented by the following general formula (2-2):

(2-2)

wherein $R_{23}$ to $R_{25}$ represent an alkyl group having 1 to 3 carbon atoms; $R_{26}$ represents an alkylene group having 1 to 3 carbon atoms, or a group represented by the following general formula (2-3):

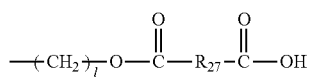
(2-3)

wherein l represents an integer of 1 to 6; and $R_{27}$ represents a phenylene group or a cyclohexylene group;

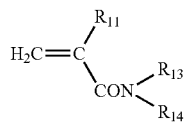
(3)

wherein $R_{11}$ is the same as described above; $R_{13}$ represents a hydrogen atom or an alkyl group having 1 to 3 carbon atoms; $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms; $R_{13}$ and $R_{14}$ may form a morpholino group together with a nitrogen atom adjacent thereto,

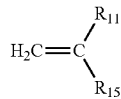
(4)

wherein $R_{15}$ represents a phenyl group or a pyrrolidino group; and $R_{11}$ is the same as described above,

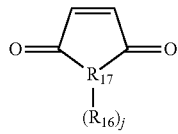
(5)

wherein $R_{17}$ represents a nitrogen atom or an oxygen atom; j represents 0 when $R_{17}$ is an oxygen atom, and 1 when $R_{17}$ is a nitrogen atom; $R_{16}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 6 to 10 carbon atoms, a halogenated cycloalkyl group having 6 to 7 carbon atoms, an aryl group having 6 to 10 carbon atoms, an aryl group having 6 to 10 carbon atoms, which has an alkyl group having 1 to 6 carbon atoms as a substituent, or a halogenated aryl group having 6 to 10 carbon atoms.

17. A coloring composition comprising the polymer according to claim 10.

18. A coloring composition for a color filter comprising the polymer according to claim 10.

19. The polymer according to claim 10, wherein the alkylene group having 1 to 6 carbon atoms which has at least one group selected from —OCO—, —COO— and —NHCONH— in the chain in $A_1$ is the groups represented by the following general formulae (21-3') or (21-4');

$$\text{—OCO—(CH}_2)_{h4}\text{—COO—(CH}_2)_{h4}\text{—} \quad (21\text{-}3')$$

wherein $h_4$ and $h_4'$ each independently represent an integer of 1 to 3, $$\text{—NHCONH—(CH}_2)_{h5'}\text{—} \quad (21\text{-}4')$$

wherein $h_5'$ represents an integer of 1 to 6.

20. The polymer according to claim 10, wherein $A_1$ is the group represented by the following general formula (21-3');

$$\text{—OCO—(CH}_2)_{h4}\text{—(CH}_2)_{h4}\text{—} \quad (21\text{-}3')$$

wherein $h_4$ and $h_4'$ each independently represent an integer of 1 to 3, $A_2$ is —NH— or —O—; Y is the nitrogen atom or the group represented by the above formula (1-1); n is the integer of 0 to 3; $R_8$ is the hydrogen atom; and $R_9$ is the hydrogen atom.

* * * * *